US008747463B2

(12) United States Patent
Fogarty et al.

(10) Patent No.: US 8,747,463 B2
(45) Date of Patent: Jun. 10, 2014

(54) METHODS OF USING A PROSTHESIS FIXTURING DEVICE

(75) Inventors: Thomas J. Fogarty, Portola Valley, CA (US); Michael J. Drews, Sacramento, CA (US); Ernest Lane, Huntington Beach, CA (US); Neil Holmgren, Chicago, IL (US); Federico Gutierrez, Pacifica, CA (US)

(73) Assignee: Medtronic, Inc., Minneapolis, MN (US)

( * ) Notice: Subject to any disclaimer, the term of this patent is extended or adjusted under 35 U.S.C. 154(b) by 245 days.

(21) Appl. No.: 13/197,364

(22) Filed: Aug. 3, 2011

(65) Prior Publication Data

US 2011/0283514 A1 Nov. 24, 2011

Related U.S. Application Data

(62) Division of application No. 10/646,639, filed on Aug. 22, 2003, now Pat. No. 8,021,421.

(51) Int. Cl.
*A61F 2/24* (2006.01)

(52) U.S. Cl.
USPC .......................................... 623/2.38; 623/2.36

(58) Field of Classification Search
USPC ........... 623/2.17, 2.18, 2.28–2.33, 2.36, 2.38, 623/2.4, 2.41, 2.37, 2.39
See application file for complete search history.

(56) References Cited

U.S. PATENT DOCUMENTS

| 3,143,742 A | 8/1964 | Cfromie |
| 3,320,974 A | 5/1967 | High et al. |
| 3,370,305 A | 2/1968 | Goott et al. |
| 3,371,352 A | 3/1968 | Siposs |
| 3,409,013 A | 11/1968 | Berry |
| 3,464,065 A | 9/1969 | Cromie |
| 3,546,710 A | 12/1970 | Shumakov et al. |
| 3,571,815 A | 3/1971 | Somyk |
| 3,574,865 A | 4/1971 | Hamaker |
| 3,628,535 A | 12/1971 | Ostrowsky et al. |
| 3,657,744 A | 4/1972 | Ersek |
| 3,686,740 A | 8/1972 | Shiley |
| 3,691,567 A | 9/1972 | Cromie |
| 3,710,744 A | 1/1973 | Goodenough et al. |
| 3,744,060 A | 7/1973 | Bellhouse et al. |
| 3,755,823 A | 9/1973 | Hanckock |

(Continued)

FOREIGN PATENT DOCUMENTS

| CN | 2356656 | 1/2000 |
| DE | 19532973 | 11/1996 |

(Continued)

OTHER PUBLICATIONS

Jansen et al., "Detachable Shape-Memory Sewing Ring for Heat Valves", Artif. Organs, 16(3):294-297, Helmholtz Institute for Biomedical Engineering, Technical University of Aachen, Aachen, Germany.

(Continued)

*Primary Examiner* — David Isabella
*Assistant Examiner* — Dinah Baria

(57) ABSTRACT

Devices for fixturing a prosthesis to a first mass and methods of making and using the same are disclosed. Complementary fixturing devices and methods of making and using the same are also disclosed. The devices can be used to attach a heart valve gasket body to a biological annulus.

12 Claims, 44 Drawing Sheets

(56) References Cited

U.S. PATENT DOCUMENTS

| | | |
|---|---|---|
| 3,800,403 A | 4/1974 | Anderson |
| 3,839,741 A | 10/1974 | Haller |
| 3,890,975 A | 6/1975 | McGregor |
| 3,959,827 A | 6/1976 | Kaster |
| 3,974,854 A | 8/1976 | Kurpanck |
| 3,996,623 A | 12/1976 | Kaster |
| 3,997,923 A | 12/1976 | Possis |
| 4,035,849 A | 7/1977 | Angell et al. |
| 4,054,144 A | 10/1977 | Hoffman et al. |
| 4,078,268 A | 3/1978 | Possis |
| 4,078,468 A | 3/1978 | Civitello |
| 4,084,268 A | 4/1978 | Ionexcu et al. |
| 4,106,129 A | 8/1978 | Carpentier et al. |
| 4,140,126 A | 2/1979 | Choudhury |
| 4,164,046 A | 8/1979 | Cooley |
| 4,172,295 A | 10/1979 | Batten |
| 4,211,325 A | 7/1980 | Wright |
| 4,217,665 A | 8/1980 | Bex et al. |
| 4,218,782 A | 8/1980 | Rygg |
| 4,245,358 A | 1/1981 | Moasser |
| 4,259,753 A | 4/1981 | Liotta et al. |
| 4,291,420 A | 9/1981 | Reul |
| 4,297,749 A | 11/1981 | Davis et al. |
| RE30,912 E | 4/1982 | Hancock |
| 4,343,048 A | 8/1982 | Ross et al. |
| 4,364,126 A | 12/1982 | Rosen et al. |
| 4,388,735 A | 6/1983 | Ionescu et al. |
| 4,441,216 A | 4/1984 | Ionescu et al. |
| 4,451,936 A | 6/1984 | Carpentier et al. |
| 4,470,157 A | 9/1984 | Love |
| 4,477,930 A | 10/1984 | Totten et al. |
| 4,485,816 A | 12/1984 | Krumme |
| 4,501,030 A | 2/1985 | Lane |
| 4,506,394 A | 3/1985 | Bedard |
| 4,535,483 A | 8/1985 | Klawitter et al. |
| 4,548,202 A | 10/1985 | Duncan |
| 4,605,407 A | 8/1986 | Black et al. |
| 4,626,255 A | 12/1986 | Reichart et al. |
| 4,629,459 A | 12/1986 | Ionescu et al. |
| 4,665,906 A | 5/1987 | Jervis |
| 4,666,442 A | 5/1987 | Arru et al. |
| 4,680,031 A | 7/1987 | Alonso |
| 4,683,883 A | 8/1987 | Martin |
| 4,687,483 A | 8/1987 | Fisher et al. |
| 4,692,164 A | 9/1987 | Dzemeshkevich et al. |
| 4,702,250 A | 10/1987 | Ovil et al. |
| 4,705,516 A | 11/1987 | Barone et al. |
| 4,725,274 A | 2/1988 | Lane et al. |
| 4,731,074 A | 3/1988 | Rousseau et al. |
| 4,743,253 A | 5/1988 | Magladry |
| 4,758,151 A | 7/1988 | Arru et al. |
| 4,775,378 A | 10/1988 | Knoch et al. |
| 4,778,461 A | 10/1988 | Pietsch et al. |
| 4,790,843 A | 12/1988 | Carpentier et al. |
| 4,816,029 A | 3/1989 | Penney et al. |
| 4,851,000 A | 7/1989 | Gupta |
| 4,865,600 A | 9/1989 | Carpentier et al. |
| 4,888,009 A | 12/1989 | Lederman et al. |
| 4,892,541 A | 1/1990 | Alonso |
| 4,917,097 A | 4/1990 | Proudian et al. |
| 4,917,698 A | 4/1990 | Carpentier et al. |
| 4,935,030 A | 6/1990 | Alonso |
| 4,960,424 A | 10/1990 | Grooters |
| 4,993,428 A | 2/1991 | Arms |
| 4,994,077 A | 2/1991 | Dobben |
| 5,002,567 A | 3/1991 | Bona et al. |
| 5,010,892 A | 4/1991 | Colvin et al. |
| 5,032,128 A | 7/1991 | Alonso |
| 5,035,709 A | 7/1991 | Wieting et al. |
| 5,037,434 A | 8/1991 | Lane |
| 5,071,431 A | 12/1991 | Sauter et al. |
| 5,104,406 A | 4/1992 | Curcio et al. |
| 5,123,913 A | 6/1992 | Wilk et al. |
| 5,147,391 A | 9/1992 | Lane |
| 5,163,953 A | 11/1992 | Vince |
| 5,163,954 A | 11/1992 | Curcio et al. |
| 5,163,955 A | 11/1992 | Love et al. |
| 5,178,633 A | 1/1993 | Peters |
| 5,192,303 A | 3/1993 | Gatturna |
| 5,258,023 A | 11/1993 | Reger |
| 5,316,016 A | 5/1994 | Adams et al. |
| 5,326,370 A | 7/1994 | Love et al. |
| 5,326,371 A | 7/1994 | Love et al. |
| 5,332,402 A | 7/1994 | Teitelbaum |
| 5,370,685 A | 12/1994 | Stevens |
| 5,376,112 A | 12/1994 | Duran |
| 5,396,887 A | 3/1995 | Imran |
| 5,397,346 A | 3/1995 | Walker et al. |
| 5,397,348 A | 3/1995 | Campbell et al. |
| 5,397,351 A | 3/1995 | Pavcnik et al. |
| 5,406,857 A | 4/1995 | Eberhardt et al. |
| 5,411,552 A | 5/1995 | Andersen et al. |
| 5,423,887 A | 6/1995 | Love et al. |
| 5,425,741 A | 6/1995 | Lemp et al. |
| 5,431,676 A | 7/1995 | Dubrul et al. |
| 5,449,384 A | 9/1995 | Johnson |
| 5,449,385 A | 9/1995 | Religa et al. |
| 5,469,868 A | 11/1995 | Reger |
| 5,476,510 A | 12/1995 | Eberhardt et al. |
| 5,488,789 A | 2/1996 | Religa et al. |
| 5,489,297 A | 2/1996 | Duran |
| 5,489,298 A | 2/1996 | Love et al. |
| 5,500,016 A | 3/1996 | Fisher |
| 5,531,784 A | 7/1996 | Love et al. |
| 5,533,515 A | 7/1996 | Coller et al. |
| 5,549,665 A | 8/1996 | Vesely et al. |
| 5,549,666 A | 8/1996 | Hata et al. |
| 5,554,185 A | 9/1996 | Block et al. |
| 5,562,729 A | 10/1996 | Purdy et al. |
| 5,571,175 A | 11/1996 | Vanney |
| 5,571,215 A | 11/1996 | Sterman et al. |
| 5,573,007 A | 11/1996 | Bobo, Sr. |
| 5,573,543 A | 11/1996 | Akopov |
| 5,578,076 A | 11/1996 | Krueger et al. |
| 5,584,803 A | 12/1996 | Stevens et al. |
| 5,584,879 A * | 12/1996 | Reimold et al. ............ 623/2.36 |
| 5,601,576 A | 2/1997 | Garrison |
| 5,607,470 A | 3/1997 | Milo |
| 5,613,982 A | 3/1997 | Goldstein |
| 5,618,307 A | 4/1997 | Donlon et al. |
| 5,626,607 A | 5/1997 | Malecki et al. |
| 5,628,789 A | 5/1997 | Vanney et al. |
| 5,662,704 A | 9/1997 | Gross |
| 5,669,917 A | 9/1997 | Sauer |
| 5,693,090 A | 12/1997 | Unsworth et al. |
| 5,695,503 A | 12/1997 | Kruegger et al. |
| 5,713,952 A | 2/1998 | Vanney et al. |
| 5,713,953 A | 2/1998 | Vallana et al. |
| 5,716,370 A | 2/1998 | Williamson |
| 5,716,399 A | 2/1998 | Love |
| 5,720,755 A | 2/1998 | Dakov |
| 5,725,554 A | 3/1998 | Simon |
| 5,728,064 A | 3/1998 | Burns et al. |
| 5,728,151 A | 3/1998 | Garrison et al. |
| 5,735,894 A | 4/1998 | Kruegger et al. |
| 5,752,522 A | 5/1998 | Murphy |
| 5,755,782 A | 5/1998 | Love et al. |
| 5,766,240 A | 6/1998 | Johnson |
| 5,776,187 A | 7/1998 | Krueger et al. |
| 5,776,188 A | 7/1998 | Shepherd et al. |
| 5,800,527 A | 9/1998 | Jansen et al. |
| 5,807,405 A | 9/1998 | Vanney et al. |
| 5,814,097 A | 9/1998 | Sterman et al. |
| 5,814,098 A | 9/1998 | Hinnenkamp et al. |
| 5,814,100 A | 9/1998 | Carpentier et al. |
| 5,824,060 A | 10/1998 | Christie et al. |
| 5,824,061 A | 10/1998 | Quijano et al. |
| 5,824,064 A | 10/1998 | Taheri |
| 5,830,239 A | 11/1998 | Toomes |
| 5,840,081 A | 11/1998 | Andersen et al. |
| 5,843,179 A | 12/1998 | Vanney et al. |
| 5,848,969 A | 12/1998 | Panescu et al. |
| 5,855,563 A | 1/1999 | Kaplan et al. |
| 5,855,601 A | 1/1999 | Bessler et al. |

(56) References Cited

U.S. PATENT DOCUMENTS

| | | | |
|---|---|---|---|
| 5,855,603 A | 1/1999 | Reif | |
| 5,860,992 A | 1/1999 | Daniel | |
| 5,861,028 A | 1/1999 | Angell | |
| 5,865,801 A | 2/1999 | Houser | |
| 5,873,906 A | 2/1999 | Lau et al. | |
| 5,876,436 A | 3/1999 | Vanney et al. | |
| 5,879,371 A | 3/1999 | Gardiner et al. | |
| 5,891,160 A | 4/1999 | Williamson, IV et al. | |
| 5,891,195 A | 4/1999 | Klostermeyer et al. | |
| 5,895,420 A | 4/1999 | Mirsch, II et al. | |
| 5,902,308 A | 5/1999 | Murphy | |
| 5,908,450 A | 6/1999 | Gross et al. | |
| 5,908,452 A | 6/1999 | Bokros et al. | |
| 5,910,170 A | 6/1999 | Reiminik et al. | |
| 5,919,147 A | 7/1999 | Jain | |
| 5,921,934 A | 7/1999 | Teo | |
| 5,921,935 A | 7/1999 | Hickey | |
| 5,924,984 A | 7/1999 | Rao | |
| 5,925,061 A | 7/1999 | Ogi et al. | |
| 5,925,063 A | 7/1999 | Khosravi | |
| 5,931,969 A | 8/1999 | Carpentier et al. | |
| 5,935,163 A | 8/1999 | Gabbay | |
| 5,957,940 A | 9/1999 | Tanner et al. | |
| 5,957,949 A | 9/1999 | Leonhardt et al. | |
| 5,961,549 A | 10/1999 | Nguyen et al. | |
| 5,961,550 A | 10/1999 | Carpentier et al. | |
| 5,972,004 A | 10/1999 | Williamson, IV et al. | |
| 5,972,024 A | 10/1999 | Northrup, III | |
| 5,976,183 A | 11/1999 | Ritz | |
| 5,984,959 A | 11/1999 | Robertson et al. | |
| 5,984,973 A | 11/1999 | Girard et al. | |
| 6,007,577 A | 12/1999 | Vanney et al. | |
| 6,010,531 A | 1/2000 | Donlon et al. | |
| 6,042,607 A | 3/2000 | Williamson, IV et al. | |
| 6,045,576 A | 4/2000 | Starr et al. | |
| 6,059,827 A | 5/2000 | Fenton, Jr. | |
| 6,066,160 A | 5/2000 | Colvin et al. | |
| 6,068,657 A | 5/2000 | Lapeyre et al. | |
| 6,074,401 A | 6/2000 | Gardiner et al. | |
| 6,074,417 A | 6/2000 | Peredo | |
| 6,074,418 A | 6/2000 | Buchanan et al. | |
| 6,081,737 A | 6/2000 | Shah | |
| 6,083,179 A | 7/2000 | Oredsson | |
| 6,096,074 A | 8/2000 | Pedros | |
| 6,099,475 A | 8/2000 | Seward et al. | |
| 6,102,944 A | 8/2000 | Huynh et al. | |
| 6,106,550 A * | 8/2000 | Magovern et al. | 623/2.38 |
| 6,110,200 A | 8/2000 | Hinnenkamp | |
| 6,113,632 A | 9/2000 | Reif | |
| 6,117,091 A | 9/2000 | Young et al. | |
| 6,126,007 A | 10/2000 | Kari et al. | |
| 6,129,758 A | 10/2000 | Love | |
| 6,139,575 A | 10/2000 | Shu et al. | |
| 6,143,024 A | 11/2000 | Campbell et al. | |
| 6,143,025 A | 11/2000 | Stobie et al. | |
| 6,149,658 A | 11/2000 | Gardiner et al. | |
| 6,152,935 A | 11/2000 | Kammerer et al. | |
| 6,162,233 A | 12/2000 | Williamson, IV et al. | |
| 6,165,183 A | 12/2000 | Kuehn et al. | |
| 6,168,614 B1 | 1/2001 | Andersen et al. | |
| 6,176,877 B1 | 1/2001 | Buchanan et al. | |
| 6,176,977 B1 | 1/2001 | Taylor et al. | |
| 6,183,512 B1 * | 2/2001 | Howanec et al. | 623/2.36 |
| 6,197,054 B1 | 3/2001 | Hamblin, Jr. et al. | |
| 6,200,306 B1 | 3/2001 | Klostermeyer | |
| 6,203,553 B1 | 3/2001 | Robertson | |
| 6,214,043 B1 | 4/2001 | Kruegger et al. | |
| 6,217,610 B1 | 4/2001 | Carpentier et al. | |
| 6,217,611 B1 | 4/2001 | Klostermeyer | |
| 6,231,561 B1 | 5/2001 | Frazier et al. | |
| 6,231,602 B1 | 5/2001 | Carpentier et al. | |
| 6,241,765 B1 | 6/2001 | Griffin et al. | |
| 6,245,102 B1 | 6/2001 | Jayaraman | |
| 6,245,105 B1 | 6/2001 | Nguyen et al. | |
| 6,254,636 B1 | 7/2001 | Peredo | |
| 6,264,691 B1 | 7/2001 | Gabbay | |
| 6,270,526 B1 | 8/2001 | Cox | |
| 6,270,527 B1 | 8/2001 | Campbell et al. | |
| 6,283,127 B1 | 9/2001 | Sterman et al. | |
| 6,283,995 B1 | 9/2001 | Moe et al. | |
| 6,287,339 B1 | 9/2001 | Vazquez et al. | |
| 6,290,674 B1 | 9/2001 | Roue et al. | |
| 6,299,638 B1 | 10/2001 | Sauter | |
| 6,309,417 B1 | 10/2001 | Spence | |
| 6,312,447 B1 | 11/2001 | Grimes | |
| 6,312,465 B1 | 11/2001 | Griffin et al. | |
| 6,319,280 B1 | 11/2001 | Schoon | |
| 6,319,281 B1 | 11/2001 | Patel | |
| 6,322,588 B1 | 11/2001 | Ogle et al. | |
| 6,328,727 B1 | 12/2001 | Frazier et al. | |
| 6,328,763 B1 | 12/2001 | Love et al. | |
| 6,338,740 B1 | 1/2002 | Carpentier | |
| 6,350,281 B1 | 2/2002 | Rhee | |
| 6,358,278 B1 | 3/2002 | Brendzel et al. | |
| 6,358,556 B1 | 3/2002 | Ding et al. | |
| 6,371,983 B1 | 4/2002 | Lane | |
| 6,391,053 B1 | 5/2002 | Brendzel et al. | |
| 6,395,025 B1 | 5/2002 | Fordenbacher et al. | |
| 6,402,780 B2 | 6/2002 | Williamson, IV et al. | |
| 6,409,759 B1 | 6/2002 | Peredo | |
| 6,413,275 B1 | 7/2002 | Nguyen et al. | |
| 6,419,696 B1 | 7/2002 | Ortiz et al. | |
| 6,425,902 B1 | 7/2002 | Love | |
| 6,425,916 B1 | 7/2002 | Garrison et al. | |
| 6,440,164 B1 | 8/2002 | DiMatteo et al. | |
| 6,447,524 B1 | 9/2002 | Knodel | |
| 6,454,799 B1 | 9/2002 | Schreck | |
| 6,458,153 B1 | 10/2002 | Bailey et al. | |
| 6,461,382 B1 | 10/2002 | Cao | |
| 6,468,305 B1 | 10/2002 | Otte | |
| 6,503,272 B2 | 1/2003 | Duerig et al. | |
| 6,514,265 B2 | 2/2003 | Ho et al. | |
| 6,530,952 B2 | 3/2003 | Vesely | |
| 6,547,827 B2 | 4/2003 | Carpentier et al. | |
| 6,551,332 B1 | 4/2003 | Nguyen et al. | |
| 6,558,418 B2 | 5/2003 | Carpentier et al. | |
| 6,569,196 B1 | 5/2003 | Vesely | |
| 6,582,462 B1 | 6/2003 | Andersen et al. | |
| 6,585,766 B1 | 7/2003 | Huynh et al. | |
| 6,589,279 B1 | 7/2003 | Anderson et al. | |
| 6,598,307 B2 | 7/2003 | Love et al. | |
| 6,602,289 B1 | 8/2003 | Colvin et al. | |
| 6,607,541 B1 | 8/2003 | Gardiner et al. | |
| 6,613,059 B2 | 9/2003 | Ho et al. | |
| 6,613,085 B1 | 9/2003 | Anderson et al. | |
| 6,641,593 B1 | 11/2003 | Schaller et al. | |
| 6,652,578 B2 | 11/2003 | Bailey et al. | |
| 6,660,032 B2 | 12/2003 | Klumb et al. | |
| 6,676,671 B2 | 1/2004 | Robertson et al. | |
| 6,678,962 B1 | 1/2004 | Love et al. | |
| 6,682,559 B2 | 1/2004 | Myers et al. | |
| 6,685,739 B2 | 2/2004 | DiMatteo et al. | |
| 6,692,513 B2 | 2/2004 | Streeter et al. | |
| 6,695,859 B1 | 2/2004 | Golden et al. | |
| 6,709,457 B1 | 3/2004 | Otte et al. | |
| 6,716,243 B1 | 4/2004 | Colvin et al. | |
| 6,716,244 B2 | 4/2004 | Klaco | |
| 6,719,789 B2 | 4/2004 | Cox | |
| 6,719,790 B2 | 4/2004 | Brendzel et al. | |
| 6,730,118 B2 | 5/2004 | Spenser et al. | |
| 6,733,525 B2 | 5/2004 | Yang et al. | |
| 6,764,508 B1 | 7/2004 | Roehe et al. | |
| 6,767,362 B2 | 7/2004 | Schreck | |
| 6,769,434 B2 | 8/2004 | Liddicoat et al. | |
| 6,776,785 B1 | 8/2004 | Yencho | |
| 6,786,924 B2 | 9/2004 | Ryan et al. | |
| 6,786,925 B1 | 9/2004 | Schoon et al. | |
| 6,790,229 B1 | 9/2004 | Berreklouw | |
| 6,790,230 B2 | 9/2004 | Beyersdorf et al. | |
| 6,805,711 B2 | 10/2004 | Quijano et al. | |
| 6,830,585 B1 | 12/2004 | Artof et al. | |
| 6,833,924 B2 | 12/2004 | Love et al. | |
| 6,837,902 B2 | 1/2005 | Nguyen et al. | |
| 6,846,324 B2 | 1/2005 | Stobie | |

(56) References Cited

U.S. PATENT DOCUMENTS

| | | | |
|---|---|---|---|
| 6,846,325 B2 | 1/2005 | Liddicoat |
| 6,872,226 B2 | 3/2005 | Cali et al. |
| 6,893,459 B1 | 5/2005 | Macoviak |
| 6,893,460 B2 | 5/2005 | Spenser et al. |
| 6,896,690 B1 | 5/2005 | Lambrecht et al. |
| 6,908,481 B2 | 6/2005 | Cribier |
| 6,911,043 B2 | 6/2005 | Myers et al. |
| 6,913,607 B2 | 7/2005 | Ainsworth et al. |
| 6,918,917 B1 | 7/2005 | Nguyen et al. |
| 6,921,407 B2 | 7/2005 | Nguyen et al. |
| 6,926,730 B1 | 8/2005 | Nguyen et al. |
| 6,929,653 B2 | 8/2005 | Streeter |
| 6,939,365 B1 | 9/2005 | Fogarty |
| 6,945,980 B2 | 9/2005 | Nguyen et al. |
| 6,945,997 B2 | 9/2005 | Huynh et al. |
| 6,960,221 B2 | 11/2005 | Ho et al. |
| 6,974,476 B2 | 12/2005 | McGuckin et al. |
| 7,011,681 B2 | 3/2006 | Vesely |
| 7,025,780 B2 | 4/2006 | Gabbay |
| 7,037,333 B2 | 5/2006 | Myers et al. |
| 7,070,616 B2 | 7/2006 | Majercak et al. |
| 7,083,648 B2 | 8/2006 | Yu |
| 7,097,659 B2 | 8/2006 | Woolfson et al. |
| 7,101,396 B2 | 9/2006 | Artof et al. |
| 7,137,184 B2 | 11/2006 | Schreck |
| 7,141,064 B2 | 11/2006 | Scott et al. |
| 7,147,663 B1 | 12/2006 | Berg et al. |
| 7,153,324 B2 | 12/2006 | Case et al. |
| 7,172,625 B2 | 2/2007 | Shu et al. |
| 7,175,659 B2 | 2/2007 | Hill et al. |
| 7,182,769 B2 | 2/2007 | Ainsworth et al. |
| 7,186,265 B2 | 3/2007 | Sharkawy et al. |
| 7,195,641 B2 | 3/2007 | Palmaz et al. |
| 7,201,761 B2 | 4/2007 | Woofson et al. |
| 7,201,771 B2 | 4/2007 | Lane |
| 7,201,772 B2 | 4/2007 | Schwammenthal et al. |
| 7,214,344 B2 | 5/2007 | Carpentier et al. |
| 7,238,200 B2 | 7/2007 | Lee et al. |
| 7,252,682 B2 | 8/2007 | Seguin |
| 7,261,732 B2 | 8/2007 | Justino |
| 7,300,463 B2 | 11/2007 | Liddicoat |
| RE40,377 E | 6/2008 | Williamson, IV et al. |
| 7,393,360 B2 | 7/2008 | Spenser et al. |
| 7,422,603 B2 | 9/2008 | Lane |
| 7,445,632 B2 | 11/2008 | McGuckin et al. |
| 7,513,909 B2 | 4/2009 | Lane et al. |
| 7,547,313 B2 | 6/2009 | Gardiner et al. |
| 7,556,647 B2 | 7/2009 | Drews et al. |
| 7,578,843 B2 | 8/2009 | Shu |
| 7,597,710 B2 | 10/2009 | Obermiller |
| 7,597,711 B2 | 10/2009 | Drews et al. |
| 7,708,775 B2 | 5/2010 | Rowe et al. |
| 7,717,955 B2 | 5/2010 | Lane et al. |
| 7,722,643 B2 | 5/2010 | Ho et al. |
| 7,744,611 B2 | 6/2010 | Nguyen et al. |
| 7,763,040 B2 | 7/2010 | Schaller et al. |
| 7,771,469 B2 | 8/2010 | Liddicoat et al. |
| 7,803,184 B2 | 9/2010 | McGuckin et al. |
| 2001/0007956 A1 | 7/2001 | Letac et al. |
| 2001/0018592 A1 | 8/2001 | Schaller et al. |
| 2001/0021872 A1 | 9/2001 | Bailey et al. |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0044656 A1 | 11/2001 | Williamson et al. |
| 2001/0049492 A1 | 12/2001 | Frazier et al. |
| 2002/0026238 A1 | 2/2002 | Lane et al. |
| 2002/0032480 A1 | 3/2002 | Spence et al. |
| 2002/0032481 A1 | 3/2002 | Gabbay |
| 2002/0035361 A1 | 3/2002 | Houser et al. |
| 2002/0040184 A1 | 4/2002 | Brown et al. |
| 2002/0055774 A1 | 5/2002 | Liddicoat |
| 2002/0058994 A1 | 5/2002 | Hill et al. |
| 2002/0058995 A1 | 5/2002 | Stevens |
| 2002/0077555 A1 | 6/2002 | Schwartz |
| 2002/0077698 A1 | 6/2002 | Peredo |
| 2002/0091441 A1 | 7/2002 | Guzik |
| 2002/0116054 A1 | 8/2002 | Lundell et al. |
| 2002/0123802 A1 | 9/2002 | Snyders |
| 2002/0128684 A1 | 9/2002 | Foerster |
| 2002/0138138 A1 | 9/2002 | Yang |
| 2002/0151970 A1 | 10/2002 | Garrison et al. |
| 2002/0173842 A1 | 11/2002 | Buchanan |
| 2002/0177223 A1 | 11/2002 | Ogle et al. |
| 2002/0183834 A1 | 12/2002 | Klaco |
| 2002/0184827 A1* | 12/2002 | Duffy .............................. 49/463 |
| 2002/0188348 A1 | 12/2002 | DiMatteo et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023302 A1 | 1/2003 | Moe et al. |
| 2003/0023303 A1 | 1/2003 | Palmaz et al. |
| 2003/0036791 A1 | 2/2003 | Philipp et al. |
| 2003/0036795 A1 | 2/2003 | Andersen et al. |
| 2003/0040792 A1 | 2/2003 | Gabbay |
| 2003/0045902 A1 | 3/2003 | Weadeock |
| 2003/0050693 A1 | 3/2003 | Quijano et al. |
| 2003/0055495 A1 | 3/2003 | Pease et al. |
| 2003/0109922 A1 | 6/2003 | Peterson |
| 2003/0109924 A1 | 6/2003 | Cribier |
| 2003/0114913 A1 | 6/2003 | Spenser et al. |
| 2003/0125793 A1 | 7/2003 | Vesely |
| 2003/0130729 A1 | 7/2003 | Paniagua et al. |
| 2003/0136417 A1 | 7/2003 | Fonseca et al. |
| 2003/0149477 A1 | 8/2003 | Gabbay |
| 2003/0149478 A1 | 8/2003 | Figulla et al. |
| 2003/0153974 A1 | 8/2003 | Spenser et al. |
| 2003/0167089 A1 | 9/2003 | Lane |
| 2003/0191481 A1 | 10/2003 | Nguyen et al. |
| 2003/0199963 A1 | 10/2003 | Tower et al. |
| 2003/0199971 A1 | 10/2003 | Tower et al. |
| 2003/0199974 A1 | 10/2003 | Lee et al. |
| 2003/0229394 A1 | 12/2003 | Ogle et al. |
| 2003/0236568 A1 | 12/2003 | Hojeibane et al. |
| 2004/0015232 A1 | 1/2004 | Shu |
| 2004/0019374 A1 | 1/2004 | Hojeibane et al. |
| 2004/0024452 A1 | 2/2004 | Kruse et al. |
| 2004/0030381 A1 | 2/2004 | Shu |
| 2004/0034411 A1 | 2/2004 | Quijano et al. |
| 2004/0039436 A1 | 2/2004 | Spenser et al. |
| 2004/0044406 A1 | 3/2004 | Woolfson |
| 2004/0050393 A1 | 3/2004 | Golden et al. |
| 2004/0068276 A1 | 4/2004 | Golden et al. |
| 2004/0078074 A1 | 4/2004 | Anderson et al. |
| 2004/0093075 A1 | 5/2004 | Kuehne |
| 2004/0102797 A1 | 5/2004 | Golden et al. |
| 2004/0106976 A1 | 6/2004 | Bailey et al. |
| 2004/0106990 A1 | 6/2004 | Spence et al. |
| 2004/0122514 A1 | 6/2004 | Fogarty et al. |
| 2004/0122516 A1 | 6/2004 | Fogarty et al. |
| 2004/0122526 A1 | 6/2004 | Imran |
| 2004/0167573 A1 | 8/2004 | Williamson, IV et al. |
| 2004/0167620 A1 | 8/2004 | Ortiz et al. |
| 2004/0176839 A1 | 9/2004 | Huynh et al. |
| 2004/0186563 A1 | 9/2004 | Lobbi |
| 2004/0186565 A1 | 9/2004 | Schreck |
| 2004/0193261 A1 | 9/2004 | Berreklouw |
| 2004/0199176 A1 | 10/2004 | Berreklouw |
| 2004/0206363 A1 | 10/2004 | McCarthy et al. |
| 2004/0210304 A1 | 10/2004 | Seguin et al. |
| 2004/0210305 A1 | 10/2004 | Shu |
| 2004/0210307 A1 | 10/2004 | Khairkhahan |
| 2004/0225355 A1 | 11/2004 | Stevens |
| 2004/0225356 A1 | 11/2004 | Frater |
| 2004/0236411 A1 | 11/2004 | Sarac et al. |
| 2004/0260389 A1 | 12/2004 | Case et al. |
| 2004/0260390 A1 | 12/2004 | Sarac et al. |
| 2005/0010285 A1 | 1/2005 | Lambrecht et al. |
| 2005/0027348 A1 | 2/2005 | Case et al. |
| 2005/0033398 A1 | 2/2005 | Seguin |
| 2005/0043760 A1 | 2/2005 | Fogarty |
| 2005/0043790 A1 | 2/2005 | Seguin |
| 2005/0060029 A1 | 3/2005 | Le et al. |

(56) References Cited

U.S. PATENT DOCUMENTS

| | | |
|---|---|---|
| 2005/0065594 A1 | 3/2005 | DiMatteo et al. |
| 2005/0065601 A1 | 3/2005 | Lee et al. |
| 2005/0065614 A1 | 3/2005 | Stinson |
| 2005/0070924 A1 | 3/2005 | Schaller et al. |
| 2005/0075584 A1 | 4/2005 | Cali |
| 2005/0075659 A1 | 4/2005 | Realyvasquez et al. |
| 2005/0075667 A1 | 4/2005 | Ho et al. |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0075730 A1 | 4/2005 | Myers et al. |
| 2005/0080454 A1 | 4/2005 | Drews |
| 2005/0096738 A1 | 5/2005 | Cali et al. |
| 2005/0098547 A1 | 5/2005 | Cali et al. |
| 2005/0101975 A1 | 5/2005 | Nguyen et al. |
| 2005/0107871 A1 | 5/2005 | Realyvasquez et al. |
| 2005/0131429 A1 | 6/2005 | Ho et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137702 A1 | 6/2005 | Haug et al. |
| 2005/0150775 A1 | 7/2005 | Zhang et al. |
| 2005/0159811 A1 | 7/2005 | Lane |
| 2005/0165477 A1 | 7/2005 | Anduiza et al. |
| 2005/0165479 A1 | 7/2005 | Drews et al. |
| 2005/0182483 A1 | 8/2005 | Osborne et al. |
| 2005/0182486 A1 | 8/2005 | Gabbay |
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0216079 A1 | 9/2005 | MaCoviak |
| 2005/0222674 A1 | 10/2005 | Paine |
| 2005/0234546 A1 | 10/2005 | Nugent et al. |
| 2005/0240259 A1 | 10/2005 | Sisken et al. |
| 2005/0240263 A1 | 10/2005 | Fogarty |
| 2005/0251252 A1 | 11/2005 | Stobie |
| 2005/0261765 A1 | 11/2005 | Liddicoat |
| 2005/0283231 A1 | 12/2005 | Haug et al. |
| 2006/0004389 A1 | 1/2006 | Nguyen et al. |
| 2006/0025857 A1 | 2/2006 | Bergheim et al. |
| 2006/0052867 A1 | 3/2006 | Revuelta et al. |
| 2006/0058871 A1 | 3/2006 | Zakay et al. |
| 2006/0058872 A1 | 3/2006 | Salahieh et al. |
| 2006/0074484 A1 | 4/2006 | Huber |
| 2006/0085060 A1 | 4/2006 | Campbell |
| 2006/0095125 A1 | 5/2006 | Chinn et al. |
| 2006/0122634 A1 | 6/2006 | Ino |
| 2006/0122692 A1 | 6/2006 | Gilad et al. |
| 2006/0135964 A1 | 6/2006 | Vesely |
| 2006/0136052 A1 | 6/2006 | Vesely |
| 2006/0136054 A1 | 6/2006 | Berg et al. |
| 2006/0149360 A1 | 7/2006 | Schwammenthal et al. |
| 2006/0149367 A1 | 7/2006 | Sieracki |
| 2006/0154230 A1 | 7/2006 | Cunanan |
| 2006/0161249 A1 | 7/2006 | Realyvasquez et al. |
| 2006/0167543 A1 | 7/2006 | Bailey et al. |
| 2006/0173537 A1 | 8/2006 | Yang et al. |
| 2006/0195183 A1 | 8/2006 | Navia et al. |
| 2006/0195184 A1 | 8/2006 | Lane |
| 2006/0195185 A1 | 8/2006 | Lane |
| 2006/0195186 A1 | 8/2006 | Drews |
| 2006/0207031 A1 | 9/2006 | Cunanan et al. |
| 2006/0229708 A1 | 10/2006 | Powell et al. |
| 2006/0235508 A1 | 10/2006 | Lane |
| 2006/0241745 A1 | 10/2006 | Solem |
| 2006/0246888 A1 | 11/2006 | Bender et al. |
| 2006/0253191 A1 | 11/2006 | Salahieh et al. |
| 2006/0259134 A1 | 11/2006 | Schwammenthal et al. |
| 2006/0259135 A1 | 11/2006 | Navia et al. |
| 2006/0259136 A1 | 11/2006 | Nguyen et al. |
| 2006/0265056 A1 | 11/2006 | Nguyen et al. |
| 2006/0271172 A1 | 11/2006 | Tehrani |
| 2006/0271175 A1 | 11/2006 | Woofson et al. |
| 2006/0276888 A1 | 12/2006 | Lee |
| 2006/0287717 A1 | 12/2006 | Rowe et al. |
| 2006/0287719 A1 | 12/2006 | Rowe et al. |
| 2007/0005129 A1 | 1/2007 | Damm et al. |
| 2007/0010835 A1 | 1/2007 | Breton et al. |
| 2007/0010876 A1 | 1/2007 | Salahieh et al. |
| 2007/0010877 A1 | 1/2007 | Salahieh et al. |
| 2007/0016285 A1 | 1/2007 | Lane |
| 2007/0016286 A1 | 1/2007 | Herrmann et al. |
| 2007/0016288 A1 | 1/2007 | Gurskis |
| 2007/0027461 A1 | 2/2007 | Gardiner et al. |
| 2007/0043435 A1 | 2/2007 | Seguin et al. |
| 2007/0078509 A1 | 4/2007 | Lotfy |
| 2007/0078510 A1 | 4/2007 | Ryan |
| 2007/0095698 A1 | 5/2007 | Cambron |
| 2007/0100440 A1 | 5/2007 | Figulla et al. |
| 2007/0106313 A1 | 5/2007 | Golden et al. |
| 2007/0129794 A1 | 6/2007 | Realyvasquez |
| 2007/0129795 A1 | 6/2007 | Hill et al. |
| 2007/0142848 A1 | 6/2007 | Ainsworth et al. |
| 2007/0142906 A1 | 6/2007 | Figulla et al. |
| 2007/0142907 A1 | 6/2007 | Moaddeb et al. |
| 2007/0150053 A1 | 6/2007 | Gurskis |
| 2007/0156233 A1 | 7/2007 | Kapadia et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0162113 A1 | 7/2007 | Sharkawy et al. |
| 2007/0179604 A1 | 8/2007 | Lane |
| 2007/0185565 A1 | 8/2007 | Schwammenthal et al. |
| 2007/0198097 A1 | 8/2007 | Zegdi |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0225801 A1 | 9/2007 | Drews et al. |
| 2007/0233237 A1 | 10/2007 | Krivoruchko |
| 2007/0239266 A1 | 10/2007 | Birdsall |
| 2007/0239269 A1 | 10/2007 | Dolan et al. |
| 2007/0239273 A1 | 10/2007 | Allen |
| 2007/0255398 A1 | 11/2007 | Yang et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0288089 A1 | 12/2007 | Gurskis et al. |
| 2008/0004696 A1 | 1/2008 | Vesely |
| 2008/0033543 A1 | 2/2008 | Gurskis et al. |
| 2008/0071361 A1 | 3/2008 | Tuval et al. |
| 2008/0071369 A1 | 3/2008 | Tuval et al. |
| 2008/0097595 A1 | 4/2008 | Gabbay |
| 2008/0109076 A1 | 5/2008 | Cartledge et al. |
| 2008/0119875 A1 | 5/2008 | Ino et al. |
| 2008/0281411 A1 | 11/2008 | Berreklouw |
| 2008/0319543 A1 | 12/2008 | Lane |
| 2009/0036903 A1 | 2/2009 | Ino et al. |
| 2009/0112233 A1 | 4/2009 | Xiao |
| 2009/0192599 A1 | 7/2009 | Lane et al. |
| 2009/0192602 A1 | 7/2009 | Kuehn |
| 2009/0192603 A1 | 7/2009 | Ryan |
| 2009/0192604 A1 | 7/2009 | Gloss |
| 2009/0192605 A1 | 7/2009 | Gloss et al. |
| 2009/0192606 A1 | 7/2009 | Gloss et al. |
| 2009/0210052 A1 | 8/2009 | Forster et al. |
| 2009/0264903 A1 | 10/2009 | Lee et al. |
| 2009/0319038 A1 | 12/2009 | Gurskis et al. |
| 2010/0030244 A1 | 2/2010 | Wolfson et al. |
| 2010/0044410 A1 | 2/2010 | Argentine et al. |
| 2010/0100174 A1 | 4/2010 | Gurskis |
| 2010/0249894 A1 | 9/2010 | Oba et al. |

(56) References Cited

U.S. PATENT DOCUMENTS

FOREIGN PATENT DOCUMENTS

| | | |
|---|---|---|
| EP | 0 084 395 B1 | 8/1986 |
| EP | 0 096 721 B1 | 12/1987 |
| EP | 0 125 393 B1 | 12/1987 |
| EP | 0 179 562 B1 | 7/1989 |
| EP | 0 826 340 A2 | 3/1998 |
| EP | 0 850 607 A1 | 7/1998 |
| EP | 1 057 460 A1 | 12/2000 |
| EP | 1 088 529 A2 | 4/2001 |
| EP | 1 171 059 A1 | 1/2002 |
| EP | 0 971 650 B1 | 1/2005 |
| EP | 1 171 059 B1 | 11/2005 |
| GB | 1093599 | 12/1967 |
| GB | 1477643 | 6/1977 |
| GB | 2011259 | 7/1979 |
| GB | 2 056 023 | 3/1981 |
| GB | 2 069 843 | 3/1981 |
| GB | 2 254 254 | 3/1992 |
| GB | 2 279 134 | 12/1994 |
| SU | 1116573 | 7/1985 |
| WO | WO 87/05489 A1 | 9/1987 |
| WO | WO 89/00084 A1 | 1/1989 |
| WO | WO 91/15167 A1 | 10/1991 |
| WO | WO 92/01269 A1 | 1/1992 |
| WO | WO 92/13502 A1 | 8/1992 |
| WO | WO 92/19184 A1 | 11/1992 |
| WO | WO 92/19185 A1 | 11/1992 |
| WO | WO 95/17139 A1 | 6/1995 |
| WO | WO 95/28899 A1 | 11/1995 |
| WO | WO 96/40006 A1 | 12/1996 |
| WO | WO 97/09933 A1 | 3/1997 |
| WO | WO 97/09944 A1 | 3/1997 |
| WO | WO 97/27779 A1 | 8/1997 |
| WO | WO 97/41801 A1 | 11/1997 |
| WO | WO 97/42871 A1 | 11/1997 |
| WO | WO 98/06329 A1 | 2/1998 |
| WO | WO 99/11201 A2 | 3/1999 |
| WO | WO 99/13802 A1 | 3/1999 |
| WO | WO 99/15112 A1 | 4/1999 |
| WO | WO 99/51169 A1 | 10/1999 |
| WO | WO 00/32105 A1 | 6/2000 |
| WO | WO 00/40176 A1 | 7/2000 |
| WO | WO 00/44311 A2 | 8/2000 |
| WO | WO 00/47139 A1 | 8/2000 |
| WO | WO 00/56250 A1 | 9/2000 |
| WO | WO 00/59382 A1 | 10/2000 |
| WO | WO 00/60995 A2 | 10/2000 |
| WO | WO 00/64380 A1 | 11/2000 |
| WO | WO 01/10310 A1 | 2/2001 |
| WO | WO 01/10312 A1 | 2/2001 |
| WO | WO 01/49217 A2 | 7/2001 |
| WO | WO 01/58363 A1 | 8/2001 |
| WO | WO 01/76510 A2 | 10/2001 |
| WO | WO 01/76510 A3 | 10/2001 |
| WO | WO 01/82840 A1 | 11/2001 |
| WO | WO 01/87190 A2 | 11/2001 |
| WO | WO 03/011195 A2 | 2/2003 |
| WO | WO 03/053289 A1 | 7/2003 |
| WO | WO 03/063740 A1 | 8/2003 |
| WO | WO 2004/006810 A1 | 1/2004 |
| WO | WO 2004/089246 A2 | 10/2004 |
| WO | WO 2005/004753 A1 | 1/2005 |
| WO | WO 2005/020842 A2 | 3/2005 |
| WO | WO 2005/039452 A1 | 5/2005 |
| WO | WO 2004/058106 A2 | 7/2005 |
| WO | WO 2005/072655 A1 | 8/2005 |
| WO | WO 2006/086135 A2 | 8/2006 |
| WO | WO 2009/137517 A1 | 11/2009 |

OTHER PUBLICATIONS

Lutter et al., "Percutaneous Valve Replacement: Current State and Future Prospects", Ann. Thorac. Surg., 78:2199-2206 (2004).

Tacson, "Prosthetic Heart Valves: Design Considerations" Ann. Thorac. Surgery, 48:516-517 (1989).

\* cited by examiner

NOT INVENTION

NOT INVENTION

NOT INVENTION

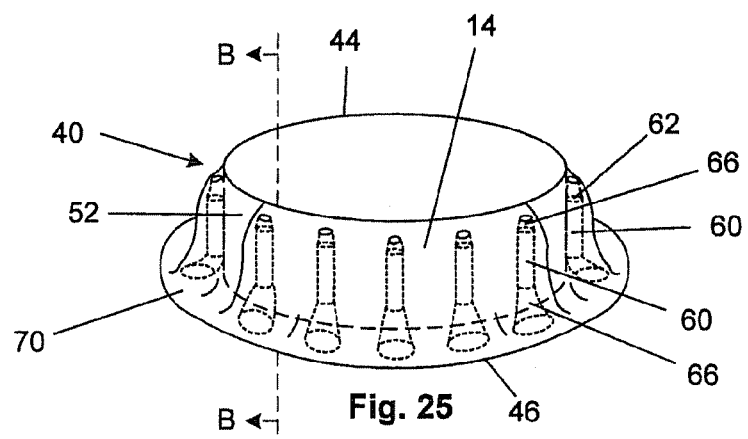
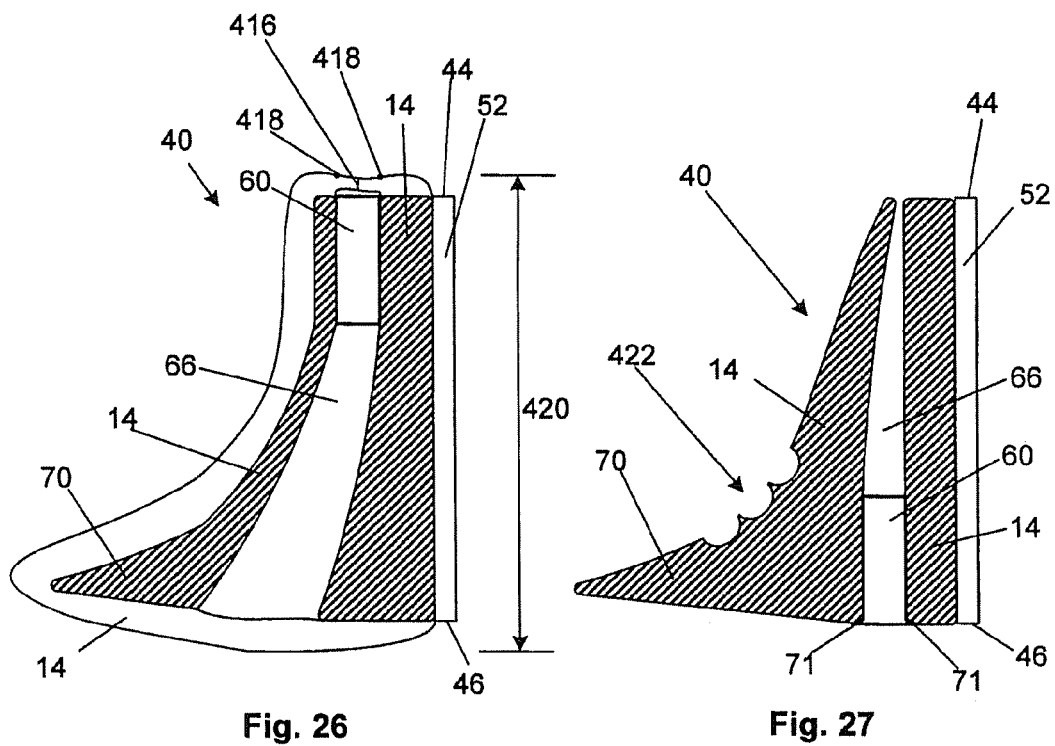
Fig. 25
Fig. 26
Fig. 27

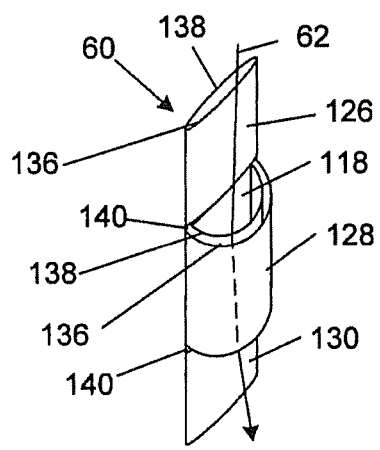
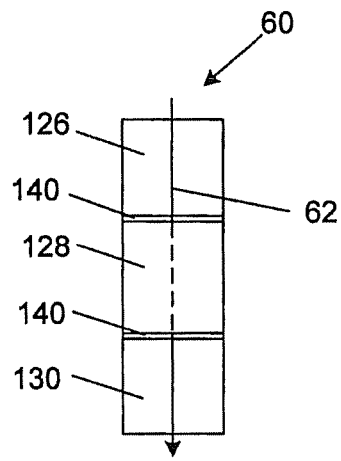
Fig. 39
Fig. 40
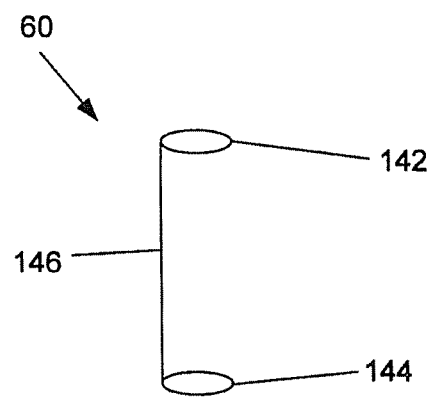
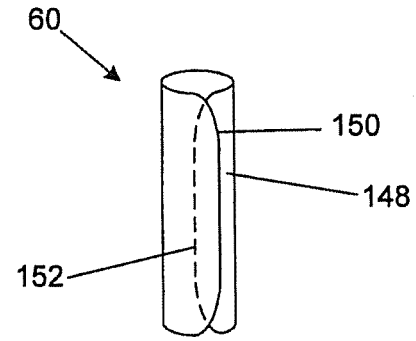
Fig. 41
Fig. 42

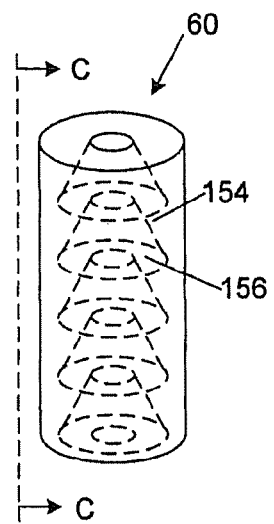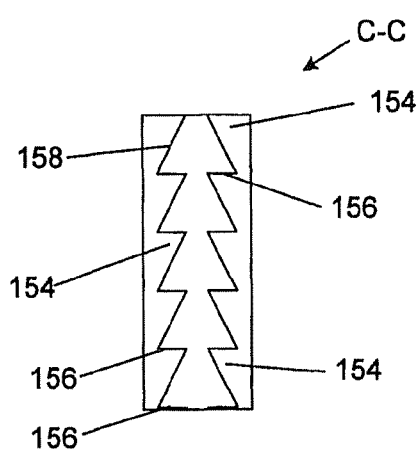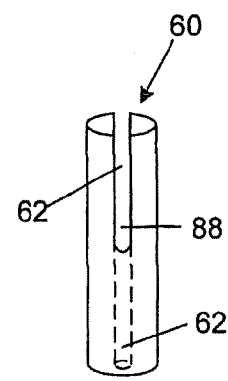
Fig. 49　　　　Fig. 50　　　　Fig. 51
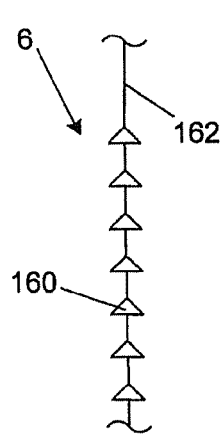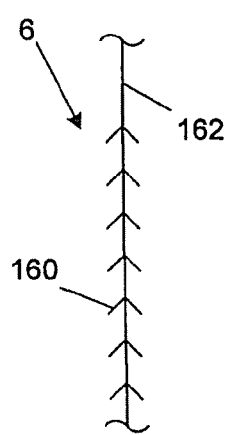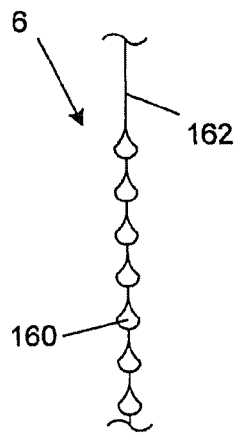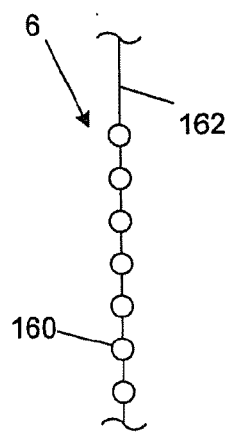
Fig. 52　　Fig. 53　　Fig. 54　　Fig. 55

US 8,747,463 B2

METHODS OF USING A PROSTHESIS FIXTURING DEVICE

CROSS-REFERENCE TO RELATED APPLICATIONS

This application is a divisional of U.S. application Ser. No. 10/646,639, filed Aug. 22, 2003, the contents of which are hereby incorporated by reference in their entirety.

BACKGROUND

1. Field of the Invention

The present invention relates generally to a device for fixturing a prosthesis to a first mass and methods of making and using the same.

2. Description of the Related Art

Prosthetic heart valves can replace defective human valves in patients. Prosthetic valves commonly include sewing rings or suture cuffs or rings that are attached to and extend around the outer circumference of the prosthetic valve orifice.

In a typical prosthetic valve implantation procedure, the aorta is incised and the defective valve is removed leaving the desired placement site that may include a fibrous tissue layer or annular tissue. Known heart valve replacement techniques include individually passing sutures through the fibrous tissue or desired placement site within the valve annulus to form an array of sutures. Free ends of the sutures are extended out of the thoracic cavity and laid, spaced apart, on the patient's body. The free ends of the sutures are then individually threaded through a flange of the sewing ring. Once all sutures have been run through the sewing ring (typically 12 to 18 sutures), all the sutures are pulled up taught and the prosthetic valve is slid or "parachuted" down into place adjacent the placement site tissue. The prosthetic valve is then secured in place by traditional knot tying with the sutures. This procedure is time consuming as doctors often use three to ten knots per suture.

The sewing ring is often made of a biocompatible fabric through which a needle and suture can pass. The prosthetic valves are typically attached to the sewing rings which are sutured to a biological mass that is left when the surgeon removes the existing valve from the patient's heart. The sutures are tied snugly, thereby securing the sewing ring to the biological mass and, in turn, the prosthetic valve to the heart.

FIG. 1 illustrates a valve prosthesis 2 fixed to a vessel 4 with sutures 6. The vessel 4 has a supra-annular space 8, an intra-annular or trans-annular space 10 and an infra-annular space 12. The natural valve that existed in the vessel has been removed. The placement site of the valve prosthesis 2 can be in the supra-annular space 8, an intra-annular or trans-annular space 10. The placement site is limited to being inferior to, and therefore not blocking, openings of the coronary arteries and superior to a plane defined by the insertion of the anterior leaflet of the mitral valve and the highest portion of the intraventricular septum. In the example shown in FIG. 1, the valve prosthesis 2 is on the shoulder between the supra-annular and trans-annular spaces 8 and 10. The valve prosthesis 2 has a sewing cuff or ring 14 that presses or rests against the supra-annular vessel wall.

FIG. 1 also illustrates two common types of suturing. On the left, the suture 6 can be fed into the vessel wall in the trans-annular or infra-annular space 10 or 12. The trailing end of the suture 6 can be secured to a pledget 16 by a knot 18 in the suture 6 behind the pledget 16. As illustrated in FIG. 2, the suture assembly consists of two curved needles 400 attached by a common length of suture 6. A pledget 16 is typically preloaded onto the suture 6. The pledget 16 braces the trailing end of the suture loop 6 against the vessel wall. The suture 6 then feeds through the vessel wall and exits the vessel wall in the supra-annular space 8. The surgeon passes the suture 6 through the sewing ring 14 and ties a knot 18 behind the sewing ring 14 to secure the sewing ring 14 to the vessel wall.

On the right side of FIG. 1, the suture 6 feeds into the vessel wall in the supra-annular space 8. The suture 6 is then attached to the pledget 16 and fed as described for the suture on the left side of FIG. 1. As the view of the vessel is often from the supra-annular or trans-annular space 8 or 10, this method provides the medical professional a better view of the initial insertion of the suture 6 into the vessel wall.

FIG. 3 illustrates a close-up of a mattress stitch of the suture 6. The two ends of the suture 6 feed separately through the same side of the pledget 16. Both ends of the suture 6 then feed into the vessel wall in the trans-annular or infra-annular space 10 or 12. The pledget 16 braces the suture 6 against the vessel wall. Both ends of the suture 6 then feed through the vessel wall and exit the vessel wall in the supra-annular space 8. Both ends of the suture 6 then pass through the sewing ring 14. The ends of the suture 6 are then tied to each other in the knot 18 behind the sewing ring 14, securing the sewing ring 14 to the vessel wall.

During heart valve replacement procedures, the patient is on heart-lung bypass which reduces the patient's oxygen level and creates non-physiologic bloodflow dynamics. The longer a patient is on heart-lung bypass, the greater the risk for complications including permanent health damage. Existing suturing techniques extend the duration of bypass and increase the health risks due to heart-lung bypass. Furthermore, the fixturing force created by suturing varies significantly because the pre-tensioning of the suture just prior to knot tying is difficult to consistently maintain, even for the same medical professional.

There is a need for a fixturing device to minimize the time required to fix a valve prosthesis to a first mass, which can be the surrounding tissue or a second prosthesis. There is also a need for a fixturing device to use a technique familiar to the users of existing devices. Furthermore, there is a need for a device that complements existing suturing devices and methods and reduces fixturing times. Also, there is a need for a fixturing device that does not require visual contact with, or suture access to, the infra-annular space. There also exists a need to provide a fixturing device that can provide a consistent fixturing force. The is also a need for a technique that could reduce the duration of the bypass procedure and minimize the associated health risks.

SUMMARY

A heart valve device is disclosed. The heart valve device has a gasket body and a receptacle located on an outer radial side of the gasket body. The receptacle can be, for example, a fenestration (e.g., window, gap, port, hole, slot), can, wireframe, hollow channel, collet, plate, eyelet, guide blocks, slide rod, guide blocks and slide rod with inner and outer walls or wall segments, high-friction channel, passage between cams, other complementary fixturing, or complementary attachment, device or other appropriate structure or any combination thereof. The receptacle is configured to receive an attachment or fixturing device. The attachment device can be knotless and the receptacle can have a friction lock. The friction lock can employ friction and/or an interference fit to fixedly attach the receptacle to the attachment device, for example, a plug or obstacles within a the receptacle. The receptacle can have a first cam, and the first cam can be rotatably attached to the gasket body. The receptacle can be in a flange. The flange can be an integral part of the gasket body, or the receptacle can be separate from, but attached to, the gasket body.

The receptacle can be formed into a cylinder. The cylinder can be a crimpable cylinder. The cylinder can be fixedly attached or rotatably attached to the gasket body. The cylinder can have a sidewall port or slit.

An attachment device for connecting a heart valve to a first mass is also disclosed. The attachment device has a base, a first connecting protrusion, and a second connecting protrusion. The base has a first side, a second side and a bendable joint. The first connecting protrusion is fixedly attached to the first side of the base at a first attachment area. The second connecting protrusion is fixedly attached to the first side of the base at a second attachment area.

The first connecting protrusion can be curved. The second connecting protrusion can be curved. The bendable joint can be between the first attachment area and the second attachment area. The bendable joint can be a fold in the base.

Another attachment device for connecting a heart valve to a first mass is also disclosed. This attachment device has a base and a curved shaft. The base has a sphere and a base diameter. The curved shaft has a first end, a second end and a shaft diameter. The first end is sharpened, and the second end is attached to the base. The base diameter is larger than the shaft diameter.

A heart valve is also disclosed. The heart valve has a gasket body, a first tab, and a second tab. The gasket body has a top surface and a bottom surface. The first tab is bendably attached to the top surface. The second tab is bendably attached to the bottom surface. The first tab can be pre-deployed in a bent position.

Another heart valve is disclosed. This heart valve has a gasket body and a first tab. The gasket body has a top surface, a bottom surface, and a middle area between the top surface and the bottom surface. The first tab is bendably attached to the middle area.

Another disclosed aspect is to use the disclosed devices to secure devices previously known to one having ordinary skill in the art, such as stents, grafts, stent-grafts, heart valves, annuloplasty rings and combinations thereof.

BRIEF DESCRIPTION OF THE DRAWINGS

FIGS. 22-25 illustrate various complementary fixturing devices on gasket bodies.

FIGS. 26 and 27 illustrate sections B-B of various embodiments of gasket bodies.

FIGS. 38-42 illustrate various complementary fixturing devices.

FIG. 49 illustrates a complementary fixturing device.

FIG. 50 illustrates section C-C.

FIG. 51 illustrates a complementary fixturing device.

FIGS. 52-55 illustrate various sutures.

DETAILED DESCRIPTION

Fixturing Devices

Figure 1:
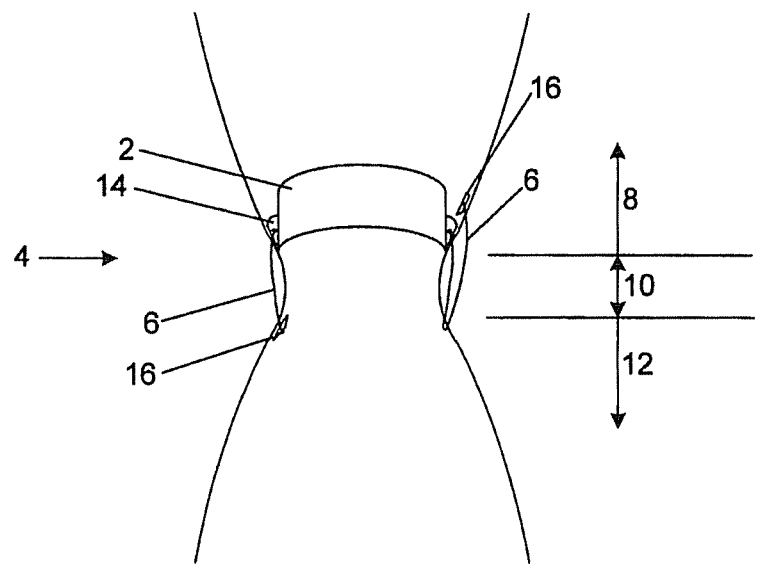
FIG. 1 is not the invention and illustrates a cut-away view of vessel having a heart valve ring with a sewing ring attached to a biological annulus.
Figure 2:
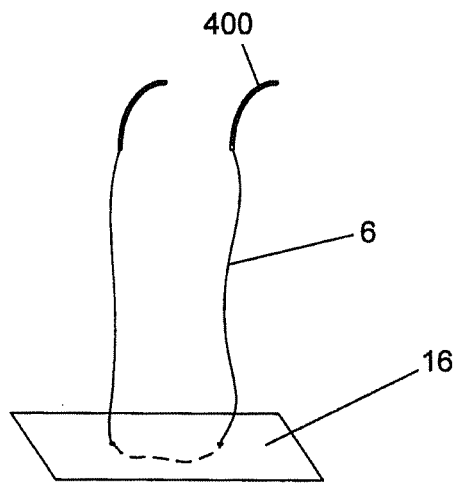
FIG. 2 is not the invention and illustrates a pledget and suture attached to two needles.
Figure 3:
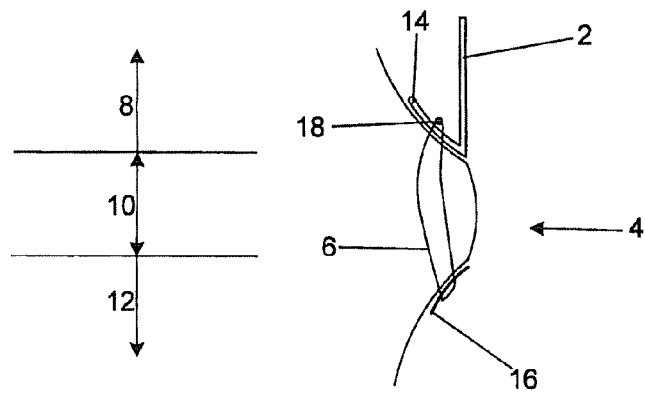
FIG. 3 is not the invention and illustrates a close-up view of a section of FIG. 1.
Figure 4:
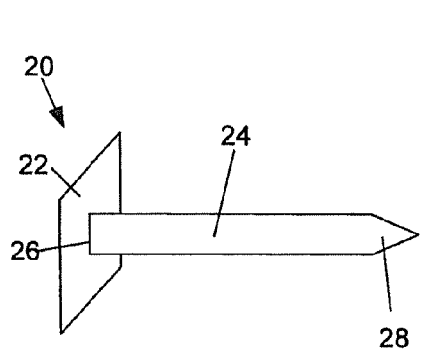
FIGS. 4 and 5 illustrate various fixturing devices.

FIG. 4 illustrates an attachment or fixturing device 20, for example a brad (e.g., single brad, double-brad, quadruple brad), stud, spike, staple, barb, hook or any combination thereof. The fixturing device 20 can have a base 22 and a connector, for example a connecting protrusion 24. The base 22 can be solid and/or substantially spherical. The base 22 can have a radially expandable portion, as described in U.S. patent application Ser. No. 10/327,821 filed 20 Dec. 2002, which is herein incorporated by reference in its entirety. The protrusion 24 can have a first end 26 and a second end 28. The first end 26 can be fixedly attached to the base 22. The second end 28 can be sharpened or pointed.

The fixturing device 20 can be used to attach a prosthesis to a first mass. The prosthesis can be, for example, stents, grafts, stent-grafts, heart valves, annuloplasty rings autografts, allografts, xenografts or any combination thereof. The first mass can be, for example, tissues such as vessels, valves, organs (e.g., intestine, heart, skin, liver, kidney) or any combination thereof.

Figure 5:
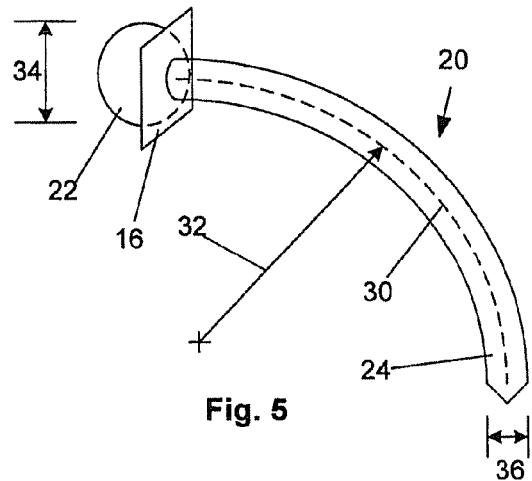

FIG. 5 illustrates the fixturing device 20 having a protrusion 24 that can be curved. The protrusion 24 can have a center line 30. The center line 30 can have a radius of curvature 32. The base 22 can have a base diameter 34. The base 22 can be configured to be a substantially flat square, rectangular, circular or ellipse, or a sphere, cylinder or cube. The protrusion 24 can be configured to be flat, square, or cylindrical, and can be straight, curved or angled. The protrusion 24 can have a protrusion diameter 36. The fixturing device 20 can have a pledget 16 slidably or fixedly attached to the protrusion 24 near or against the base 22. The pledget 16 can be fixedly or rotatably attached to the base 22.

The fixturing device 20 can be made from stainless steel alloys, nickel titanium alloys (e.g., Nitinol), cobalt-chrome alloys (e.g., ELGILOY® from Elgin Specialty Metals, Elgin, Ill.; CONICHROME® from Carpenter Metals Corp., Wyomissing, Pa.), polymers such as polyester (e.g., DACRON® from E. I. Du Pont de Nemours and Company, Wilmington, Del.), polypropylene, polytetrafluoroethylene (PTFE), expanded PTFE (ePTFE), polyether ether ketone (PEEK), nylon, polyether-block co-polyamide polymers (e.g., PEBAX® from ATOFINA, Paris, France), aliphatic polyether polyurethanes (e.g., TECOFLEX® from Thermedics Polymer Products, Wilmington, Mass.), polyvinyl chloride (PVC), polyurethane, thermoplastic, fluorinated ethylene propylene (FEP), extruded collagen, silicone, radiopaque materials or combinations thereof. Examples of radiopaque materials are barium sulfate, titanium, stainless steel, nickel-titanium alloys, tantalum and gold.

Figure 6:
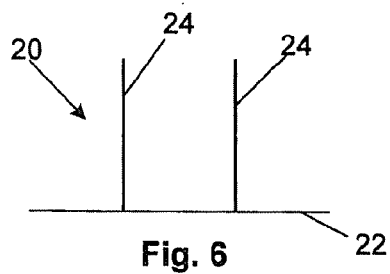
FIGS. 6 and 7 illustrate top views of various fixturing devices.
Figure 7:
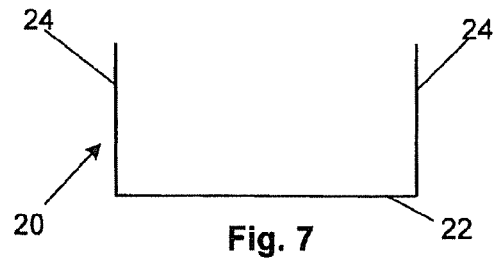
Figure 8:
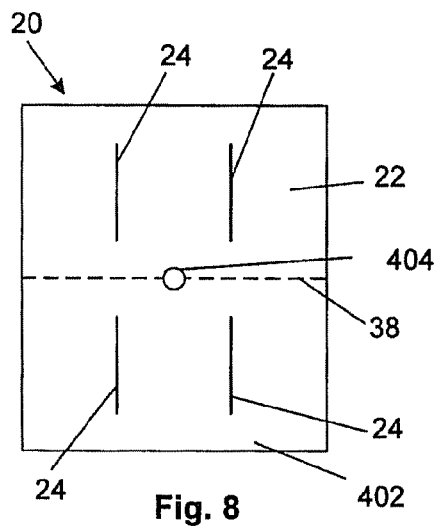
FIGS. 8 and 9 illustrate front views of FIGS. 6 and 7, respectively.
Figure 9:
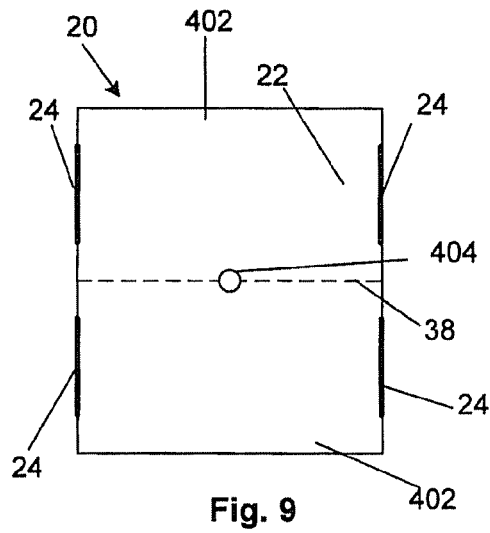

The fixturing device 20 can have multiple connectors, for example the protrusions 24, as illustrated in FIGS. 6-11. The protrusions 24 can be aligned with one another. The protrusions 24 can be deformable or non-deformable. The fixturing device 20 can have four protrusions 24, where two protrusions 24 are on each side of a joint, for example a straight bendable fold 38 in the base 22, a thinned and/or annealed portion of the base 22, a mechanical hinge in the base 22 or combinations thereof. The protrusions 24 can be attached to the outer edge of the base 22, as shown in FIGS. 7 and 9. The protrusions 24 of FIGS. 7 and 9 can be cut from the same piece of material as the base 22, and deformably folded into position. The protrusions 24 can be attached to base 22 away from the outer edge of the base 22, as shown in FIGS. 6 and 8.

The base 22 can extend away from the fold 38 and beyond the protrusions 24 to form a retention pad 402. An alignment hole 404 can be formed in the base 22, for example in the middle of the base 22 along the fold 38, to align a deployment tool or applicator assembly with the fixturing device 20.

Figure 10:
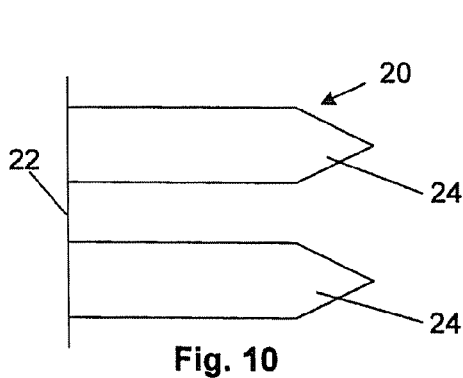
FIGS. 10 and 11 illustrate side views of various embodiments of the devices of FIGS. 6-9.
Figure 11:
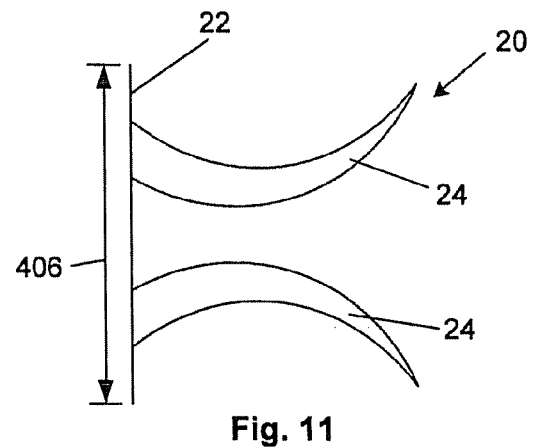

FIG. 10 illustrates protrusions 24 that can be substantially straight. FIG. 11 illustrates protrusions 24 that can be substantially sickle or scimitar-shaped. The base 22 can have a base height 406. The base height 406 can be from about 1.27 mm (0.050 in.) to about 12.7 mm (0.500 in.), for example about 3.18 mm (0.125 in.).

Prostheses

Figure 12:
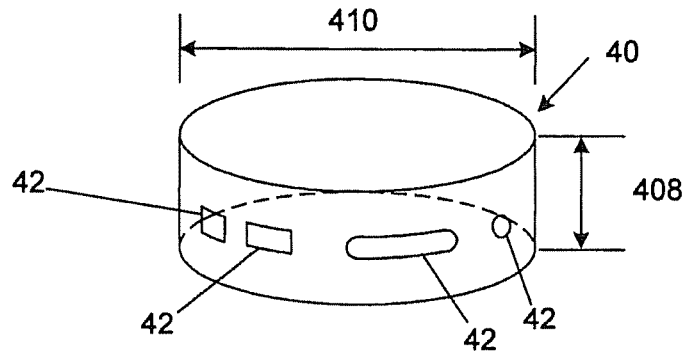
FIG. 12 illustrates various fenestrations on a gasket body.

FIG. 12 illustrates a heart valve gasket body 40, for example a ring, that can have various openings, receptacles or windows 42. The windows 42 can be configured, for example, as squares, rectangles, ovals or circles. The windows 42 can all be the same shape or the windows 42 can be different shapes. The gasket body 40 can be any configuration conforming to the annulus shape of the patient, including a shape conforming to irregularities (e.g., a lobular annulus). The gasket body 40 can be, for example, circular, ovular, elliptical, bi-lobular or tri-lobular. The gasket body 40 can have any of the features of the device described in U.S. patent application Ser. No. 10/327,821 filed 20 Dec. 2002. The gasket body 40 can be made from any of the materials listed supra for the fixturing device 20 or combinations thereof. The gasket body 40 can be flexible and/or rigid. The gasket body 40 can have a gasket height 408 and a gasket diameter 410. The gasket height 408 can be from about the length between the openings of the coronary arteries and the closest point on a plane defined by the insertion of the anterior leaflet of the mitral valve and the highest portion of the intraventricular septum to about 12.7 mm (0.500 in.), for example 5.08 mm (0.200 in.). The gasket diameter 410 can be from about 10 mm (0.39 in.) to about 50 mm (2.0 in.), more narrowly from about 30 mm (1.2 in.) to about 40 mm (1.6 in.).

Figure 13:
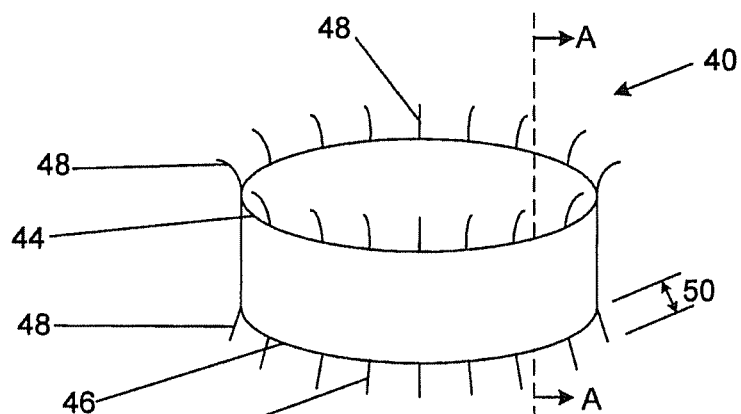
FIG. 13 illustrates tabs on a gasket body.

FIG. 13 illustrates a gasket body 40 that can have a top edge or side 44 and a bottom edge or side 46. Tines, prongs or tabs 48 can be attached to the top and/or bottom edges 44 and/or 46. The tabs 48 can have a tab length 50. The tab length 50 can be sufficiently sized to mechanically engage the annular tissue without damaging other organs or tissues (e.g., ventricles).

Figure 14:
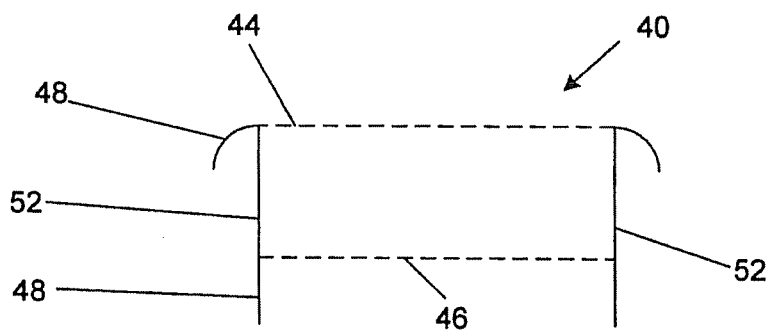
FIG. 14 illustrates an embodiment of section A-A.

FIG. 14 illustrates cross-section A-A of the gasket body 40 that can have pre-deployed tabs 48 attached to the top edge 44. The tabs 48 attached to the top edge 44 can extend substantially perpendicular from a wall 52 of the gasket body 40. The tabs 48 attached to the top edge 44 can point radially outward and/or downward. The tabs 48 attached to the bottom edge 46 can extend substantially parallel from a wall 52 of the gasket body 40. The tabs 48 attached to the bottom edge 46 can point straight downward or be angled radially inward or outward.

Figure 15:
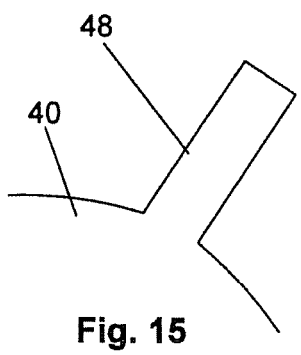
FIGS. 15-20 illustrate various tabs.
Figure 16:
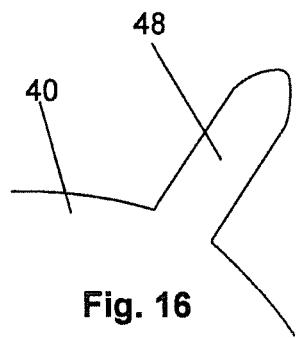
Figure 17:
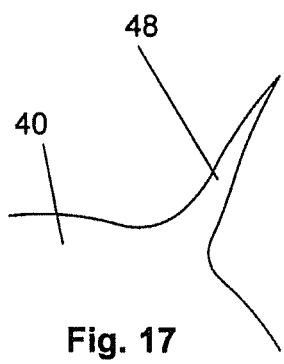
Figure 18:
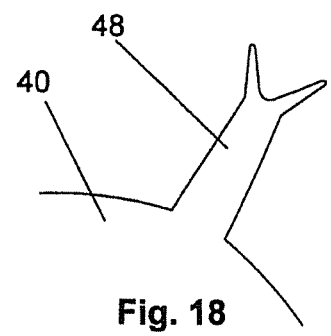
Figure 19:
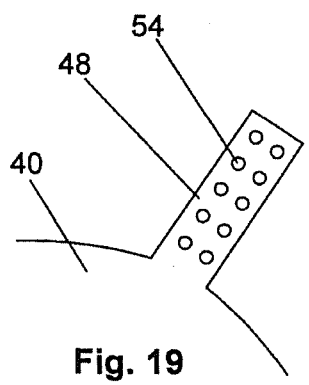
Figure 20:
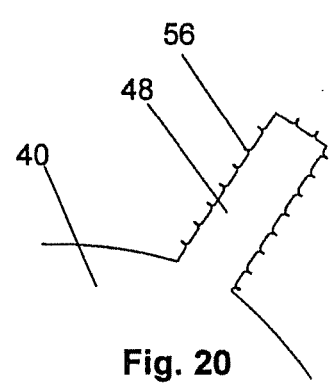

FIG. 15 illustrates the tab 48 that can have a rectangular configuration. FIG. 16 illustrates the tab 48 that can have a rounded configuration. FIG. 17 illustrates the tab 48 that can have a sharp spiked configuration. FIG. 18 illustrates the tab 48 that can have a forked, "V"-shaped, or "Y"-shaped configuration. FIG. 19 illustrates the tab 48 that can have pores or holes 54. FIG. 20 illustrates the tab 48 that can have micro-engagement devices, for example studs, spikes, hooks and/or barbs 56. Any of the aforementioned tab configurations and elements can be used in combination.

Figure 21:
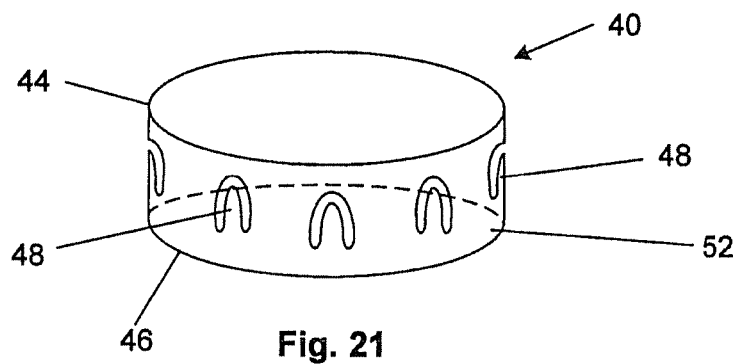
FIG. 21 illustrates tabs on a gasket body.

FIG. 21 illustrates the gasket body 40 that can have tabs 48 between the top edge 44 and the bottom edge 46. The tabs 48 can be substantially deformable sections of the wall 52 of the gasket body 40.

Figure 22:
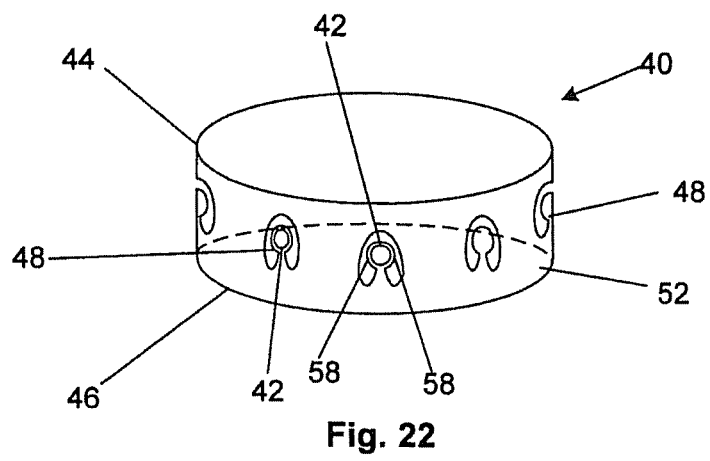

FIG. 22 illustrates the gasket body 40 that can have tabs 48 with side wings 58 extending from the sides of the tabs 48. The tabs 48 can be between the top edge 44 and the bottom edge 46 and/or the tabs 48 can be at the top edge 44, and/or the tabs can be at the bottom edge 46. The side wings 58 can be substantially deformable sections of the wall 52 of the gasket body 40. Some, none or all of the tabs 48 can have receptacles or windows 42 therein, thereby enabling the tabs 48 to function as deformable receptacles or windows 42.

Figure 23:
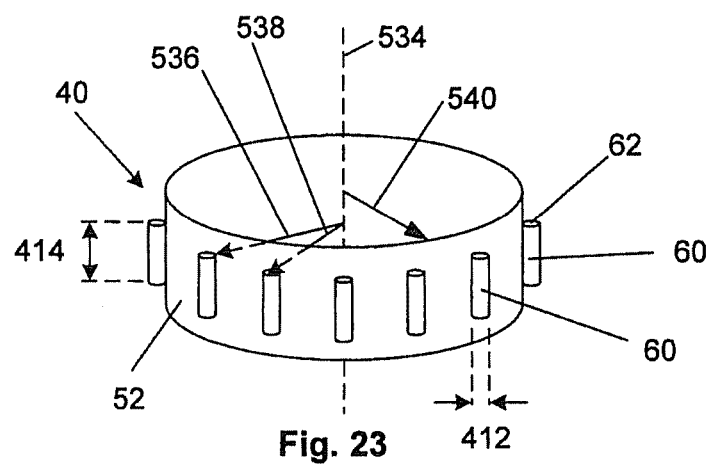

FIG. 23 illustrates the gasket body 40 that can have cooperative or complementary fixturing (or attachment) devices, for example receptacles, such as fiction-lock or mechanical interference-lock devices, configured to receive a fixturing device, for example the suture 6 (suture 6 refers herein to sutures 6 and other similar attachment mechanisms). Cooperative or complementary fixturing devices are devices or features that engage the fixturing device and assist the fixturing device to fix or attach to the prosthesis, for example the gasket body. The suture 6 can be 2-0 suture, 0 suture, another suture known to one having ordinary skill in the art or any combinations thereof. The receptacles can be discrete, meaning that each receptacle can be not directly connected to other receptacles. The receptacle can be, for example, cans 60 such as deformable cylinders. ("Can" 60 refers to cylinders and non-cylinders throughout the specification.) The can 60 can be annealed or otherwise treated to make the can 60 more easily deformable. The can 60 can have a can diameter 412 and a can height 414. The inner can diameter 412 can be from about 0.838 mm (0.033 in.) or to about 2.54 mm (0.100 in), for example about 0.838 mm (0.033 in.). The outer can diameter 412 can be from about 1.3 mm (0.050 in.) to about 3.18 mm (0.125 in), for example about 1.3 mm (0.050 in). The can height 414 can be from about 1.3 mm (0.050 in.) to about 6.35 mm (0.250 in.), for example about 3.18 mm (0.125 in.).

Each can 60 can have a hollow channel 62. The hollow channel 62 can be on the inside and/or outside of the can 60. The hollow channel 62 can be a path for the suture 6. The complementary fixturing devices can be attached to the outer radial side (as shown in FIG. 22), inner radial side or within the wall 52 of the gasket body 40. The complementary fixturing devices and their associated parts can be made from any of the same materials listed above for the fixturing device 20.

The gasket body 40 can have a gasket longitudinal axis 534 through the center of the gasket body 40. An inner complementary attachment device radius 536 can be measured from the gasket longitudinal axis 534 to the closest part of the can 60 from the gasket longitudinal axis 534. An outer complementary attachment device radius 538 can be measured from the gasket longitudinal axis 534 to the farthest part of the can 60 from the gasket longitudinal axis 534. A gasket body radius 540 can extend from the gasket longitudinal axis 534 to the gasket body 40. Inner and outer gasket body radii (not shown) can be measured from the gasket body radius 540 to the closest and farthest parts, respectively, of the gasket body 40 from the gasket longitudinal axis 534.

When the outer complementary attachment device radius 538 is greater than the outer gasket body radius 540, the inner complementary attachment device radius 536 can be greater than, about equal to or less than the outer gasket body radius 540, or the inner complementary attachment device radius 536 can be greater than, about equal to or less than the inner gasket body radius 540. When the outer complementary attachment device radius 538 is less than the outer gasket body radius 540 (when the can 60 is on the radial inside of the gasket body 40), the inner complementary attachment device radius 536 can be greater than, about equal to or less than the outer gasket body radius 540, or the inner complementary attachment device radius 536 can be greater than, about equal to or less than the inner gasket body radius 540.

Figure 24:
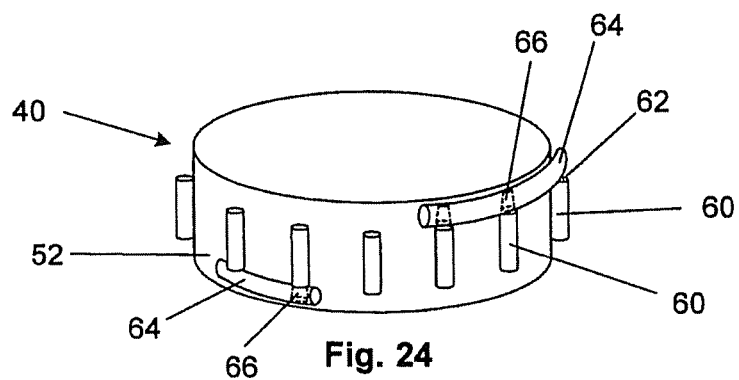

FIG. 24 illustrates the gasket body 40 of FIG. 23 that can have flanges 64, for example soft pads. The flanges 64 can partially and/or completely circumferentially surrounding the gasket body 40. The flanges 64 can be solid or porous. The flanges 64 can be fabric, for example, polyester (e.g., DACRON® from E. I. du Pont de Nemours and Company, Wilmington, Del.), polypropylene, PTFE, ePTFE, nylon, extruded collagen, silicone or combinations thereof The flanges 64 can be a matrix for cell ingrowth during use. The flanges 64 and/or any other parts of the invention can be filled and/or coated with an agent delivery matrix known to one having ordinary skill in the art and/or a therapeutic and/or diagnostic agent. These agents can include radioactive materials; radiopaque materials; cytogenic agents; cytotoxic agents; cytostatic agents; thrombogenic agents, for example polyurethane, cellulose acetate polymer mixed with bismuth trioxide, and ethylene vinyl alcohol; lubricious, hydrophilic materials; phosphor cholene; anti-inflammatory agents, for example non-steroidal anti-inflammatories (NSAIDs) such as cyclooxygenase-1 (COX-1) inhibitors (e.g., acetylsalicylic acid, for example ASPIRIN® from Bayer AG, Leverkusen, Germany; ibuprofen, for example ADVIL® from Wyeth, Collegeville, Pa.; indomethacin; mefenamic acid), COX-2 inhibitors (e.g., VIOXX® from Merck & Co., Inc., Whitehouse Station, N.J.; CELEBREX® from Pharmacia Corp., Peapack, N.J.; COX-1 inhibitors); immunosuppressive agents, for example Sirolimus (RAPAMUNE®, from Wyeth, Collegeville, Pa.), or matrix metalloproteinase (MMP) inhibitors (e.g., tetracycline and tetracycline derivatives) that act early within the pathways of an inflammatory response. Examples of other agents are provided in Walton et al, Inhibition of Prostoglandin $E_2$ Synthesis in Abdominal Aortic Aneurysms, *Circulation*, Jul. 6, 1999, 48-54; Tambiah et al, Provocation of Experimental Aortic Inflammation Mediators and Chlamydia Pneurnoniae, *Brit. J Surgery* 88 (7), 935-940; Franklin et al, Uptake of Tetracycline by Aortic Aneurysm Wall and Its Effect on Inflammation and Proteolysis, *Brit. J Surgery* 86 (6), 771-775; Xu et al, Sp1 Increases Expression of Cyclooxygenase-2 in Hypoxic Vascular Endothelium, *J. Biological Chemistry* 275 (32) 24583-24589; and Pyo et al, Targeted Gene Disruption of Matrix Metalloproteinase-9 (Gelatinase B) Suppresses Development of Experimental Abdominal Aortic Aneurysms, *J. Clinical Investigation* 105 (11), 1641-1649 which are all incorporated by reference in their entireties.

The flanges 64 can have a circular, oval or square cross-section. The flanges 64 can be attached to the wall 52 and/or to the cans 60. The flanges 64 can be above and/or below the cans 60. The flanges 64 can cover sharp edges exposed on the gasket body 40, cans 60 or other parts. The flanges 64 can surround the perimeter of the gasket body 40 and/or can be in a segment or segments (as shown) that do not surround the perimeter of the gasket body 40. The flanges 64 can have cannulated suture ports 66 that can be aligned with the cans 60 and/or no suture port can be aligned with the cans 60. The cans 60 can be partially or completely inside the flanges 64. A suture for a specific can 60 can be passed through a suture port 66, and/or through and/or around the flange 64 during use FIG. 25 illustrates the gasket body 40 that can be surrounded by a flange configured as sewing ring 14. The sewing ring 14 can be solid or porous. The sewing ring 14 can be fabric and can be made from any material listed above for the flanges 64. The sewing ring 14 can be a matrix for cell ingrowth during use.

The sewing ring 14 can be attached to the wall 52 and/or to the cans 60. The sewing ring 14 can extend from about the bottom edge 46 to about the top edge 44. The sewing ring 14 can cover exposed edges and/or metal on the gasket body 40, cans 60 or other parts. The sewing ring 14 can surround the perimeter (as shown in FIG. 25) of the gasket body 40 and/or can be in a segment or segments that do not surround the perimeter of the gasket body 40. The sewing ring 14 can have cannulated suture ports 66 that can be aligned with the cans 60 and/or no suture port can be aligned with the cans 60. A suture for a specific can 60 can be passed through an access or suture port 66, and/or through and/or around the sewing ring 14 during use. The access or suture port 66 can be pre-formed, before deployment of the gasket body 40. The gasket body 40 can have the sewing ring 14 and can be devoid of cans 60.

The sewing ring 14 can incorporate a flare or skirt 70. The skirt 70 can surround the perimeter (as shown) of the sewing ring 14 or can be in a segment or segments that do not surround the perimeter of the sewing ring 14. The skirt 70 can extend radially from the sewing ring 14. The skirt 70 can be placed near or at the bottom edge 46.

FIG. 26 illustrates an embodiment of cross-section B-B. The can 60 can be within the sewing ring 14. The can 60 can be placed near or at the top edge 44. The suture port 66 can stay the same size or enlarge as the suture port 66 extends away from the can 60. The sewing ring 14 can close over the suture port 66. The sewing ring can form an eyelet, buttonhole or gusset 416 adjacent to the suture port 66. The gusset 416 can be self-closing. The sewing ring 14 can have a reinforcement 418 that can encircle the gusset 416. The reinforcement 418 can be made of any of the materials listed herein, for example a metal or plastic ring. The reinforcement 418 can also be a thickened or additionally dense portion of the material of the sewing ring 14.

FIG. 27 illustrates an embodiment of cross-section B-B. The sewing ring 14 can have a sewing ring height 420. The can height 414 can be less than, equal to, or greater than the sewing ring height 420. The sewing ring height 420 can be from about 1.3 mm (0.050 in.) to about 6.35 mm (0.250 in.), for example about 3.18 mm (0.125 in.), also for example about 5.08 mm (0.200 in.), for another example about 6.35 mm (0.250 in.). The can 60 can be placed near of at the bottom edge 46. The cross-section of the suture port 66 can enlarge, stay the same, or reduce in size as the suture port 66 extends away from the can 60. The can 60 can have attachment prongs 71. The can 60 can be attached to the sewing ring 14 at the attachment prongs 71 or by other attachment methods known in the art, for example by suturing methods known in the art. The outer radial side of the skirt 70 or the remainder of the sewing ring 14 can be shaped, sized, coated, otherwise treated or any combination thereof to alter the stiffness as desired. For example, the skirt 70 can have relief grooves 422 formed therein. The relief grooves 422 can be semicircular, rectangular, semi-oval, star-shaped or a combination thereof.

The sewing ring 14 can suspend the cans 60 from the gasket body 40. The cans 60 can rotate and translate with a reduced resistance from the gasket body 40 thereby allowing snug fixturing of the gasket body 40 to the first mass without unnecessary deformation of the annulus by the wall 52.

Figure 28:
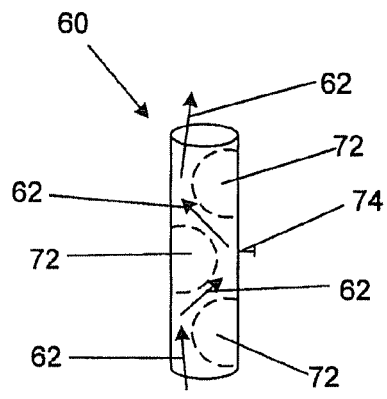
FIGS. 28-36 illustrate various complementary fixturing devices.

FIG. 28 illustrates the can 60 adapted to receive a suture 6, snare or other element for fixation. The can 60 can have passive internal obstacles, for example offset internal obstacles 72, defining a hollow channel 62 that can have a tortuous path within the can 60. The internal obstacles 72 can be made from a polymer that can provide increased friction against the suture 6 compared to the friction from the can 60. The internal obstacles 72 can be made from any of the materials listed herein for any other elements or any combination thereof. The can 60 can be fixedly or rotatably attached to an axle 74.

Figure 29:
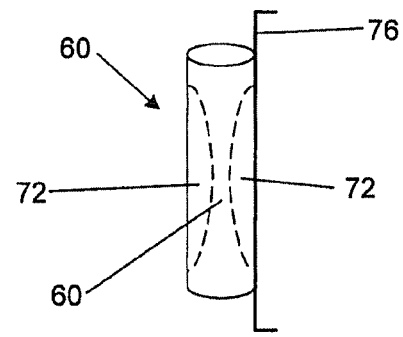

FIG. 29 illustrates the can 60 that can have aligned internal obstacles 72. The can 60 can be fixedly or rotatably attached to a frame 76. The internal obstacles 72 can be configured to collapse or crush when the can 60 is crushed, for example, the internal obstacles 72 can be hollow.

Figure 30:
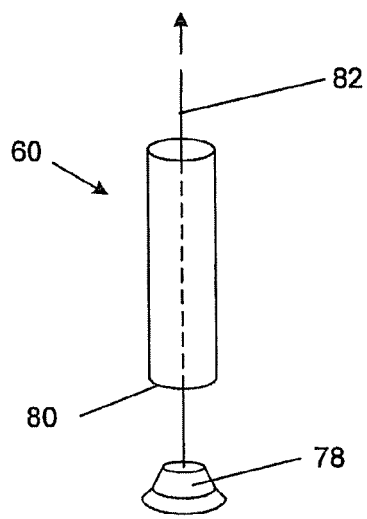

FIG. 30 illustrates a can 60 and an elastic space-occupying element, for example a plug 78, sized to sealingly fit a can end 80. The space-occupying element can be made of, for example, an elastomer and/or any of the other materials listed herein for any other elements or any combination thereof. The plug 78 can be removably attached to an engagement element, for example a breakaway line 82. The breakaway line 82 can be pulled (as shown by the arrow) through the can 60 to engage and fix the plug 78 in the can end 80. The breakaway line 82 can be configured to separate from the plug 78 when a maximum tension is exceeded. The plug 78 can be engaged and fixed into the other can end 80. Two space-occupying elements can be used, one space-occupying element for each can end 80. The space-occupying elements can be self-engaging, engaging and fixing into the can end 80 when the suture 6 is deployed and/or pulled through and/or near the space-occupying element.

Figure 31:
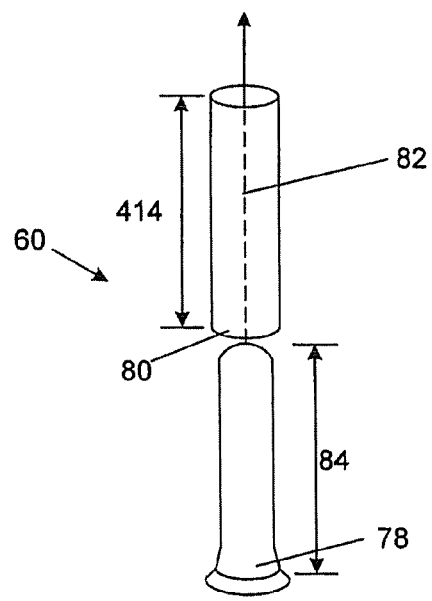

FIG. 31 illustrates a can 60 and a plug 78 sized to fit the can end 80. The plug can have a plug height 84. The plug height 84 can be from about 1.3 mm (0.050 in.) to about 6.35 mm (0.250 in.), for example about 3.18 mm (0.125 in.). The plug height 84 can be substantially equal to the can height 414 or sized to sufficiently engage the suture 6 against the can 60. The insertion force that pushes the plug 78 into the can 60 can be from about enough to secure the plug 78 in the can 60 to about equal to the retention force securing the gasket body 40 to the implantation site. For example, for the can 60 having an inner can diameter 412 of about 8.4 mm (0.33 in.), the insertion force for the plug 78 having a diameter of about 0.64 mm (0.025 in.) can be about 11 N (2.5 lbs.). In another example, for the can 60 having an inner can diameter 412 of about 8.4 mm (0.33 in.), the insertion force for the plug 78 having a diameter of about 0.66 mm (0.026 in.) can be about 19 N (4.3 lbs.).

Figure 32:
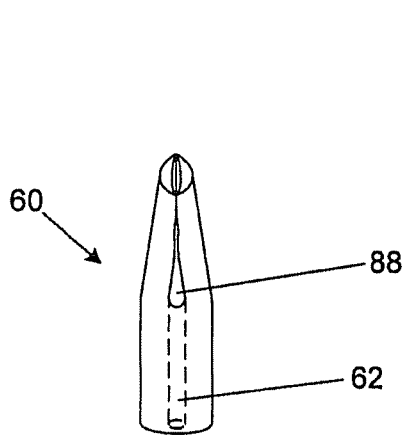

FIG. 32 illustrates a resilient can 60 that can be biased to remain closed. The can 60 can be made from a resilient material, for example, a polymer, any other materials listed herein or any combinations thereof. The can 60 can have slots 88 in the sides of the can 60.

Figure 33:
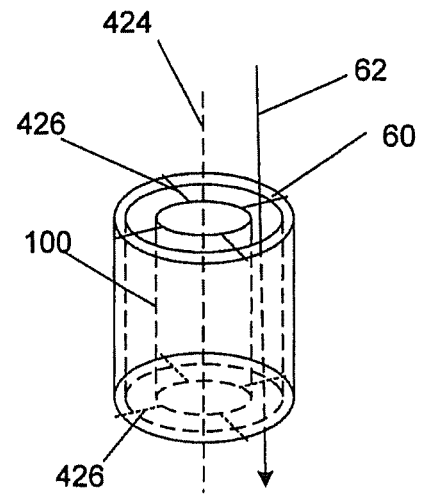

FIG. 33 illustrates a can 60 that can have an active internal obstacle, for example an expandable obstacle 100. The expandable obstacle 100 can be, for example, a deformably expandable (e.g., balloon-expandable) or resiliently-expandable (e.g., self-expandable) space-occupying element, such as a deformable cylinder, stent or balloon. The hollow channel 62 can be between the expandable obstacle 100 and the can 60. The hollow channel 62 can form an annular space for passing the suture 6. The can 60 can have a can longitudinal axis 424. The expandable obstacle 100 or the can 60 can have longitudinally-retaining members 426 at either or both ends that extend perpendicularly to the can longitudinal axis 424 and longitudinally restrain the expandable obstacle 100 with respect to the can 60.

The can 60 can also be radially compressible and the obstacle 100 can be radially non-compressible. During use, the can 60 can compress onto the obstacle 100.

Figure 34:
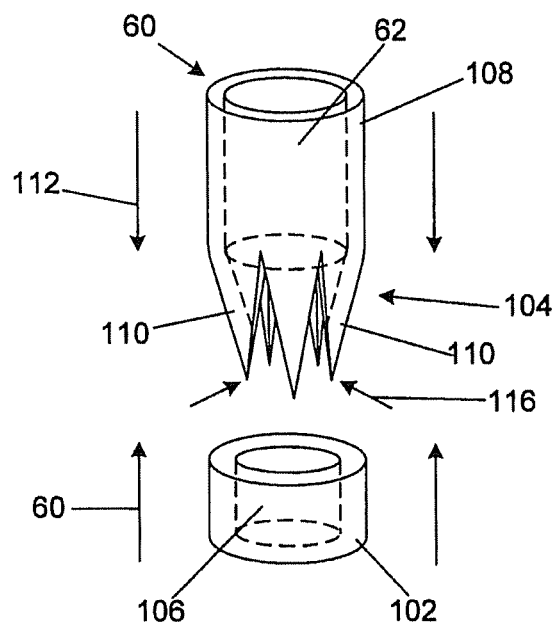

FIG. 34 illustrates a collet 102 and a can 60 that can have a splayed end 104. The collet 102 can have a can port 106 sized to receive the splayed end 104. The can 60 can have a can body 108 and extensions 110 at the splayed end 104. The extensions 110 can be resiliently or deformably attached to the can body 108. The extensions 110 can be biased radially inward as the extensions 110 extend away from the can body 108. During use, the can 60 can be moved toward the collet 102, shown by arrows 112, and/or the collet 102 can be moved toward the can 60, shown by arrows 114. The splayed end 104 can move into the can port 106 and continue to move through the can port 106 until the splayed end 104 radially contracts, shown by arrows 116, to a desired position.

Figure 35:
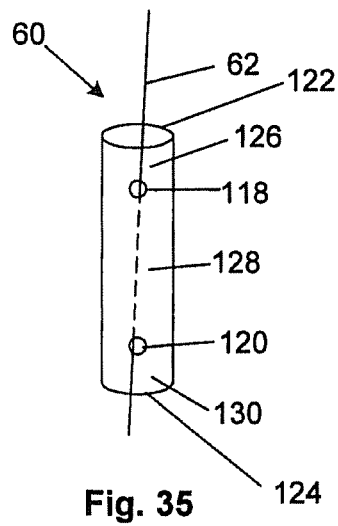

FIG. 35 illustrates the can 60 that can have a first fenestration or window 118 and a second fenestration or window 120. The can 60 can have a first can end 122 nearer the first window 118. The can 60 can have a second can end 124 nearer the second window 120. The can 60 can have a first can segment 126 between the first can end 122 and the first window 118. The can 60 can have a second can segment 128 between the first window 118 and the second window 120. The can 60 can have a third can segment 130 between the second window 120 and the second can end 124.

The hollow channel 62 can be outside the radius of the can 60 in the area of the first can segment 126. The hollow channel 62 can pass through the first can window. The hollow channel 62 can be inside the radius of the can 60 in the area of the second can segment 128. The hollow channel 62 can pass through the second window 120. The hollow channel 62 can be outside the radius of the can 60 in the area of the third can segment 130.

The hollow channel 62 can pass into, and/or out of, the radius of the can 60 in any combination for the first, second, and third can segments 126, 128 and 130. The hollow channel 62 does not have to pass through a fenestration or window when the hollow channel 62 goes from one can segment to an adjacent can segment.

Figure 36:
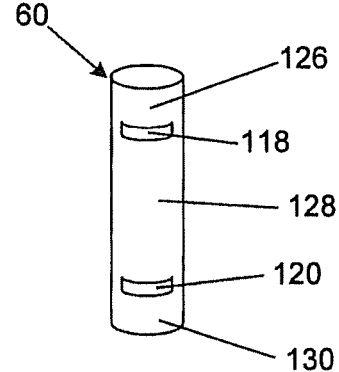
Figure 37:
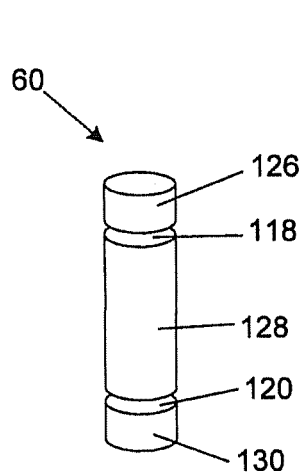
FIG. 37 is a front view of the complementary fixturing device of FIG. 36.

The first and second windows 118 and 120 can be circular, as shown in FIG. 35, rectangular, as shown in FIG. 36, ovular, square or combinations thereof. The windows can also have an angular width up to about 360°, as shown in FIG. 37. If the angular width of the windows 118 and/or 120 is 360° the can segments 126, 128, and 130 can be completely separated from each other.

Figure 38:
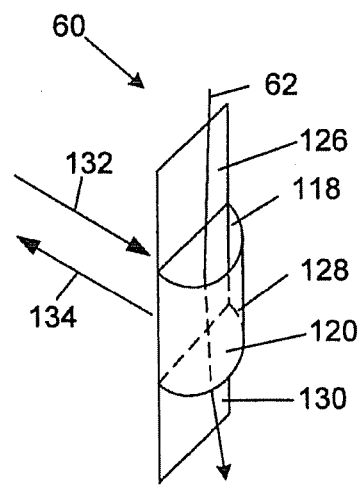

FIG. 38 illustrates the can 60 that can have the first can segment 126 and the third can segment 130 that can be substantially misaligned with the second can segment 128. For example, the first and third can segments 126 and 130 can be substantially flat. The second can segment 128 can be curved, for example, in a semi-circular shape.

A first direction 132 can be substantially opposite of a second direction 134. The hollow channel 62 can pass on the first direction side of the first can segment 126. The hollow channel 62 can pass through the first window 118. The hollow channel 62 can pass on the second direction side of the second can segment 128. The hollow channel 62 can pass through the second window 120. The hollow channel 62 can pass on the first direction side of the third can segment 130.

FIGS. 39 and 40 illustrate the can 60 that can be a cylinder that has been crushed into a shape analogous to the shape of the can 60 shown in FIG. 38. The can 60 can have front panels 136 and rear panels 138. The can 60 can have a gaps 140 between the can segments 126, 128 and 130. The gaps 140 can be formed by removing a portion of the panels 136 and/or 138 next to the adjacent can segment 126, 128 or 130. For example, a portion of the front panel 136 on the first and/or third can segments 126 and/or 130 can be removed, and/or a portion or portions of the rear panel 138 on the second can segment 128 can be removed. During use, the gaps 140 can reduce the shearing force applied to the suture 6 passed through the hollow channel 62 if the second can segment 128 is pressed into a position substantially parallel to the first and/or third can segments 126 and/or 130.

FIG. 41 illustrates a can 60 that can be made from a wire or wires. The wire or wires can be deformable or resilient. The can 60 can have a first loop 142, a second loop 144 and a chassis 146. The first loop 142 can be fixedly attached to the chassis 146. The second loop 144 can be fixedly attached to the chassis 146. Additional loops can be attached to the chassis 146. The chassis 146 can be a single wire between the first loop 142 and the second loop 144.

FIG. 42 illustrates a can 60 that can be made from a plate 148. The plate 148 can be formed, for example by wrapping or otherwise hot or cold forming, into a substantially cylindrical shape. A first plate end 150 can overlap a second plate end 152.

Figure 43:
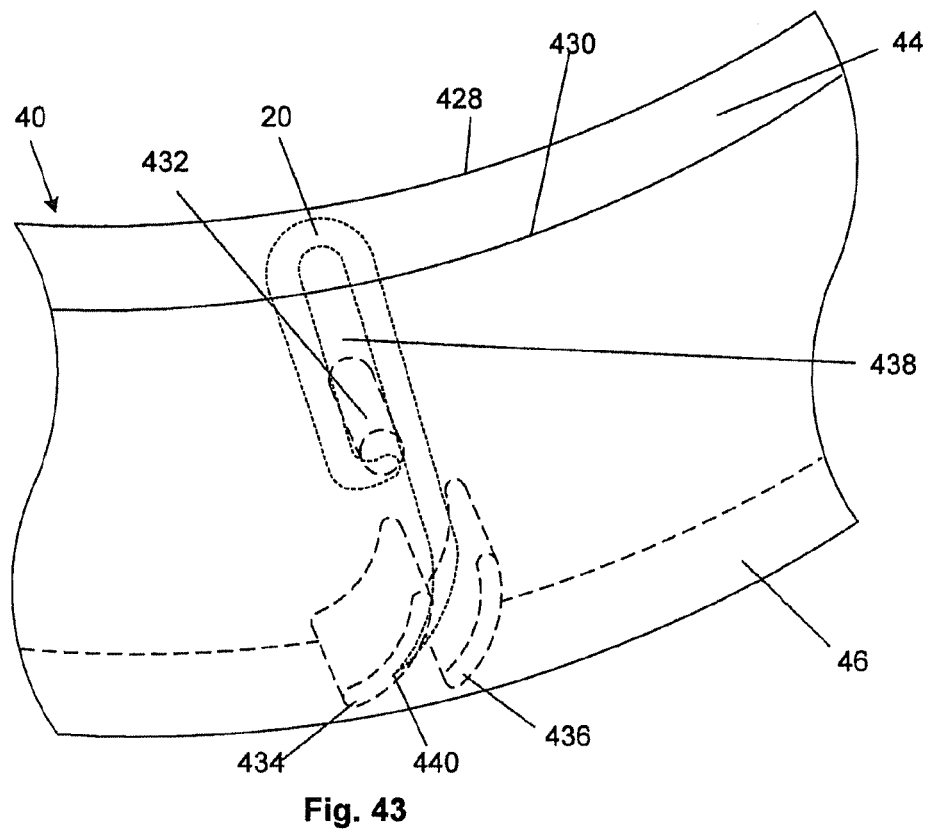
FIGS. 43-45 illustrate various complementary fixturing devices with fixturing devices therein.

FIG. 43 illustrates the gasket body 40 that can be made from a laminate of a first gasket layer 428 and a second gasket layer 430. The first and second gasket layers 428 and 430 can be fixedly or slidably attached to a slide rod 432, and fixedly attached to a first guide block 434 and a second guide block 436. The first and second guide blocks 434 and 436 can be adjacent to the bottom edge 46. The fixturing device 20 can have an elongated slide port 438. The fixturing device 20 can be slidably attached at the slide port 438 to the slide rod 432. A sharpened tip 440 of the fixturing device 20 can be slidably placed in a complementary fixturing device, for example a receptacle formed between the first and second guide blocks 434 and 436. Because the fixturing device 20 is limitedly slidable on the slide rod 432, the fixturing device 20 can be prevented from completely escaping or being removed from the gasket body 40. The fixturing device 20 can be loaded onto the gasket body 40 before the gasket body 40 is deployed and selectively activated or deployed into tissue depending on the condition and/or placement of the fixturing device 20 relative to the first mass.

Figure 44:
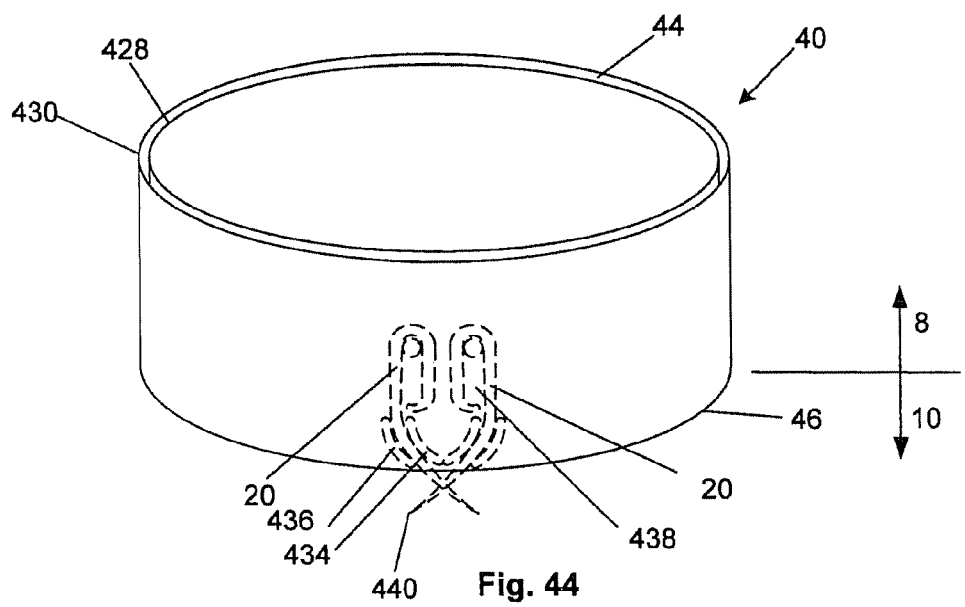

FIG. 44 illustrates two fixturing devices 20, as shown in FIG. 43, that can be placed adjacent to each other. The fixturing devices 20 can be turned opposite directions so to face each other, resulting in overlapping and/or adjacent placement of the two fixturing devices 20 after deployment, as shown.

Figure 45:
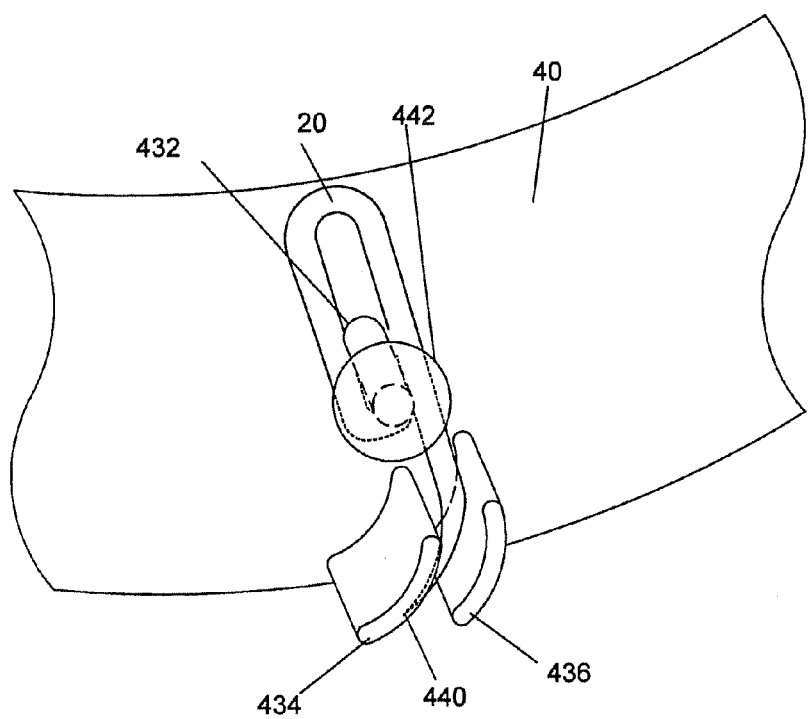

FIG. 45 illustrates the configuration of FIG. 43 without the second gasket layer 430. The slide rod 432 can be fixedly or rotatably attached at a first end to the gasket body 40. The slide rod 432 can be fixedly or rotatably attached at a second end to a radial directing element 442. The radial directing element 442 can be circular and can have a larger diameter than the slide rod 432.

Figure 46:
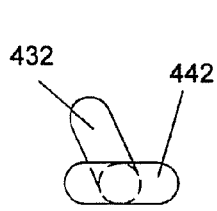
FIGS. 46-48 illustrate various directing elements.
Figure 47:
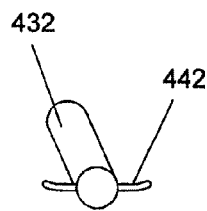
Figure 48:
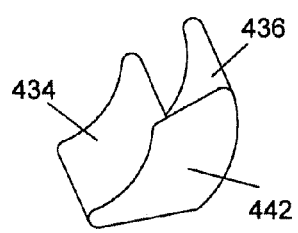

FIGS. 46-48 illustrate radial directing elements 442. FIG. 46 illustrates a radial directing element 442 that can be oval, rectangular or otherwise elongated. FIG. 47 illustrates a radial directing element 442 that can be thin and can be bent radial toward the gasket body 40 (not shown). FIG. 48 illustrates a radial directing element 442 that can be fixedly attached to the first and/or second guide blocks 434 and/or 436.

FIG. 49 illustrates a can 60 that can have cross-section C-C. FIG. 50 illustrates cross-section C-C. The can 60 can have teeth 154. The teeth 154 can be internal to the can 60. The teeth 154 can have shelves 156 and slopes 158. FIG. 51 illustrates a can 60 that can be made from a resilient material, for example, any polymer or metal listed herein. The can 60 can have slots 88 in the sides of the can 60.

FIGS. 52 to 55 illustrate sutures 6 that can be used with, for example, the cans 60 illustrated in FIGS. 49 to 51. The suture 6 can have one or more digitations, detents or pawls 160 fixedly attached to a filament 162. The pawls 160 can be conical (shown in FIG. 52), angled or straight tabs (shown in FIG. 53), substantially droplet-shaped (shown in FIG. 54), spherical (shown in FIG. 55) or a combination thereof. The tops of the droplet-shaped pawls 160 can be concave inward toward the filament 162. The sutures 6 illustrated in FIGS. 52 to 55 can be self-fixturingly ratcheted through a suitable can 60 and finitely adjusted as desired.

Figure 56:
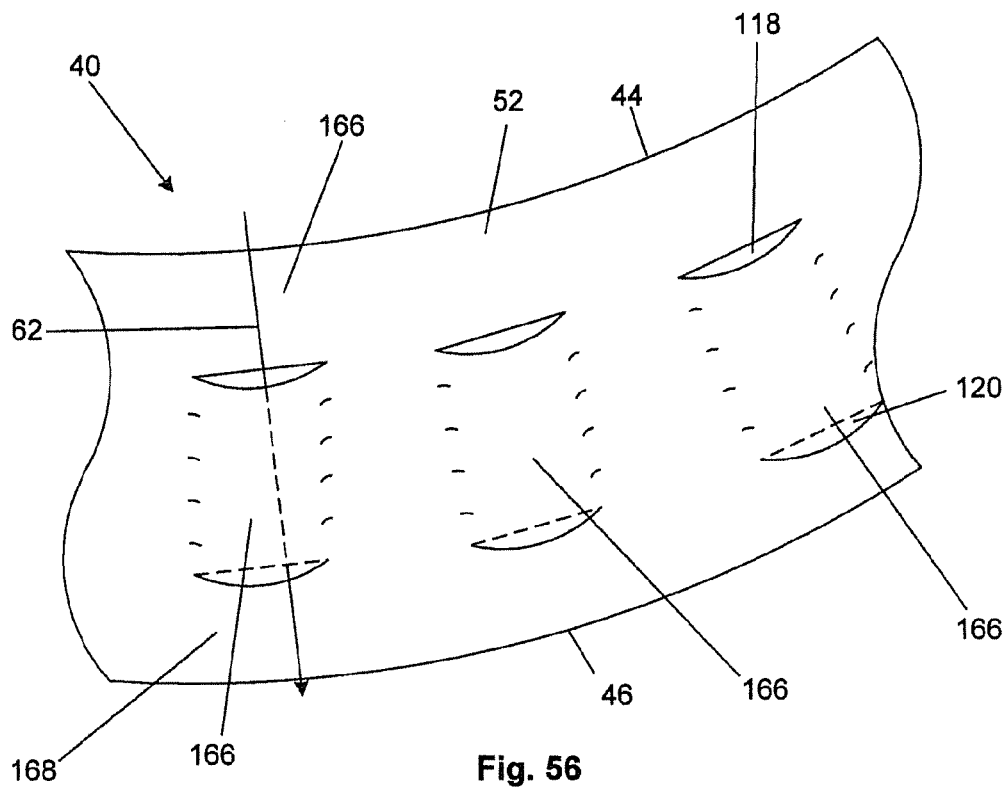
FIG. 56 illustrates complementary fixturing devices with a gasket body.
Figure 57:
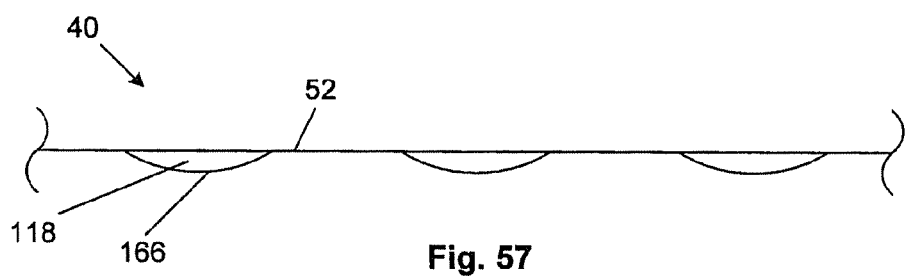
FIG. 57 is a top view of the gasket body of FIG. 56 after being straightened for illustrative purposes.

FIGS. 56 and 57 illustrate a portion of a sheet or the gasket body 40 that can have integral complementary fixturing devices. The complementary fixturing devices can be second wall segments 164. The second wall segments 164 can be raised portions of the wall 52. The wall 52 can have first wall segments 166 between the second wall segments 164 and the top edge 44. The wall 52 can have third wall segments 168 between the second wall segments 164 and the bottom edge 46. The hollow channel 62 can pass along the wall analogous to the hollow channel 62 for the can 60 shown in FIGS. 38 to 40.

Figure 58:
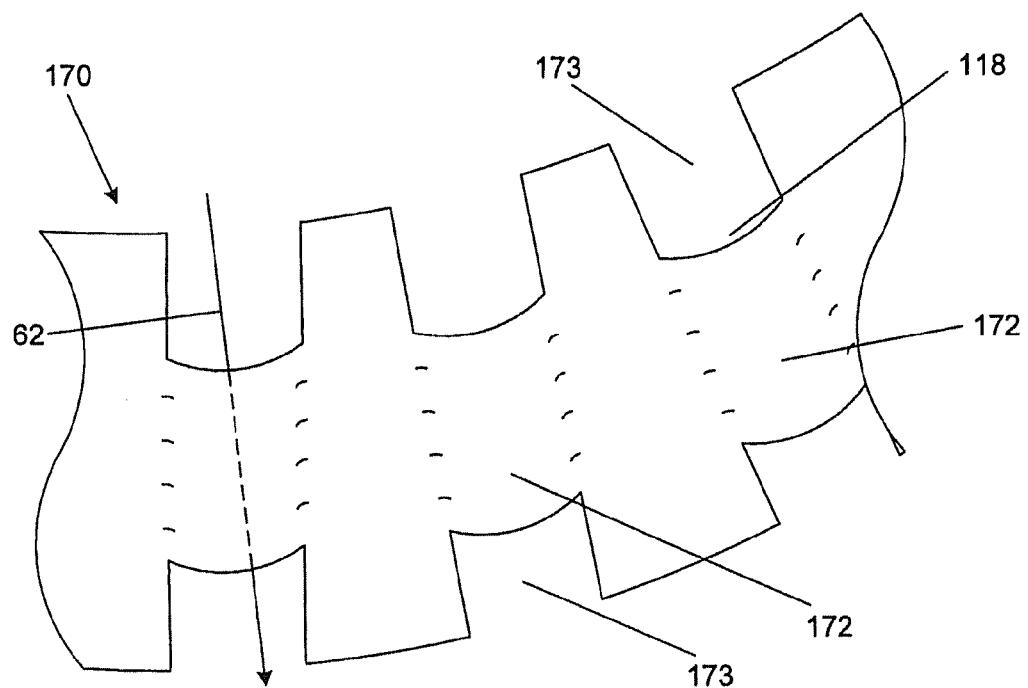
FIG. 58 illustrates complementary fixturing devices with a gasket body.
Figure 59:
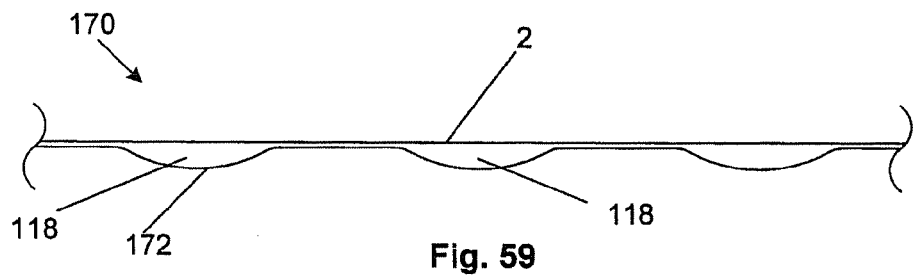
FIG. 59 is a top view of the gasket body of FIG. 58 after being straightened for illustrative purposes.

FIGS. 58 and 59 illustrate a portion of a sheet 170 that can have raised sheet segments 172 and has voids 173 above and below the raised sheet segments 172. During use, the sheet 170 can be attached to a prosthesis 2, for example the gasket body 40 or any available prosthesis to enable reduced implantation time.

The sheet 170 can be used in lieu of, or in addition to, sewing rings for multiple-piece heart valve assemblies, for example, heart valve assemblies disclosed by Griffin et al. in U.S. Pat. No. 6,241,765 and by Ritz in U.S. Pat. No. 5,976,183, both of which are hereby incorporated in their entireties. Other heart valve assemblies that can be used with the sheet 170 include, for example, the Advantage Bileaflet heart valve, Parallel valve, Freestyle stentless aortic valve, Hancock Porcine heart valve, Hancock apical left ventricular connector model 174A, Hancock valved conduit models 100, 105, 150, Hall Medtronic heart valve, Hall Medtronic valved conduit, MOSAICO heart valve and Intact porcine tissue valve (by Medtronic, Inc. Minneapolis, Minn.); Angelini Lamina-flo valve (by Cardio Carbon Company, Ltd., England); Bjork-Shiley single-disk, monostrut and caged-disk valves (Shiley, Inc., now-defunct, previously of CA); Wada-Cutter valve and Chitra Cooley-Cutter valve (by Cutter Biomedical Corp., San Diego, Calif.); Angioflex trileaflet polyurethane valve (by Abiomed, Inc., Danvers, Mass.); ATS AP Series heart valve and ATS Standard heart valve (by ATS Medical, Inc., Minneapolis, Minn.); ANNULOFLO® annuloplasty ring, ANNUFLEX® annuloplasty ring, CARBSEAL® valved conduit, ORBIS® Universal aortic and mitral valve, pediatric/small adult valve, R series valve, SUMIT® mitral valve, TOP HAT® aortic valve, OPTIFORM® mitral valve, MITROFLOW SYNERGY® PC stented aortic pericardial bioprosthesis and the SYNERGY® ST stented aortic and mitral porcine bioprosthesis (by CarboMedics, Inc., Austin, Tex.); ON-X® prosthetic heart valve (by MCRI®, LLC, Austin, Tex.); Starr-Edwards SILASTICO ball valve, Starr-Edwards 1000, Starr-Edwards 1200, Starr-Edwards 1260, Starr-Edwards 2400, Starr-Edwards 6300, Starr-Edwards 6500, Starr-Edwards 6520, Carpentier-Edwards porcine tissue valve, Carpentier-Edwards pericardial prosthesis, Carpentier-Edwards supra-annular valve, Carpentier-Edwards annuloplasty rings, Duromedics valve and PERIMOUNT® heart valve (by Edwards Lifesciences Corp., Irvine, Calif.); Cross-Jones Lenticular disc valve (by Pemco, Inc.); Tissuemed stented porcine valve (by Tissuemed, Ltd., Leeds, England); Tekna valve (by Baxter Healthcare, Corp., Deerfield, Ill.); Komp-01 mitral retainer ring (by Jyros Medical Ltd., London, England); SJM® Masters Series mechanical heart valve, SJM® Masters Series aortic valved graft prosthesis, ST. JUDE MEDICAL® mechanical heart valves, ST. JUDE MEDICAL® mechanical heart valve Hemodynamic Plus (HP) series, SJM REGENT® valve, TORONTO SPV® (Stentless Porcine Valve) valve, SJM BIOCOR® valve and SJM EPIC® valve (St. Jude Medical, Inc., St. Paul, Minn.); Sorin Bicarbon, Sorin Carbocast, Sorin Carboseal Conduit, Sorin Pericarbon and Sorin Pericarbon Stentless (by Snia S.p.A., Italy). The gasket body 40 described herein can also be used in lieu of the gasket bodies in any of the heart valve assemblies listed supra.

Figure 60:
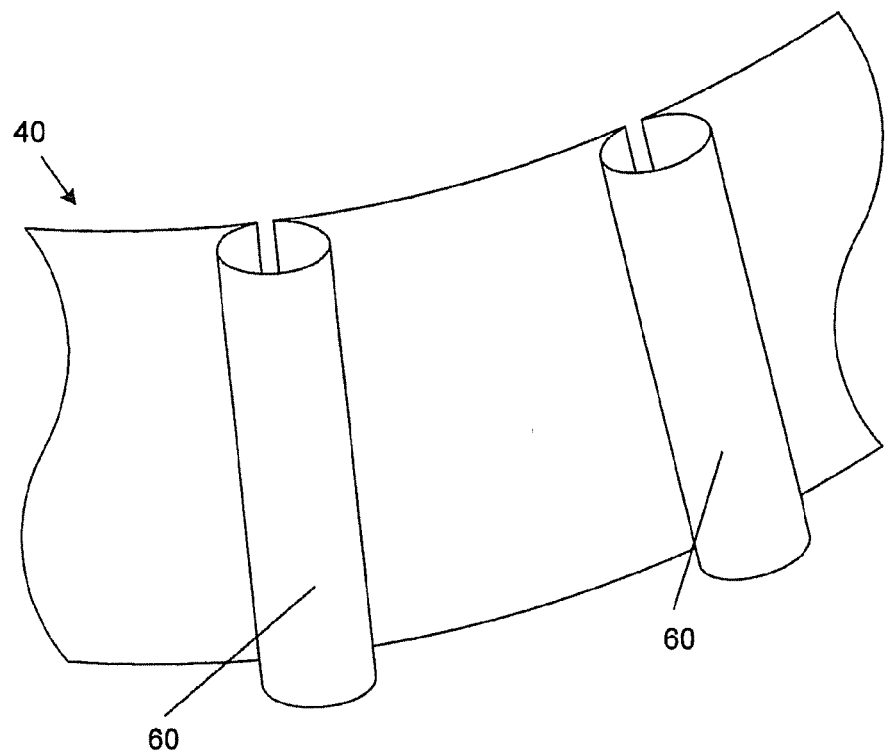
FIG. 60 illustrates complementary fixturing devices with a gasket body.
Figure 61:
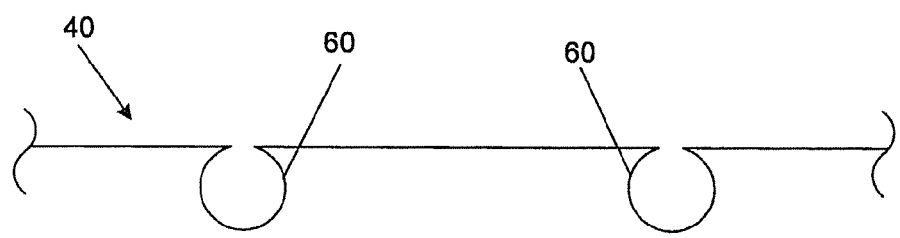
FIG. 61 is a top view of the gasket body of FIG. 60 after being straightened for illustrative purposes.

FIGS. 60 and 61 illustrate a sheet or gasket body 40 that can have undulations forming cans 60. The cans 60 can be substantially cylindrical. The cans 60 can be unclosed cylinders.

Figure 62:
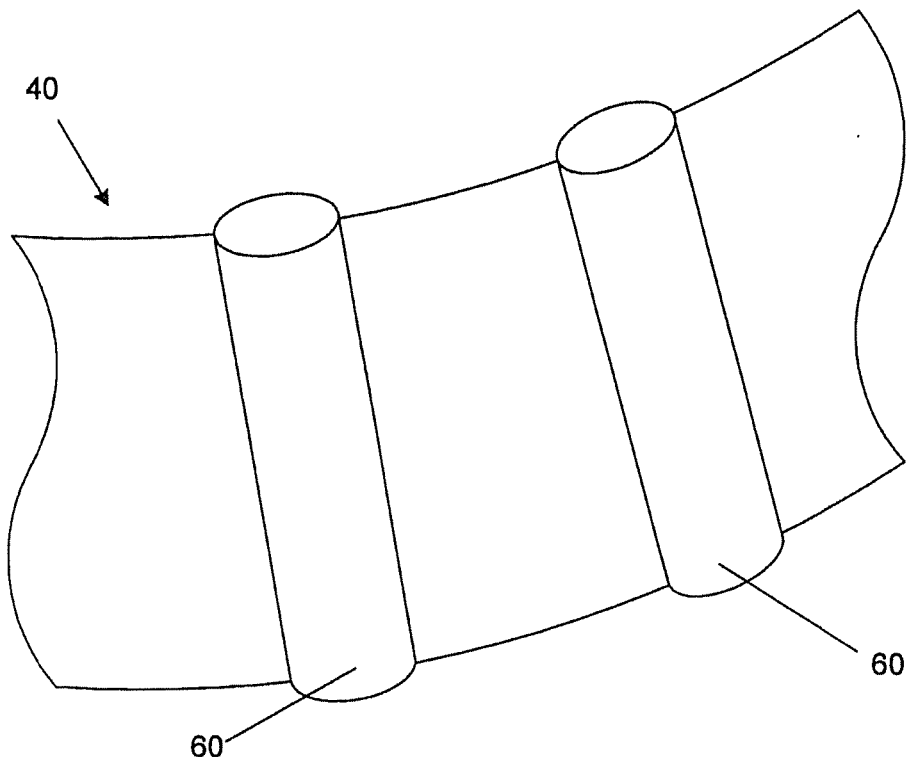
FIG. 62 illustrates complementary fixturing devices with a gasket body.
Figure 63:
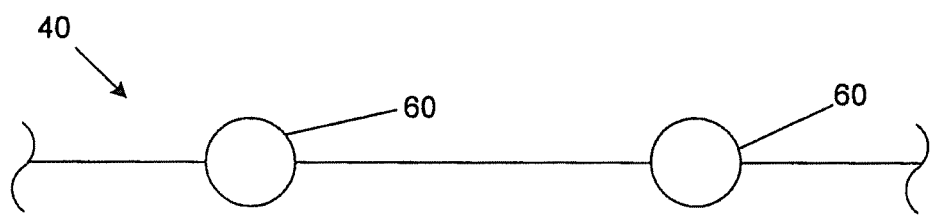
FIGS. 63 and 64 are top views of embodiments of the gasket body of FIG. 62 after being straightened for illustrative purposes.
Figure 64:
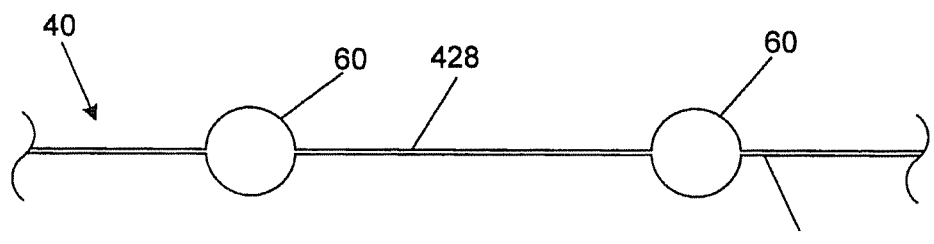

FIGS. 62 to 64 illustrate a sheet or gasket body 40 that can have substantially closed, substantially cylindrical cans 60. The sheet or gasket 40 can be made from a single layer, or can be made from a laminate that can have a first gasket layer 428 and a second gasket layer 430.

Figure 65:
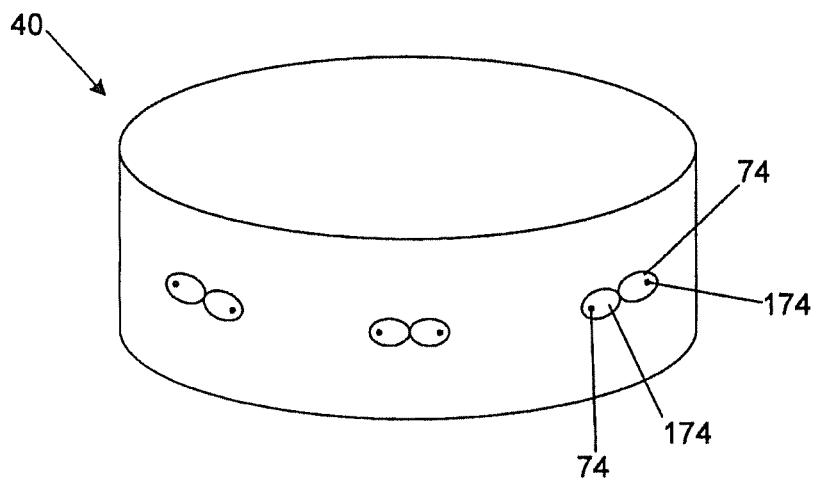
FIGS. 65 and 66 illustrate various complementary fixturing devices with gasket bodies.

FIG. 65 illustrates the gasket body 40 that can have the complementary fixturing devices that can be pairs of cams 174. The cams 174 can be rotatably attached to the gasket body 40 by the axles 74. The cams 174 can be oval or elliptical. The cams 174 can be biased to open upward or downward, and lock when the major axis of one cam 174 approaches parallel with the major axis of the other cam 174 in the pair of cams 174 (as shown in FIG. 27). A spool (not shown) can be located in or adjacent to the cam 174 to intake and/or roll-up the additional length of the suture 6 during deployment of the gasket body 40.

Figure 66:
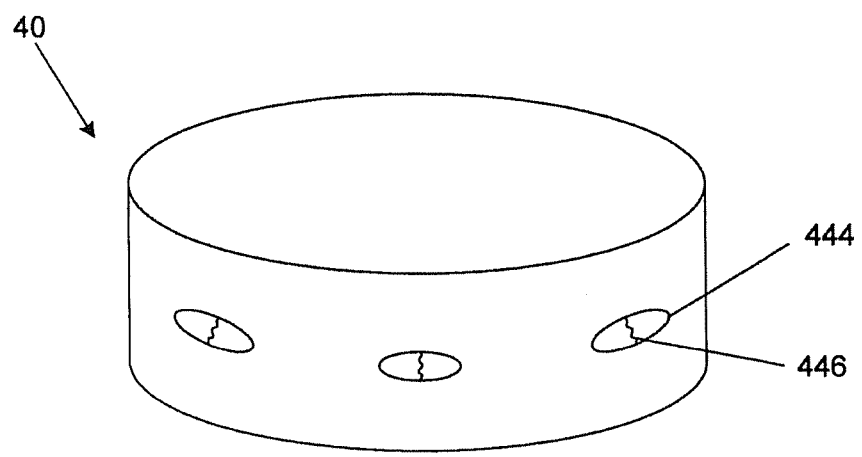

FIG. 66 illustrates the gasket body 40 that can have the complementary fixturing devices that can be a static receptacle 444. The static receptacle 444 can be on the outside of the gasket body 40. The static receptacle 444 can be resiliently elastic. The static receptacle 444 can be made of an elastomer. The static receptacle 444 can have a high fiction channel 446 passing through the static receptacle 444. The high fiction channel 446 can be formed by a tortuous path through the static receptacle 444. The diameter of the high fiction channel 446 can be larger, smaller or equal to the diameter of the suture 6.

Figure 67:
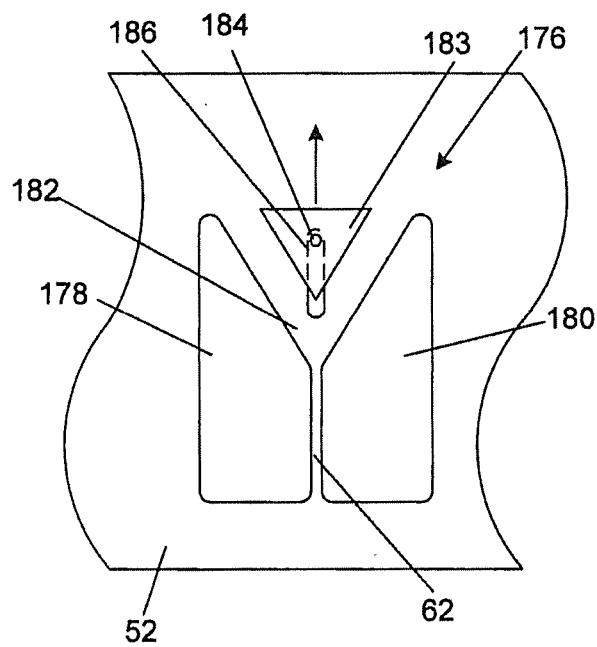
FIGS. 67 and 68 illustrate a complementary fixturing device in a first and a second configuration, respectively.

FIG. 67 illustrates a complementary fixturing device, for example a spindle lock 176, that can have an active internal obstacle in a first configuration. The spindle lock 176 can be attached to the wall 52. The spindle lock 176 can have a first seating block 178 and a second seating block 180. The hollow channel 62 can be between the first and second seating blocks 178 and 180. A seat 182 can be defined above the first and second seating blocks 178 and 180. The seat 182 can be angular or flat. The spindle lock 176 can have a spindle 183. The spindle 183 can be triangular or another shape that conforms to the seat 182. The spindle 183 can be fixedly attached to a pin 184. The pin 184 can be slidably attached to a slide hole, slot or groove 186 behind the spindle 183. During use, the suture (not shown) can be wrapped around the spindle 183. The suture 6 can be pulled up, in turn, pulling the spindle 183 up, shown by the arrow. In a configuration with the spindle 183 up and out of the seat 182, the suture 6 can be free to slide around the spindle 183.

Figure 68:
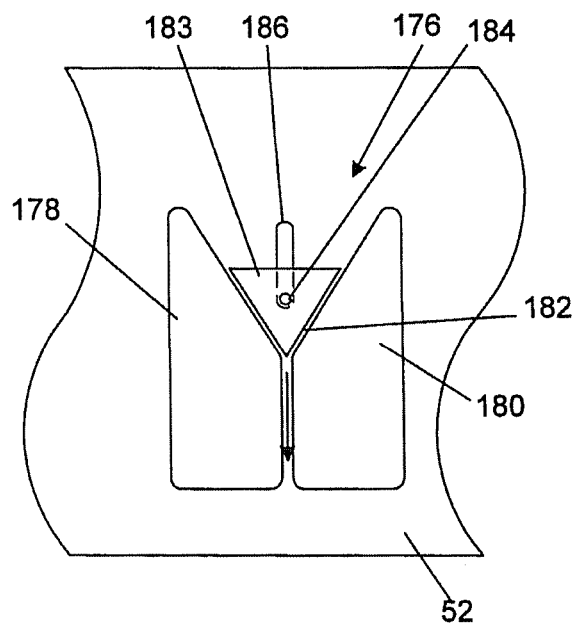

FIG. 68 illustrates the spindle lock 176 in a second configuration. The suture 6 can be pulled down, in turn, pulling the spindle 183 down, shown by the arrow. In a configuration with the spindle 183 down and in the seat 182, the suture 6 can be constricted and fixed between the spindle 183 and the first and second seating blocks 178 and 180.

Methods of Making

Figure 69:
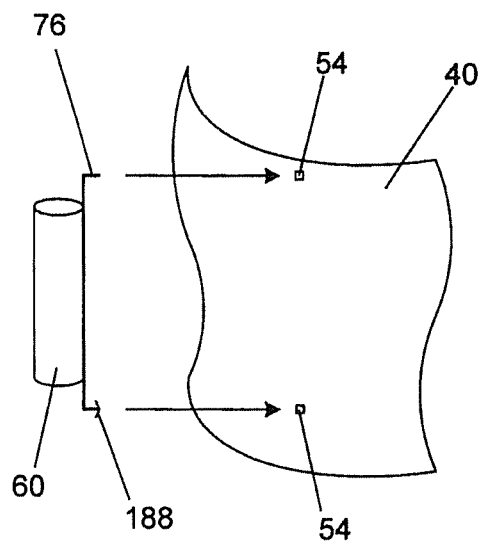
FIGS. 69 and 70 illustrate various methods of attaching a complementary fixturing device to a gasket body.

FIG. 69 illustrates a method of fixedly attaching the can 60 to a sheet or the gasket body 40. The frame 76 can be inserted (as shown by the arrows) through holes 54 in the sheet or gasket body 40. The frame 76 can then be attached to the sheet or gasket body 40 by crimping, stamping, melting, screwing, grommeting, snapping, bossing, gluing, welding or combinations thereof The frame 76 can have one or more snap bosses 188 at the ends of the frame 76.

Figure 70:
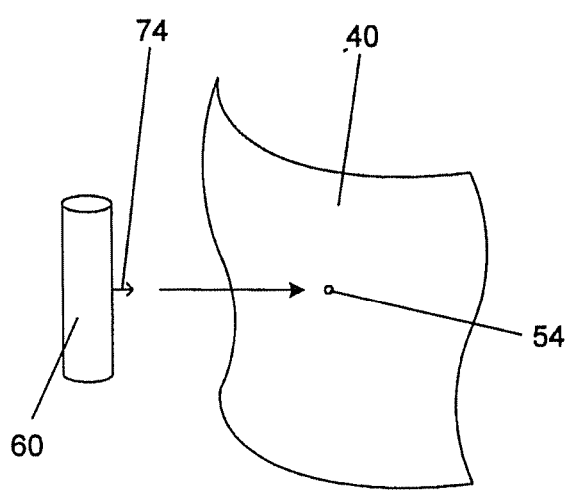

FIG. 70 illustrates a method of rotatably attaching the can 60 and the sheet or gasket body 40. The can 60 can have one axle 74. The axle 74 can be inserted (as shown by the arrow) into the hole 54.

Figure 71:
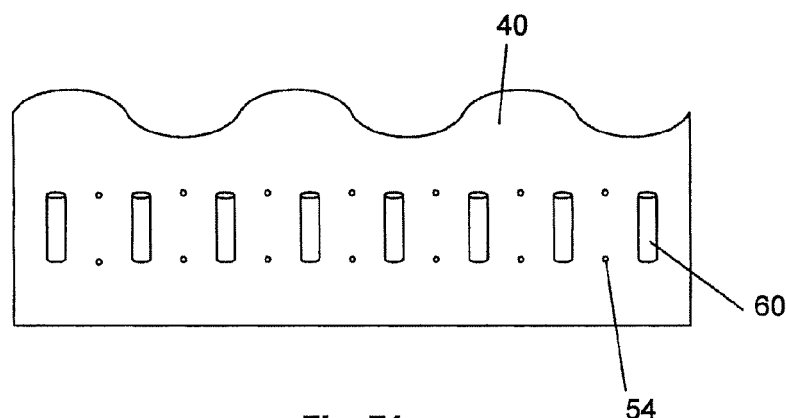
FIG. 71 illustrates complementary fixturing devices in or on a flattened and expanded gasket body or sheet.

FIG. 71 illustrates the sheet or gasket body 40 in an expanded and flattened view. The cans 60 can be attached to the sheet or gasket body 40 through the holes 54. The holes 54 not being used to attach cans 60 to the sheet or gasket body 40 can be used to attach a second prosthesis, for example a heart valve, to the sheet or gasket body 40.

Figure 72:
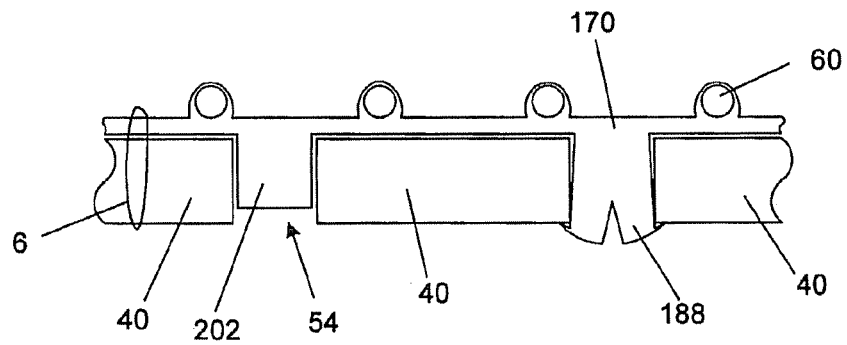
FIG. 72 is a close-up cross-sectional view of complementary fixturing devices in a sheet attached to a gasket body.

FIG. 72 illustrates the sheet 170 that can be fixedly attached to the gasket body 40, The sheet 170 can be made from, for example, any polymer listed herein. The cans 60 can be in or on the sheet 170, or between the sheet 170 and the gasket body 40. The sheet 170 can be attached to the gasket body 40, for example, by sutures 6, bosses 202 fit into the holes 54, snap bosses 188 fit into the holes 54 or combinations thereof.

Figure 73:
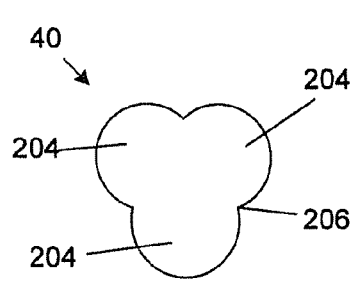
FIG. 73 is a top view of a trilobular gasket body.
Figure 74:
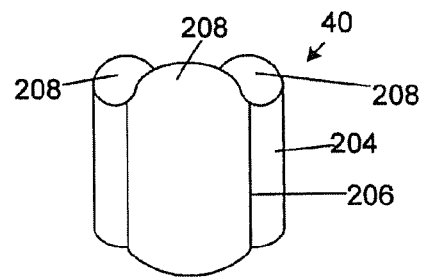
FIG. 74 is a front perspective view of a trilobular scalloped gasket body.

FIG. 73 illustrates the sheet or gasket body 40 wrapped or otherwise formed in a trilobular configuration. The gasket body 40 can have three lobes 204 and three cusps 206. FIG. 74 illustrates the sheet or gasket body 40 wrapped or otherwise formed in a scalloped, trilobular configuration. The gasket body 40 can have scallops 208 aligned with the lobes 204 or the cusps 206.

Figure 75:
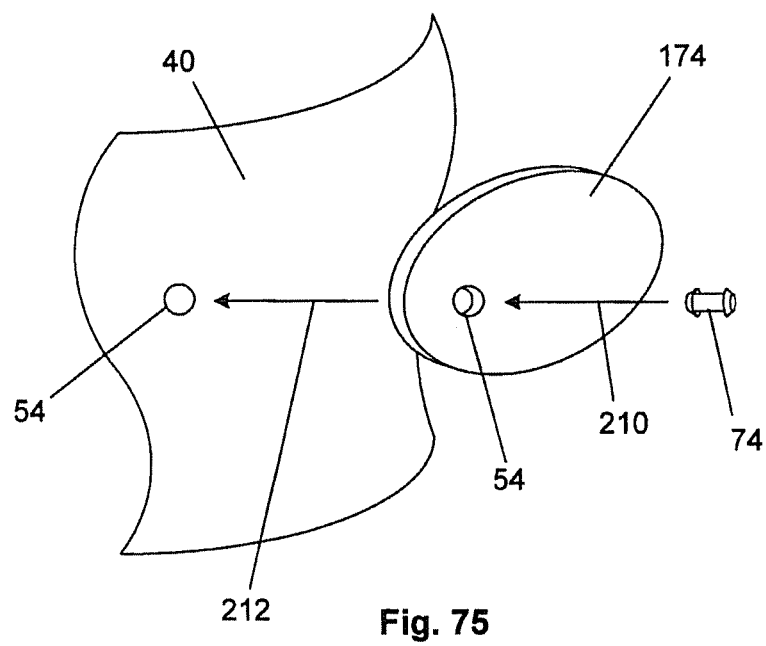
FIG. 75 illustrates assembly of a complementary fixturing device onto a gasket body.

FIG. 75 illustrates a method of rotatably attaching the cam 174 to the gasket body 40. The axle 74 can be pressed, as shown by arrow 210, into the hole 54 in the cam 174. The cam 174 can be placed against or near the gasket body 40, and the axle 74 can be pressed, as shown by arrow 212, into the hole 54 in the gasket body 40.

Figure 76:
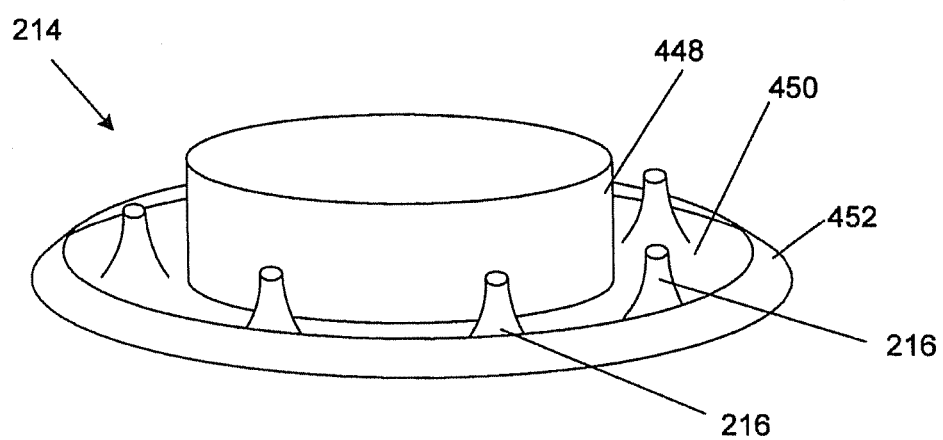
FIG. 76 illustrates a mold for making a part to hold complementary fixturing devices.

FIG. 76 illustrates a mold 214 that can be used to form a polymer, for example silicone, frame from which the sewing rings 14 having suture ports 66 can be made. The mold 214 can have cylindrical and/or conical protrusions 216 to form the suture ports 66. A mold outer wall 448 can extend radially inward from the radial outer edge of a mold base 450. The mold outer wall 448 can form the top of the flare or skirt 70. A mold inner wall 452 can extend substantially vertically from the radial inner edge of the mold base 450. One having an ordinary level of skill in the art can manufacture the sewing ring 14 using the mold 214.

As shown in FIG. 21, the tabs 48 can be sections of the gasket body 40 around which an about 180° cut can be made to allow the section of the gasket body 40 forming the tab 48 to articulate. The cut can be made by any method described infra.

The fixturing devices 20, pledget 16, gasket body 40, tabs 48, cans 60, plugs 58, cams 174, and other parts can be made from methods known to one having ordinary skill in the art. For example, manufacturing techniques include molding, machining, casting, forming (e.g., pressure forming), crimping, stamping, melting, screwing, gluing, welding, die cutting, laser cutting, electrical discharge machining (EDM) or combinations thereof.

Any parts, sub-assemblies, or the device as a whole after final assembly, can be coated by dip-coating or spray-coating methods known to one having ordinary skill in the art, for example to apply the agents described above. One example of a method used to coat a medical device for vascular use is provided in U.S. Pat. No. 6,358,556 by Ding et al. and hereby incorporated by reference in its entirety. Time release coating methods known to one having ordinary skill in the art can also be used to delay the release of an agent in the coating. The coatings can be thrombogenic or anti-thrombogenic.

Methods of Using

Figure 77:
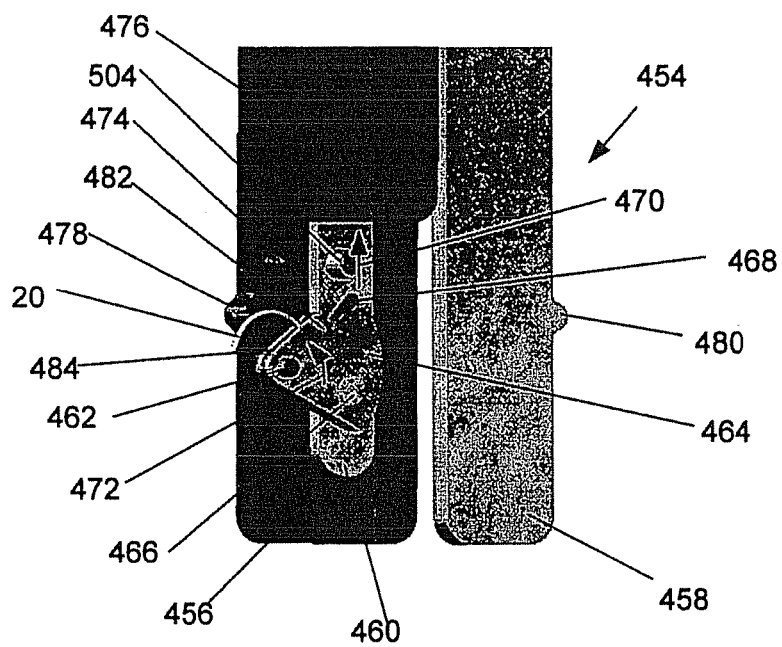
FIG. 77 illustrates a fixturing device deployment assembly with a fixturing device.
Figure 78:
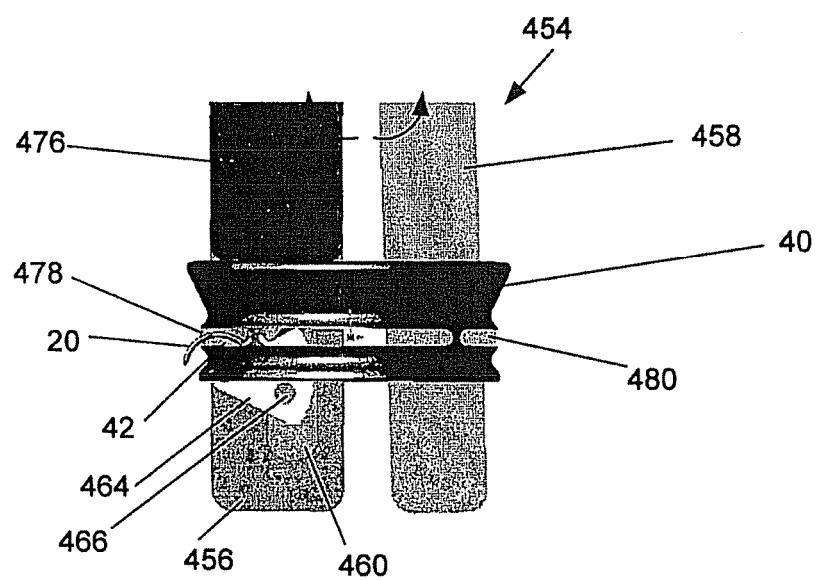
FIG. 78 illustrates a method of using the fixturing device deployment assembly of FIG. 78 with a fixturing device and a gasket body.

FIGS. 77 to 80 illustrate a method of using a fixturing device deployment assembly 454 to deploy fixturing device 20. As shown in FIGS. 77 and 78, the fixturing device deployment assembly 454 can have a static rod 456 rotatably connected, shown by arrows in FIG. 78, to a brace rod 458. The static rod 456 can be slidably connected to a dynamic rod 460. The static rod 456 can be rotatably connected at a pivot pin 456 to a cartridge 464. The dynamic rod 460 can be rotatably connected to the cartridge 464 at a driving pin 466. The cartridge 464 can deploy the fixturing device 20 in a curvilinear path. The cartridge 464 can be removably attached to the fixturing device 20. The cartridge 464 can have an ejection activator 468.

An upward force, shown by arrow 470, can be applied to the dynamic rod 460. As the dynamic rod 460 moves upward, the cartridge 464 can rotate, shown by arrow 472. The cartridge 464 can rotate to press the ejection activator 468 against an ejection pin 474. The ejection pin 474 can be part of, or fixedly attached to, the static rod 456. The fixturing device 20 can eject from the cartridge 464 when the ejection activator 468 is pressed into the ejection pin 474 with sufficient force.

A cover 476 can be slidably attached to the static rod 456. The cover 476 can be slid down to cover the static rod 456 during use (the cover 476 is open in FIGS. 77 and 78 for illustrative purposes). When the cover 476 covers the static rod 456, the cover 476 can protect the elements of the fixturing device deployment assembly 454 and provide additional support for the dynamic rod 460 and the cartridge 464.

The fixturing device deployment assembly 454 can be placed into a gasket body 40. The static rod 456 can have a first deployment guide 478. The brace rod 458 can have a second deployment guide 480. The fixturing device deployment assembly 454 can self-align with the gasket body 40 by fitting the first and second deployment guides into appropriate grooves or notches on the gasket body 40. The fixturing device deployment assembly 454 can be firmly held in place by applying pressure against the gasket body 40 with the static rod 456 and the brace rod 458. Once the fixturing device deployment assembly 454 is aligned with the gasket body 40, the fixturing device 20 can be deployed through the window 42.

Figure 79:
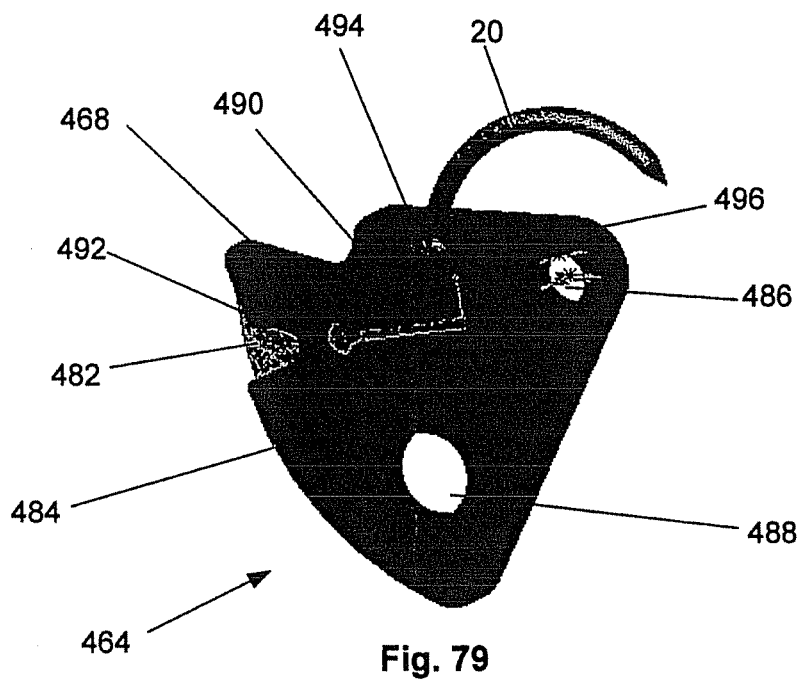
FIGS. 79 and 80 illustrate a method of using the cartridge of the fixturing device deployment assembly of FIGS. 77 and 78.
Figure 80:
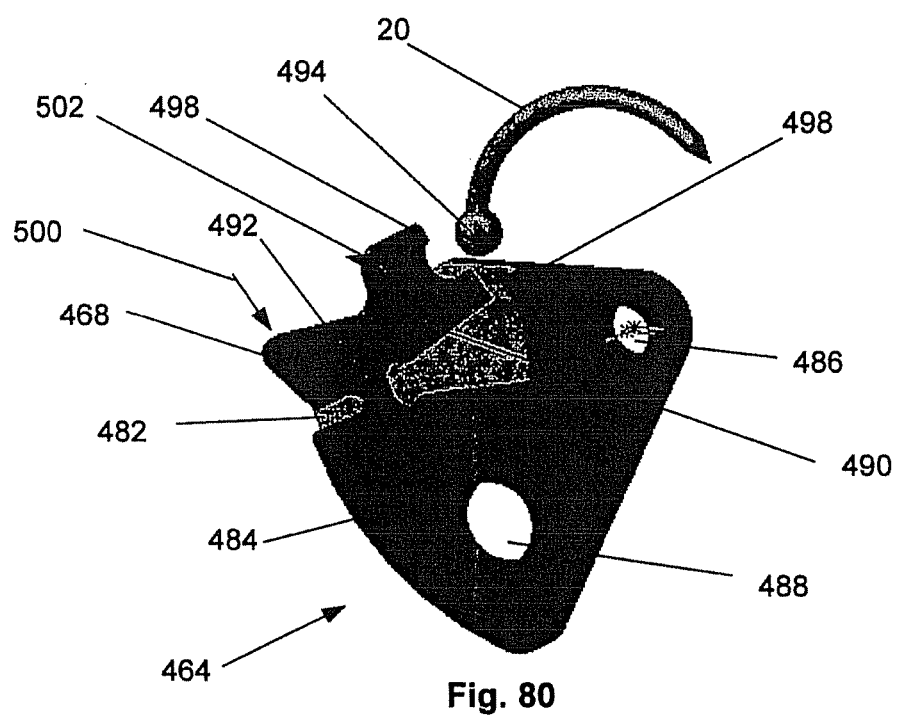

FIGS. 79 and 80 illustrate the cartridge 464 deploying the fixturing device 20. The cartridge 464 can have a first outer panel 482, a load panel 484 adjacent to the first outer panel 482 and a second outer panel (not shown for illustrative purposes) adjacent to the load panel 484. The cartridge 464 can have a pivot port 486 to rotatably attach to the pivot pin 462. The cartridge 464 can have a drive port 488 to rotatably attach to the driving pin 466.

An ejection section 490 can be rotatably attached to the load panel 484 at a joint 492. The ejection activator 468 can be a protruding portion of the ejection section 490. A locking section 494 of the fixturing device 20 can be in a loading capsule 496. The locking section 494 or another portion of the fixturing device 20 can be attached (not shown) to the suture 6. The loading capsule 496 can be defined by the ejection section 490 and an ejection lip 498. The ejection lip 498 can be part of the load panel 484.

When the ejection pin 498 presses, shown by arrow 500, against the ejection activator 468, the ejection section 490 can rotate, shown by arrow 502, releasing the fixturing device 20 from the cartridge 464. After the ejection pin 474 begins to press against the ejection activator 468 and before the ejection section 490 rotates, an ejection force can be applied by the locking section 494 to the ejection lip 498. The ejection force must be large enough to deform the locking section 494 and/or the ejection lip 498 and/or the ejection section 490 before the ejection section 490 can rotate. The large ejection force can cause the fixturing device 20 to jump or launch from the cartridge 464 when deployed. The jump or launch also provides tactile feedback of deployment of the fixturing device 20 to the user of the fixturing device deployment assembly 454.

Figure 84:
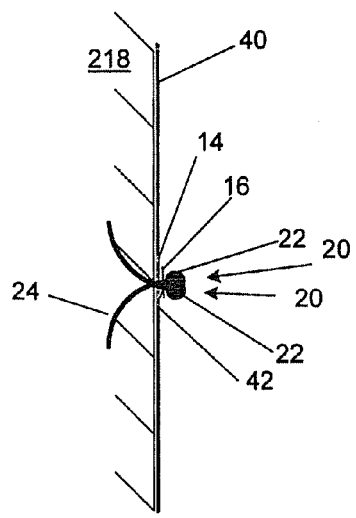
FIG. 84 illustrates a method of using two fixturing devices.

A second cartridge (not shown) can be attached to the dynamic rod 460 similar to the attachment of the cartridge 464, but "upside down". The fixturing device 20 of the second cartridge can be delivered overlapping the fixturing device 20 of the cartridge 464, as shown in FIG. 84. The drive port (not shown) of the second cartridge can be rotatably attached to the second cartridge driving pin 504, The pivot port (not shown) of the second cartridge can be rotatably attached to the ejection pin 474. The pivot pin 462 can act as the ejection pin for the second cartridge.

Figure 81:
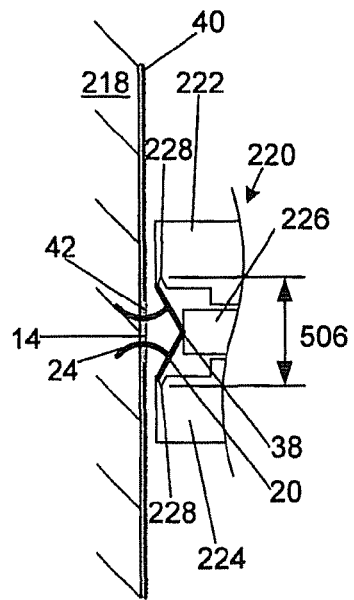
FIGS. 81-83 illustrate a method of using a fixturing device.
Figure 82:
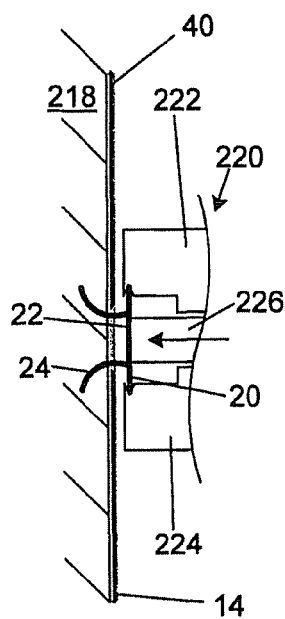
Figure 83:
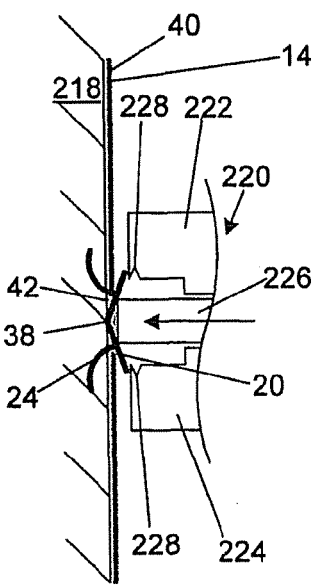

FIGS. 81 to 83 illustrate a method of fixing a first mass, for example biological heart tissue 218, to a second mass, for example the gasket body 40. The gasket body 40 can be placed adjacent to the tissue 218. An applicator assembly 220 can be placed adjacent to, and aligned with, the window 42. The gasket body 40 can be covered by a fabric or the sewing ring 14.

The applicator assembly 220 can have a top mount 222 that can be fixedly attached to a bottom mount 224. The applicator assembly 220 can have a press 226 that can be slidably attached to the top mount 222 and/or the bottom mount 224. The mounts 222 and 224 can each have a loading notch 228. The fixturing device 20 can be loaded into the loading notches 228, and the fixturing device 20 can be pressed against the press 226, as shown in FIG. 81. The fixturing device 20 can fill the notches 228 completely when loaded, or the notches 228 can have available space for the expansion of the fixturing device 20. The distance between the loading notches 228 can be a loading notch height 506. The loading notch height 506 can be from about 1.27 mm (0.050 in.) to about 12.7 mm (SO0 in.), for example, about 3.20 mm (0.126 in.).

As illustrated by the arrow in FIG. 82, the press 226 can be slidably moved (as shown by the arrow) toward the tissue 218, the press 226 can contact and push the fixturing device 20 on or near the fold 38. The fixturing device 20 can expand to fill the notches 228 and/or the fixturing device 20 can deform. The protrusions 24 can move through the tissue 218.

Before the press 226 forces the base 22 to form a straight plane, or before the base 22 can otherwise not resiliently return to the configuration shown in FIG. 81, the press 226 can be returned to the position shown in FIG. 81 and the fixturing device 20 can be removed from the tissue 218. In this way, portions of the tissue 218 can be tested with the protrusions 24 before the fixturing device 20 is completely deployed.

FIG. 83 illustrates completely deploying the fixturing device 20. The press 226 can be slid (as shown by the arrow) far enough toward the tissue 218 to egress the fixturing device 20 from the notches 228. The window 42 can be dimensioned to fix, for example by interference fitting or wedging, the fixturing device 20 into the gasket body 40 when the fixturing device 20 is completely deployed.

The protrusions 24 do not need to be curved, but if the protrusions 24 are curved and the protrusions 24 are deployed using the curvilinear motion shown in FIGS. 81 to 83, damage to the tissue 218 can be minimized. The fixturing device 20 can be oriented to any angle about the longitudinal axis of the press 226 before the fixturing device 20 is deployed.

FIG. 84 illustrates two fixturing devices 20 (similar to the fixturing device illustrated in FIG. 5) that can be deployed in a window 42 to fix the gasket body 40 to the tissue 218. The fixturing devices 20 can be placed to maximize the holding force, for example, the fixturing devices 20 can be placed at substantially the same position in the window 42 and deployed through the tissue 218 in substantially opposite directions.

Figure 85:
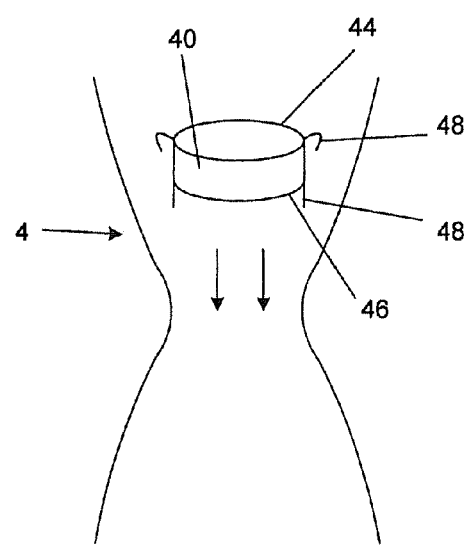
FIGS. 85-87 illustrate a method of using fixturing devices attached to a gasket body.
Figure 86:
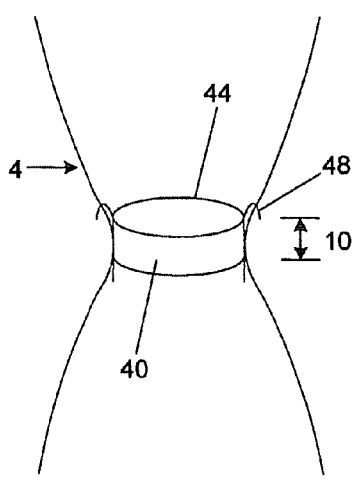
Figure 87:
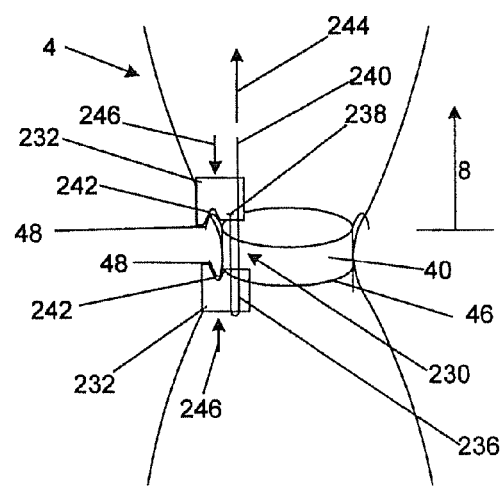

FIGS. 85 to 87 illustrate a method of deploying the gasket body 40 that can have the pre-deployed tabs 48 attached to the top edge 44 and additional tabs 48 attached to the bottom edge 46. The gasket body 40 can be lowered through the vessel 4, as shown by the arrows in FIG. 85. As illustrated in FIG. 86, the gasket body 40 can be placed in the trans-annular space 10. The tabs 48 attached to the top edge 44 can hook into the vessel wall, attaching the gasket body 40 to the vessel 4.

FIG. 87 illustrates a method of deploying the tabs 48, for example the tabs 48 attached to the bottom edge 46. A tab deployment assembly 230 can be positioned adjacent to the gasket body 40.

The tab deployment assembly 230 can have a first anvil 232 and a second anvil 234. A cable, rods or line 236 (referred to hereafter as the line 236 for illustrative purposes) can be fixedly attached to the first anvil 232 at an anchoring point 238. The line 236 can then pass through, and be slidably attached to, the second anvil 234. The line 236 can then pass through, and be slidably attached to, the first anvil 232. A free end 240 of the line 236 can extend into and beyond the supra-annular space 8.

The anvils 232 and 234 can have curved faces 242. The faces 242 can be positioned directly adjacent to the tabs 48. When the free end 240 of the line 236 is pulled, as shown by arrow 244, the first anvil 232 and the second anvil 234 move toward each other, as shown by arrows 246. The anvils 232 and 234 can then reshape the tabs 48. Reshaping the tabs 48 can include curving the tabs 48 and pushing the tabs 48 into the vessel wall. The anvils 232 and 234 can press into the vessel wall, if necessary, to complete the reshaping of the tabs 48.

Figure 88:
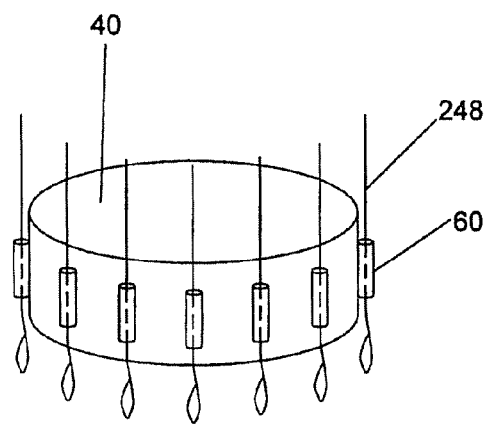
FIG. 88 illustrates snares loaded into complementary fixturing devices on a gasket body.
Figure 89:
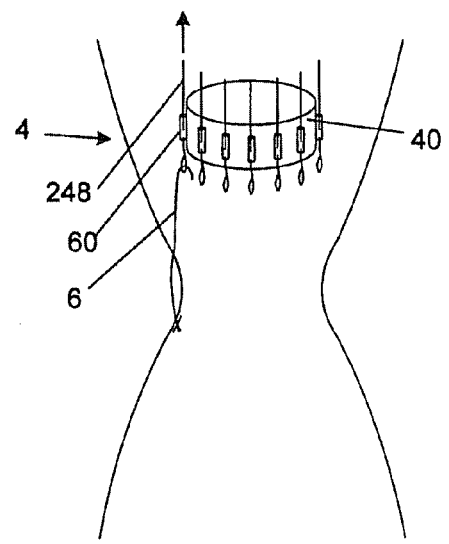
FIG. 89 illustrates a method of using snares loaded into complementary fixturing devices on a gasket body.

FIG. 88 illustrates the gasket body 40 shown in FIG. 23 with looped snares 248 loaded into the cans 60. (Only the snares 248 on the front half of the gasket body 40 are shown for illustrative purposes.) The snares 248 can be used with any gasket body 40 using complementary fixturing devices, for example cams 174. The snares 248 can be any suitable snare known to one having ordinary skill in the art, for example a stainless steel snare having a diameter of about 0.2 mm (0.006 in.). FIG. 89 illustrates the suture 6, already passed through the vessel wall, passed through the snare 248. Single stitches and mattress stitches, both known to those having ordinary skill in the art, can be used to attach the suture 6 to the vessel wall. The snare 248 can then be pulled, as shown by the arrow, through the can 60, thereby feeding the suture 6 through the can 60.

Figure 90:
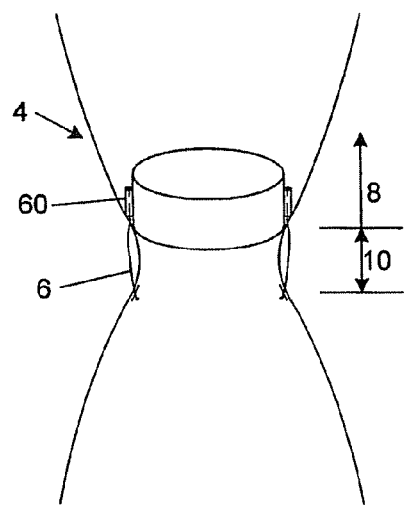
FIG. 90 illustrates a gasket body attached to a first mass with complementary fixturing devices.

Once all the desired sutures 6 are fed through the cans 60, the gasket body 40 can be parachuted down onto the shoulder between the supra-annular and trans-annular spaces 8 and 10, as shown in FIG. 90. The parachuting can be done with the assistance of an aligning stick or valve holder (not shown) to align the gasket body 40, as known by one having ordinary skill in the art. The cans 60 can be crimped, plugged or otherwise locked, and the excess suture 6 can be trimmed and removed.

Figure 91:
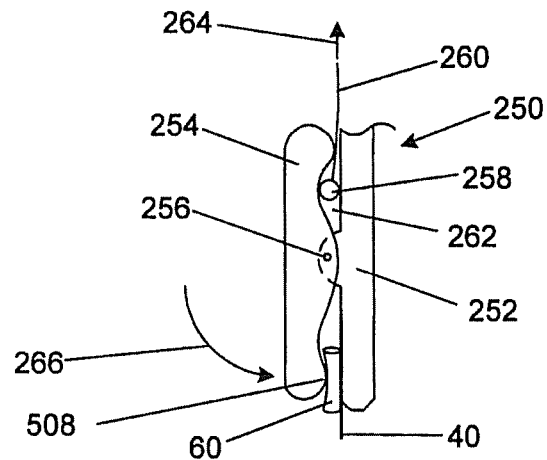
FIGS. 91 and 92 illustrate various devices for and methods of crimping a complementary fixturing device.

As illustrated in FIG. 91, a remote crimping tool 250 can be used to crimp the cans 60. The remote crimping tool 250 can have an arm 252 rotatably attached to a crushing member 254 at a pivot 256. The can 60, attached to the gasket body 40, can be loaded between the crushing member 254 and the arm 252. The crushing member 254 can have a crush head 508. An actuator ball 258 can be fixedly attached to a pull line 260. The actuator ball 258 can be in a ball cavity 262 between the arm 252 and the crushing member 254. The crushing member 254 can block the ball 258 from exiting the ball cavity 262. When the pull line 260 is pulled, as shown by arrow 264, the ball 258 forces the crushing member 254 in the direction of arrow 266. The crush head 508 can then crush the can 60.

Figure 92:
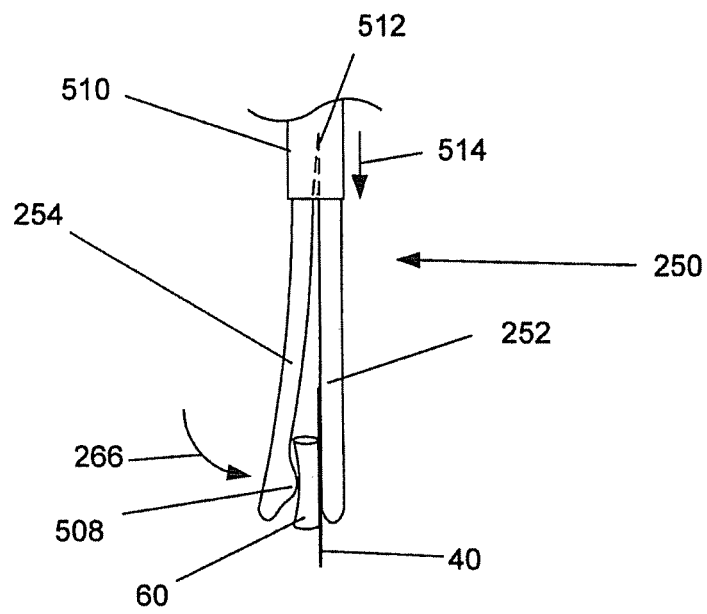

FIG. 92 illustrates another remote crimping tool 250 that can have an arm 252 that can be fixedly attached to the crushing member 254 at a proximal end (not shown). A slide tensioner 510 can be slidably attached to the arm 252 and the crushing member 254. The slide tensioner 510 can be non-deformable. The slide tensioner 510 can constrain the bending strain of the arm and the crushing member 254. The slide tensioner 510 can have a bending stresser 512 between the arm 252 and the crushing member 254. The crushing member 254 can be resiliently biased to stay apart from the arm 252 and/or the bending stresser 512 can force a bending strain upon the arm 252 and/or the crushing member 254. Bending strain over all or part of the length of the arm 252 and/or crushing member 254 can bend the crushing member 254 sufficiently to allow the can 60 to fit between the crush head 508 and the arm 252. When the slide tensioner 510 is slid toward the can, shown by arrow 514, the slide tensioner 510 forces the crushing member 254 in the direction of arrow 266.

Figure 93:
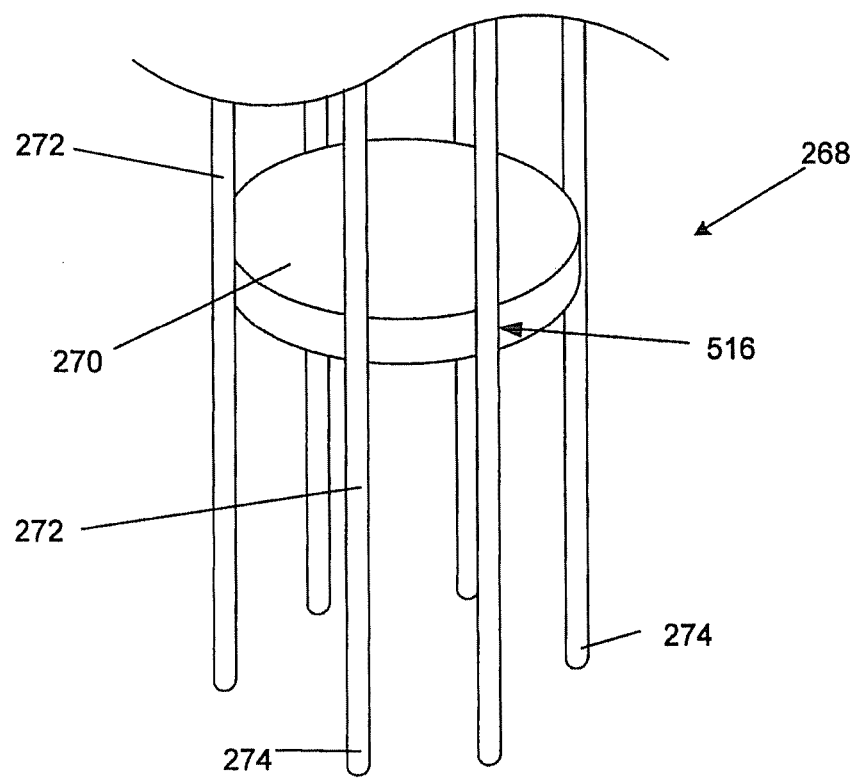
FIG. 93 illustrates a device for implanting a gasket body having complementary fixturing devices.
Figure 94:
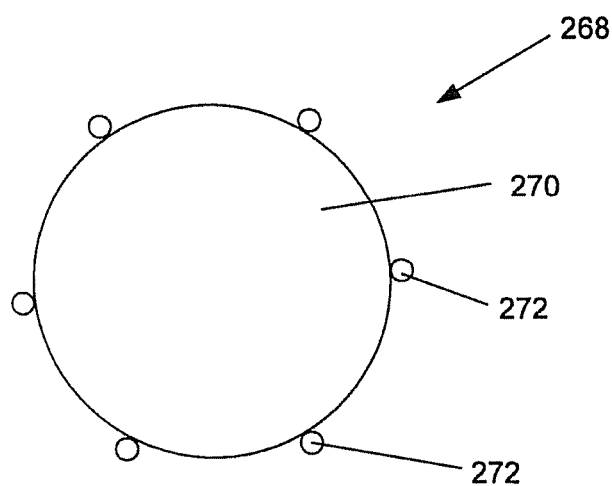
FIG. 94 is a bottom view of the device of FIG. 93.

FIGS. 93 and 94 illustrate a deployment tool 268 that can be used to implant the gasket body 40 to the desired site. The deployment tool 268 can have a support 270, for example a disc. The deployment tool 268 can have substantially parallel engagement devices, for example tubes 272. The tubes 272 can be fixedly attached to the support 270 at an attachment area 516. Some or all of the tubes 272 can be unattached to the support 270. For example, about three of the tubes 272 can be unattached to the support 270. The tubes 272 can be hollow. The tubes 272 can be substantially cylindrical. The tubes 272 can have tube ends 274. The tube ends 274 can be open-ended. The tube ends 274 can be resilient.

Figure 95:
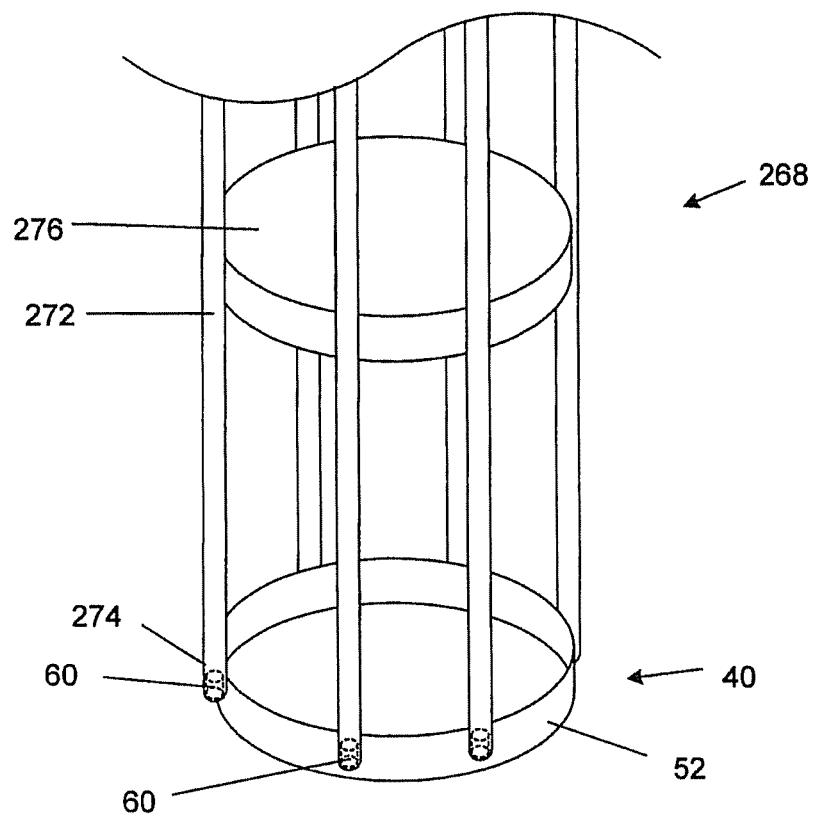
FIG. 95 illustrates a method of using the device of FIG. 93.

FIG. 95 illustrates a method of using the deployment tool 268 with the gasket body 40. The cans 60 can be engaged by the tube ends 274. The tube ends 274 can fit over and hold the cans 60.

Figure 96:
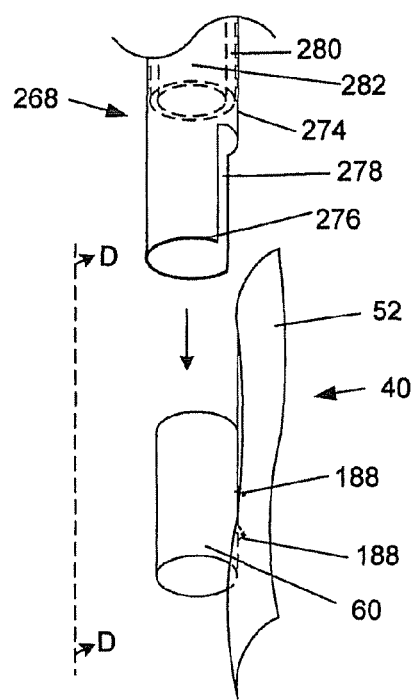
FIG. 96 illustrates the engagement device about to engage the complementary fixturing device.

FIG. 96 illustrates the deployment tool 268 and the can 60 and a portion of the gasket body 40 before the deployment tool 268 engages the can 60. The edge of the tube end 274 of the deployment tool 268 can have a lip 276. The tube end 274 can have an engagement hole 278 cut or formed along the side of the tube end 274. The engagement hole 278 can be sized to slide around the snap bosses 188. The tube end 274 can have a disengagement driver 280, for example a hollow catheter, that can extend along the length of the tube 272. The inside of the disengagement driver 280 can have an instrument port 282. The tube end 274 can be moved adjacent to the can 60, as shown by the arrow.

Figure 97:
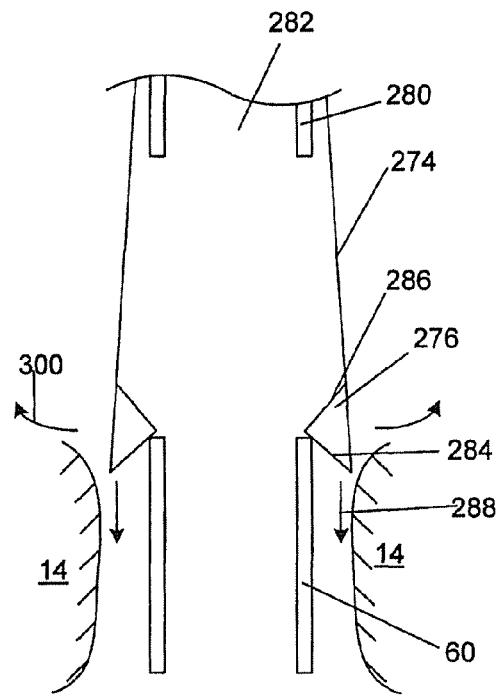
FIG. 97 illustrates section D-D as the engagement device begins to engage the complementary fixturing device.

FIG. 97 illustrates section D-D as the tube end 274 begins to engage the can 60. The lip 276 can have an engagement face 284 and a disengagement face 286. As the tube end 274 contacts the can 60, the can 60 can slide against the engagement face 284. The tube end 274 can be pushed over the can, as shown by arrows 288, and the tube end 274 can then flex outward, shown by arrows 300. The radius of the can 60 can then be accommodated by the tube end 274 and the tube end 274 can be slid over the length of the can 60.

The sewing ring 14 can be separated from the can 60 where the can 60 is engaged by the tube end 274 so that the sewing ring 14 does not substantially interfere with the tube end 274. The tube end 274 can be fit (not shown) into the inner radius of the can 60 and the lips 276 can extend (not shown) radially outward from the tube end 274 and the sewing ring 14 can substantially attach to the can 60 around the entire perimeter of the can 60.

Figure 98:
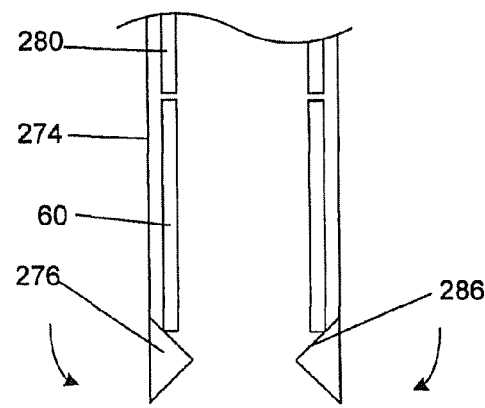
FIG. 98 illustrates section D-D while the engagement device is engaged with the complementary fixturing device.
Figure 99:
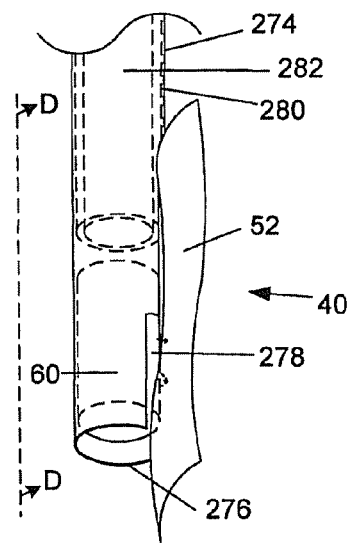
FIG. 99 illustrates the engagement device engaged with the complementary fixturing device.

FIGS. 98 and 99 illustrate when the tube end 274 engages the can 60. When the lip 276 get to the end of the can 60, the lip 276 can return to a relaxed, non-flexed position, shown by the arrows.

Figure 100:
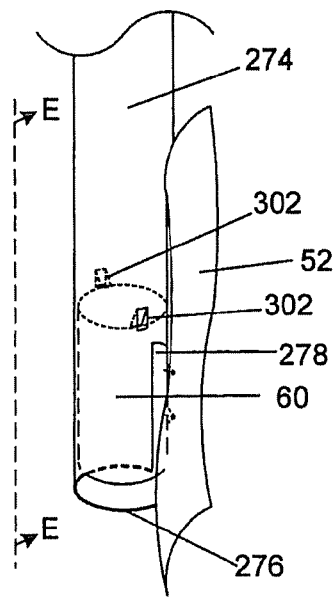
FIG. 100 illustrates the complementary fixturing device secured between the retention devices and the lip.
Figure 101:
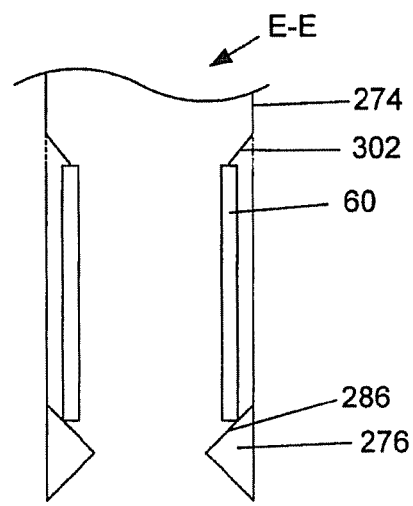
FIG. 101 illustrates section E-E.

FIGS. 100 and 101 illustrate the can 60 secured during deployment between retention devices, for example flaps 302, and the disengagement face 286 of the lip 276. The flaps 302 can be cut out of the wall of the tube end 274. The flaps 302 can be resilient. The flaps 302 can flex out of the way of the disengagement driver 280 during use.

Figure 102:
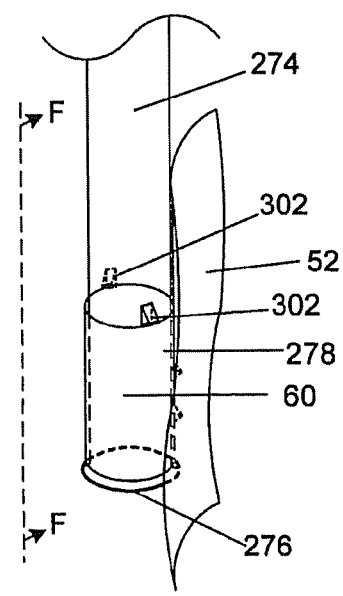
FIG. 102 illustrates the complementary fixturing device secured between the retention devices and the lip.
Figure 103:
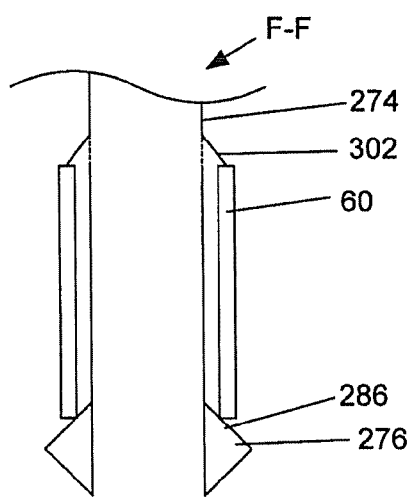
FIG. 103 illustrates section F-F.

FIGS. 102 and 103 illustrate the can 60 secured during deployment similar to the can 60 of FIGS. 100 and 101 except the tube end 274 can be inside the diameter of the can 60, and the lip 276 and the flaps 302 can face radially outward. The lip 276 can be flexible and/or have a notch, hole or slot to improve flexing during engagement and disengagement of the can 60.

Figure 104:
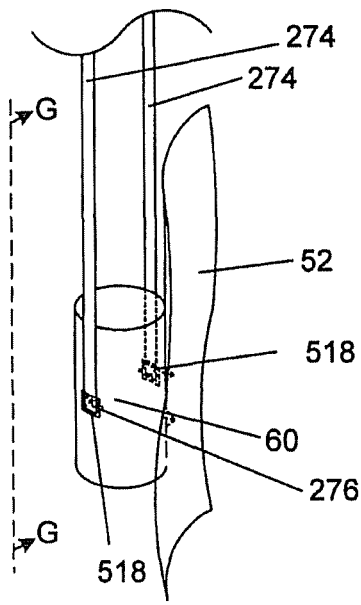
FIG. 104 illustrates the complementary fixturing device secured between two parts of the tube end.
Figure 105:
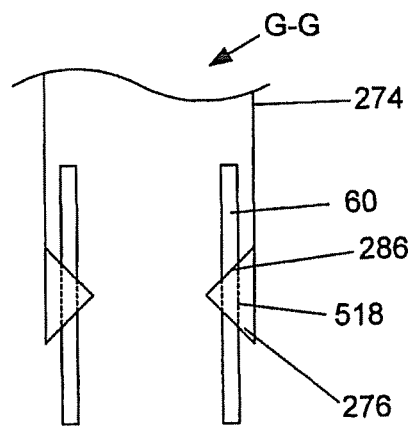
FIG. 105 illustrates section G-G.

FIGS. 104 and 105 illustrate the tube ends 274 engaging the can 60 in multiple engagement ports 518 on the can 60. The tube ends 274 can be integral portions of the tube 272 or separated from the tube 272. The tube ends 274 can be biased radially outward from the tube and forced radially inward by an external force, or biased radially inward and forced radially outward by an external force. The engagement ports 518 can be shaped and sized to receive the lips 276 and restrain the motion of the lips in one or two dimensions.

Figure 106:
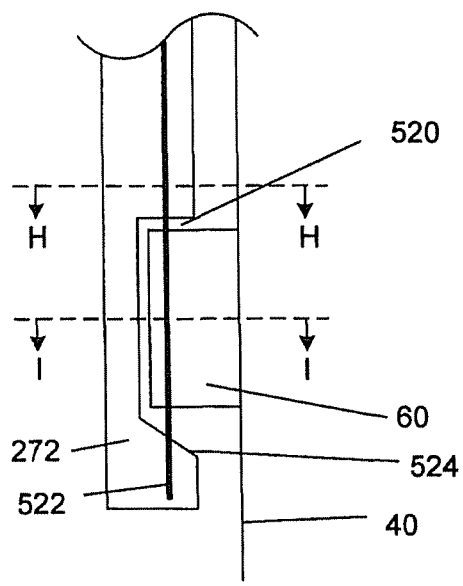
FIG. 106 illustrates the complementary fixturing device secured with an engagement rod to the tube.
Figure 107:
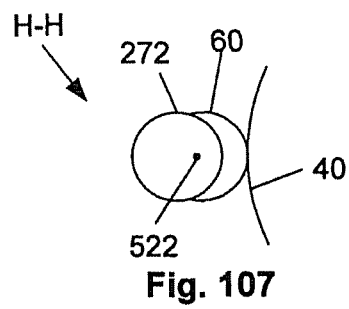
FIG. 107 illustrates section H-H.
Figure 108:
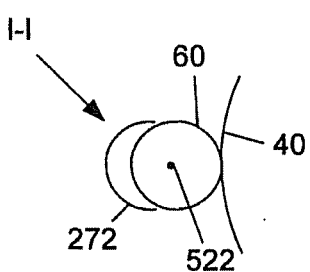
FIG. 108 illustrates section I-I.

FIGS. 106 to 108 illustrate the tube 272 side-engaging the can 60 substantially within a can gap 520. The tube 272 can be held to the can 60 by an engagement rod 522. The engagement rod 522 can be slidably attached to the can 60 and the tube 272. When the engagement rod 522 is removed from the can 60, the tube 272 and the can 60 can be separated. The tube 272 can have an engagement slope 524 to minimize contact with the can 60 during engagement and disengagement with the can 60. When the tube 272 side-engages the can 60, the tube 272 can stay substantially clear of the supra-annular volume directly above the gasket body 40.

Figure 109:
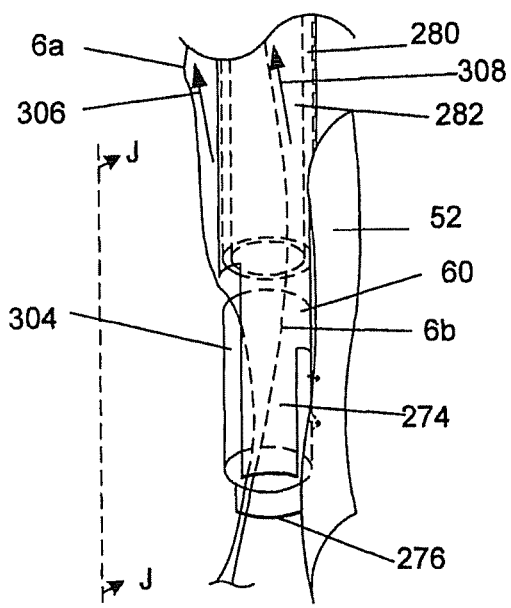
FIG. 109 illustrates various methods of using the sutures.
Figure 110:
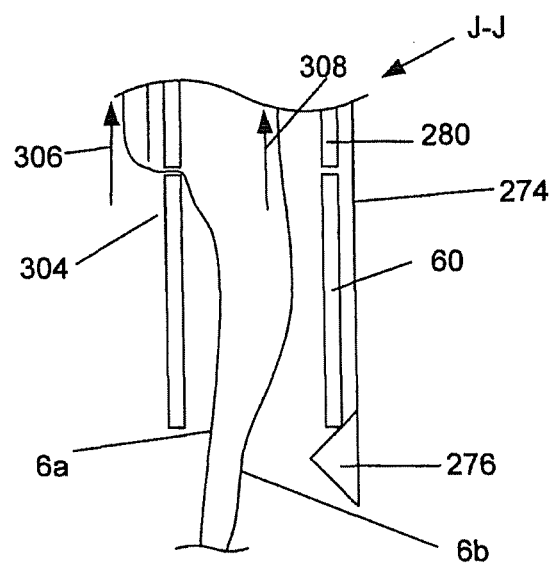
FIG. 110 illustrates section J-J.

FIGS. 109 and 110 illustrate two methods of deploying the snares and/or sutures 6. A first snare and/or suture 6a can be fed into the tube end 274 and through the can 60. The first suture 6a can then be passed through a tube window 304 and out of the tube end 274. The first suture 6a can be pulled, shown by arrow 306, on the outside of the tube 272.

A second snare and/or suture 6b can be fed into the tube end 274 and through the can 60. The second suture 6b can then continue along the tube end 274 and through the instrument port 282 in the disengagement driver 280. The second suture 6b can extend up the length of the tube 272. The second suture 6b can be pulled, shown by arrow 308, on the inside of the tube 272. One or more sutures 6 can be deployed through a single can 60.

Figure 111:
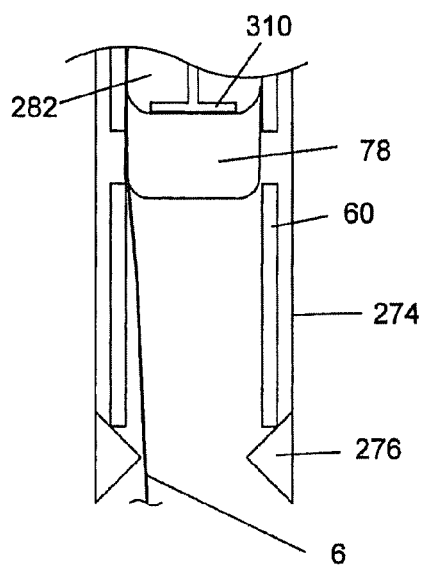
FIG. 111 illustrates an embodiment of section J-J before the plug is completely deployed.

FIG. 111 illustrates an embodiment of section J-J with the plug 78 in the process of being deployed. The plug 78 can be fed, shown by the arrow, through the instrument port 282 by an instrument driver 310, for example a catheter. The plug 78 can flex to slide within the disengagement driver 280 and around the suture 6.

Figure 112:
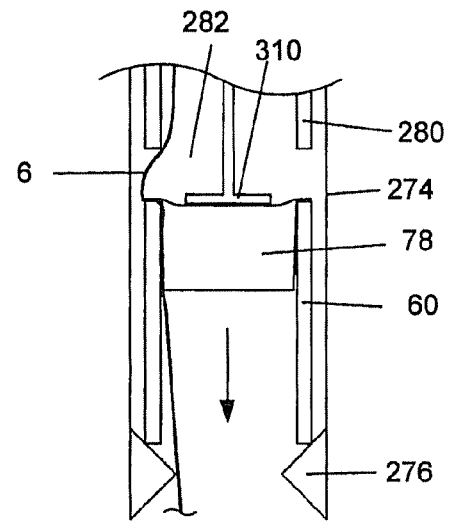
FIG. 112 illustrates an embodiment of section J-J after the plug is completely deployed.

FIG. 112 illustrates an embodiment of section J-J after the plug 78 has completely deployed. The instrument driver 310 can force the plug into the can 60, thereby forming a tight seal around the can and pressure-fixing the suture 6 between the plug 78 and the can 60.

Figure 113:
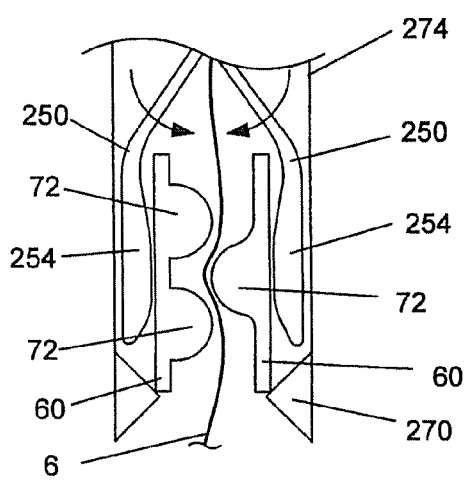
FIG. 113 illustrates an embodiment of section J-J before the complementary fixturing device is crushed.
Figure 114:
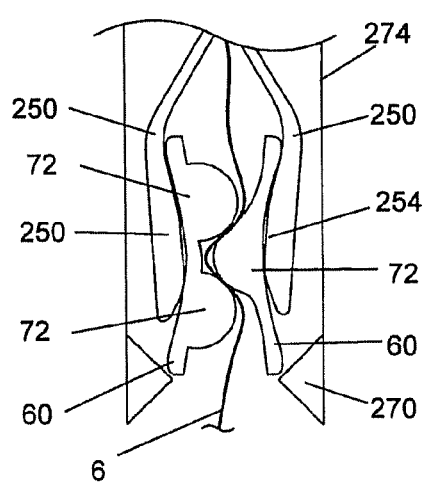
FIG. 114 illustrates an embodiment of section J-J after the complementary fixturing device is crushed.

FIGS. 113 and 114 illustrate an embodiment of section J-J showing a method of using the remote crimping tool 250 to crush the can 60. A torque, shown by the arrows, can be applied to the crushing members 254. After the torque is applied, as shown in FIG. 114, the can 60 can be crushed, pressing the internal obstacles 72 of one side of the can 60 against internal obstacles 72 of the other side of the can 60, and can fix the suture 6 between the internal obstacles 72. The can 60 can be deformable, thereby the can 60 can fix the suture 6 between the internal obstacles 72 after being crushed until the can 60 is deformed to release the suture 6 from between the internal obstacles 72.

Figure 115:
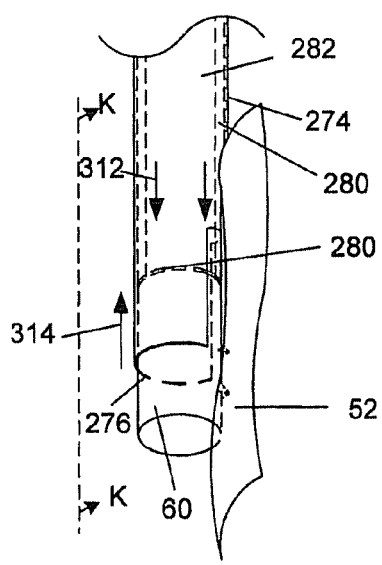
FIG. 115 illustrates the engagement device disengaging the complementary fixturing device.
Figure 116:
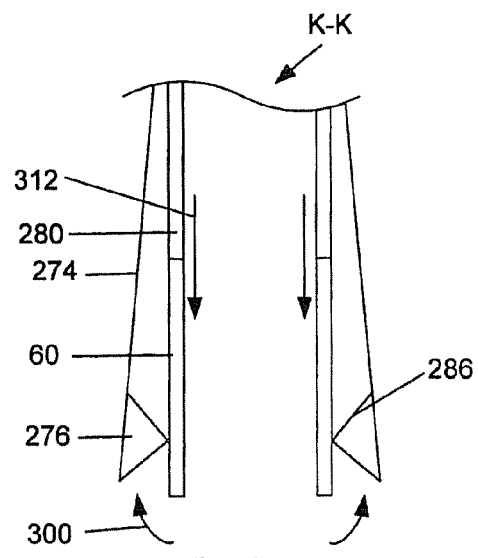
FIG. 116 illustrates section K-K of FIG. 115.
Figure 117:
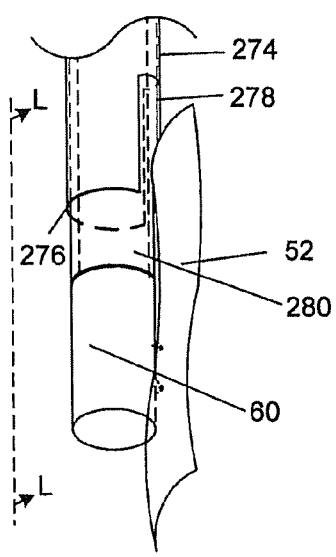
FIG. 117 illustrates the engagement device disengaged from the complementary fixturing device.
Figure 118:
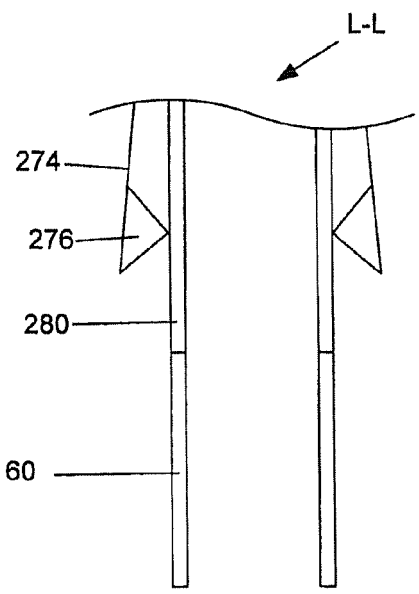
FIG. 118 illustrates section L-L of FIG. 117.

Once the suture 6 is deployed and fixed to the gasket body 40, the suture 6 can be cut and the excess suture can be removed. The suture 6 can be cut by scissors, sheared by the deployment tool 264 (e.g., between the tube end 274 and the can 60) or any combination thereof. FIGS. 115 to 118 illustrate a method of disengaging the can 60 from the deployment tool 268. FIGS. 115 and 116 illustrate pushing, shown by arrows 312, the disengagement driver 280 against the can 60. The tube end 274 can slide along the disengagement face 286, flex outward, shown by arrows 300, and can be retracted, shown by arrow 314. The tube end 274 can then be slid along the can 60 and the disengagement driver 280. FIGS. 117 and 118 illustrate the can 60 disengaged from the deployment tool 268. The lip 276 can be on the disengagement driver 280. The deployment tool 268 can then be removed for the implantation site.

Figure 119:
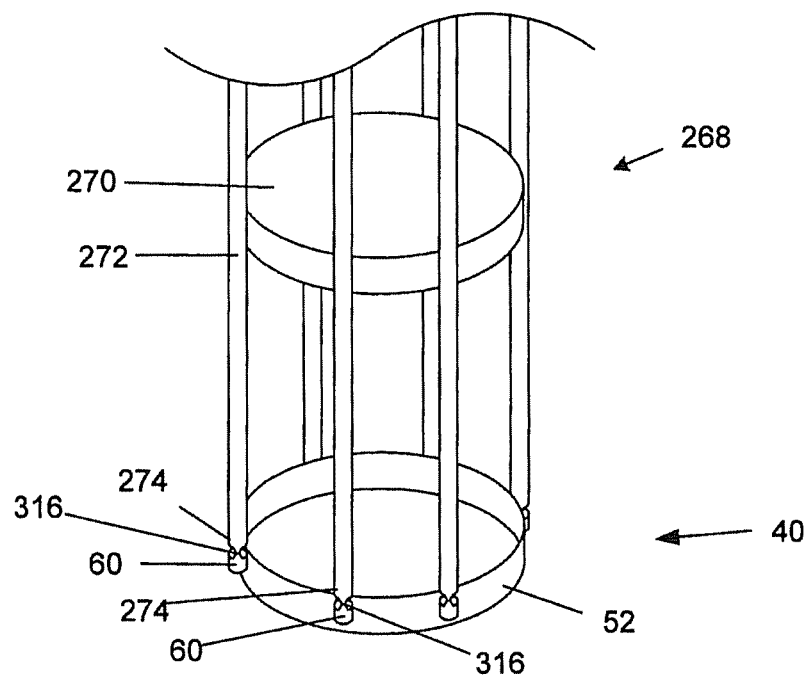
FIGS. 119 and 120 illustrate a method of deploying a gasket body with complementary fixturing devices.

FIG. 119 illustrates an deployment tool 268 engaged with the gasket body 40. The tube ends 274 can be removably attached to the cans 60. The tube ends 274 can attach to the cans 60 via necks 316. The necks 316 can be perforated or narrowed portions of the wall of the tube end 274. The necks 316 can directly attach to the cans 60.

Figure 120:
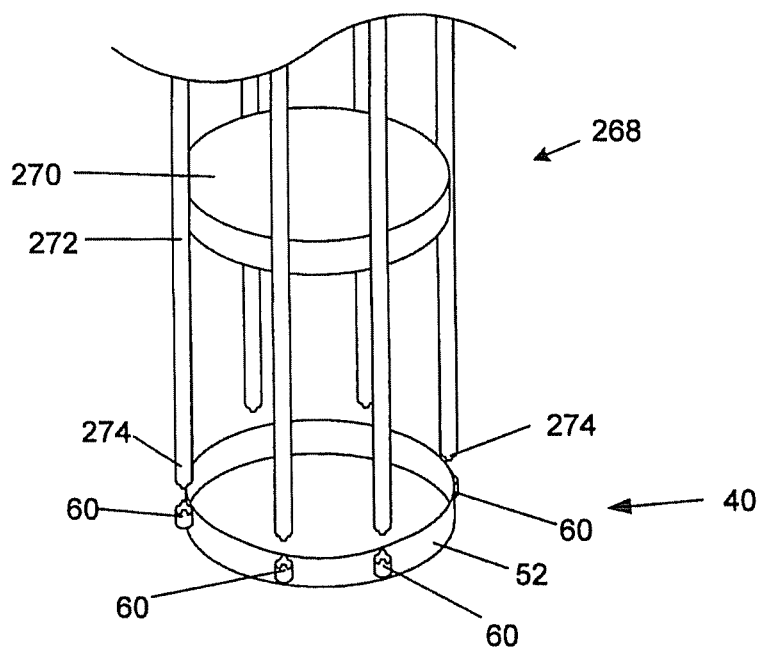

FIG. 120 illustrates the deployment tool 268 of FIG. 119 after disengaging from the gasket body 40. To disengage the deployment tool 268 from the gasket body 40 the necks 316 can break and the tube ends 274 can be pulled off the cans 60. The necks 316 can break by pulling the necks 316 against a resistive force. For example, the gasket body 40 can be secured to the implantation site with sutures 6 before pulling on the deployment tool 268. In another example, electrical current can be sent down the tubes 272 to break the necks 316. The necks 316 can be made of a conductive material that heats and breaks when sufficient current is applied.

Some tube ends 274 can be removed from the cans 60 while other tube ends 274 can remain attached to the cans 60 (not shown). The latter tube ends 274 that can still be attached to the cans 60 can be removed from the cans 60 at a later time. For example, several tube ends 274 can be removed from the cans 60 leaving tubes ends 274 still attached to the cans 60. The tube ends 274 still attached to the cans 60 can be side-engaging tube ends 274. The tube ends 274 still attached to the cans 60 can be unattached to the support 270. The support 270 and the removed tube ends 274 can be removed completely from the supra-annular space 8. The supra-annular space directly above the gasket body 40 can then be more easily accessible by medical professionals or other devices. The tube ends 274 still attached to the cans 60 can then be used as guide rods. For example, additional portions of the heart valve device, such as a connecting adapter, crown and/or leaflets, can be aligned and slid over and/or radially inside of any or all of the remaining tube ends 274. The remaining attached tube ends 274 can be removed from the cans 60 when the gasket body 40 no longer needs to be engaged to the tubes 272.

Figure 121:
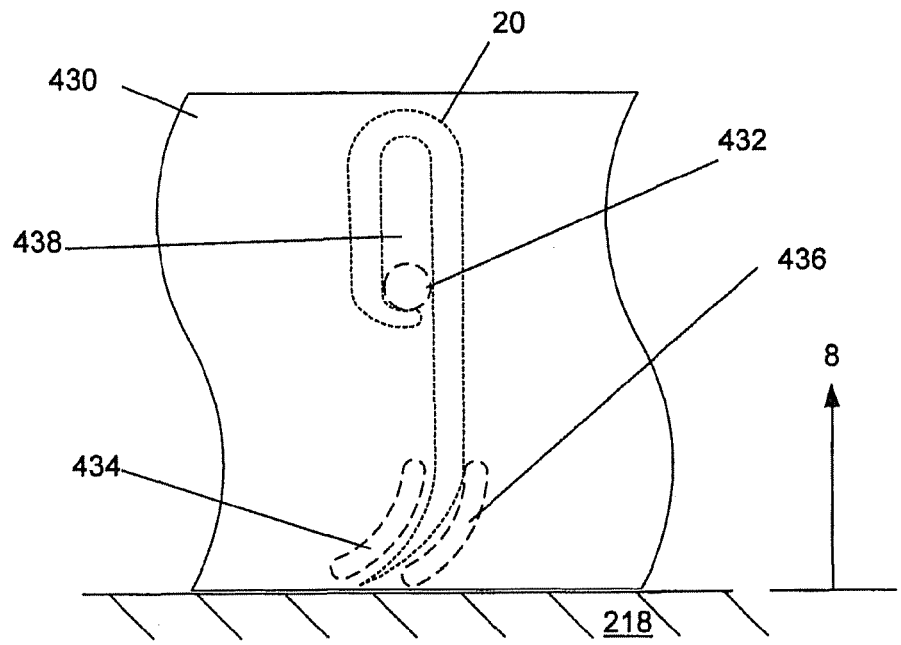
FIGS. 121 and 122 illustrate a method of using a complementary fixturing device.
Figure 122:
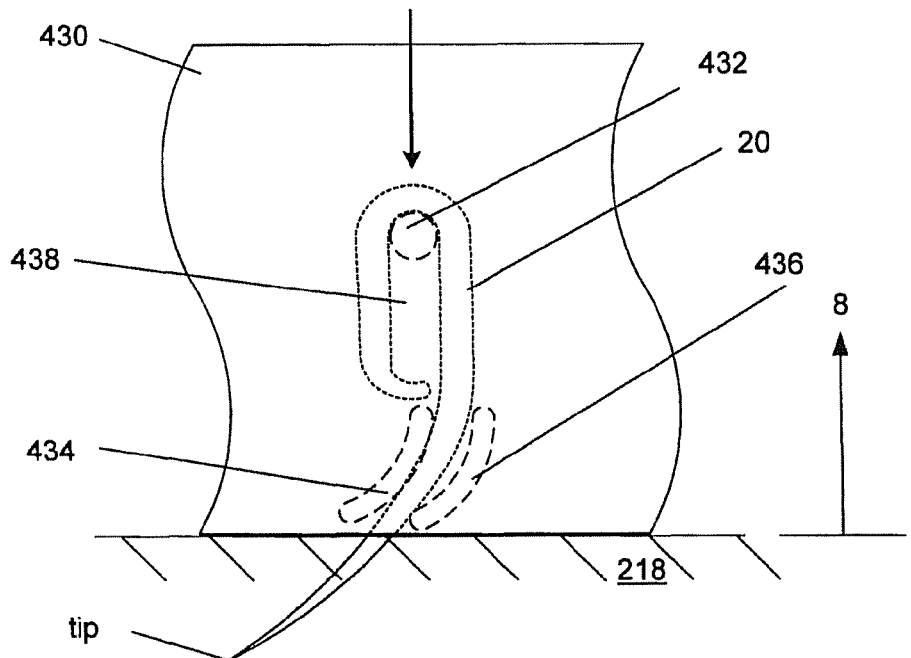

FIGS. 121 and 122 illustrate a method of using the fixturing device 20 of FIG. 43. The gasket body 40 can be placed in the supra-annular space 8. A deployment force, shown by arrow in FIG. 122, can be applied to the fixturing device 20. The fixturing device 20 can slide along the slide rod 432 and between the first and second guide blocks 434 and 436. The tip 440 can secure the gasket body 40 to the heart tissue 218. When the fixturing device 20 is deployed, the first and second guide blocks 434 and 436 can resiliently alter the shape of the fixturing device 20 to create a fiction lock between the fixturing device 20 and the first and/or second guide blocks 434 and/or 436.

Each fixturing device 20 on the gasket body 40 can be selectively deployed or left undeployed. Each deployed fixturing device 20 can be removed from the heart tissue 218 by reversing the deployment force.

Figure 123:
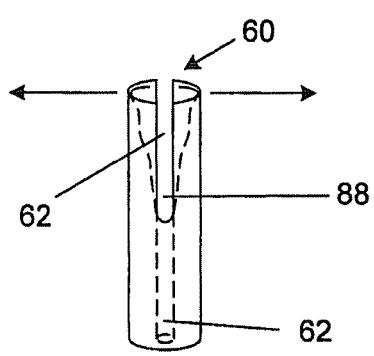
FIG. 123 illustrates an expanded complementary fixturing device.

FIG. 123 illustrates the resilient nature of the can 60 shown in FIG. 32. The can 60 can be opened by an external opening force (as shown by the arrows) to allow the suture 6 or the snare 248 to pass through the hollow channel 62. Pulling the suture 6 or the snare 248 through the hollow channel 62 with more than a minimum necessary pulling force can be sufficient to open the hollow channel 62 without the external opening force. The can 60 will resiliently return to the configuration shown in FIG. 32 when the external opening force is removed and/or the suture 6 or the snare 248 is no longer pulled by more than the minimum necessary pulling force. The minimum necessary pulling force can be determined by the dimensions and materials of the can 60, as known by those having ordinary skill in the art.

Figure 124:
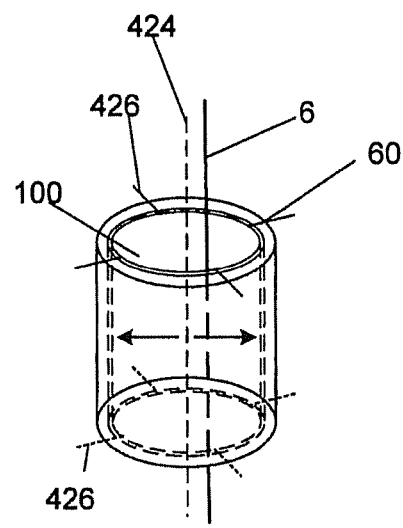
FIG. 124 illustrates a method of using the complementary fixturing device of FIG. 33.

FIG. 124 illustrates a method of using the can 60 shown in FIG. 33. The suture 6 can be fed between the can 60 and the expandable obstacle 100. The expandable obstacle 100 can then be radially expanded, shown by the arrows, for example, a balloon catheter can be deployed and/or a self-expandable stent can be released.

Figure 125:
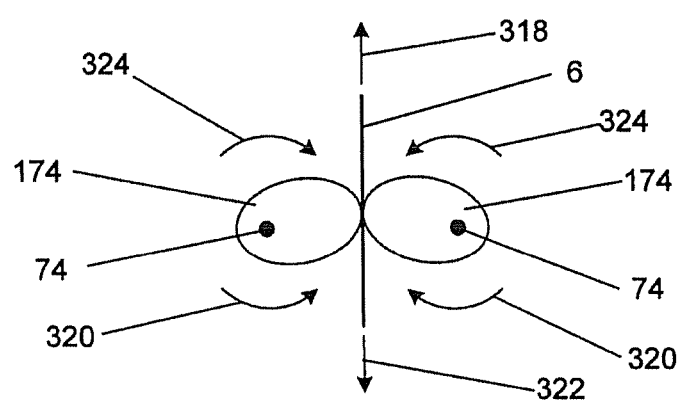
FIG. 125 illustrates a method of using the complementary fixturing devices of FIG. 65.

FIG. 125 illustrates the cams 174 with the snare 248 or the suture 6 (shown in FIG. 125 as the suture 6 for illustrative purposes) between the cams 174. The cams 174 can be self-locking cam cleats. The cams 174 shown in FIG. 125 can be biased to open upward. When the suture 6 is pulled upward, as shown by arrow 318, the cams 174 can rotate freely as shown by arrows 320. When the suture 6 is pulled downward, as shown by arrow 322, the cams 174 can rotate as shown by arrows 324 until the cams 174 contact each other, at which point the cams 174 will lock into place and prohibit further downward movement of the suture 6.

Figure 126:
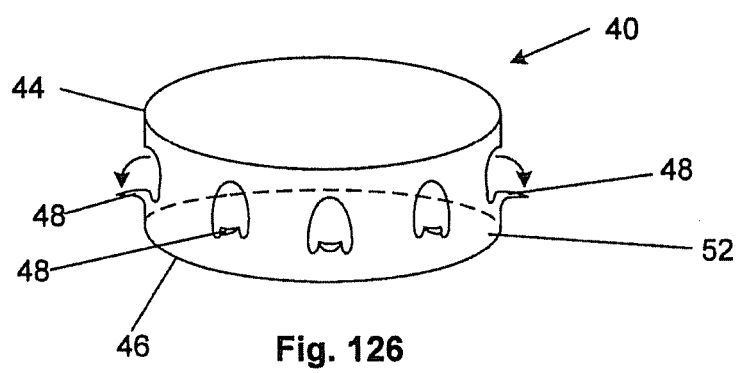
FIG. 126 illustrates a method of using the complementary fixturing devices of FIG. 21.

FIG. 126 illustrates a method of using the gasket body 40 shown in FIG. 21. Once the gasket body 40 has been positioned at the implantation site, the tabs 48 can be turned outward, shown by arrows. The downward and/or outward turned tabs 48 can engage the implantation site. The engagement can be from increased friction, puncture of the implantation site, and/or ingrowth from the implantation site into the tabs 48.

Figure 127:
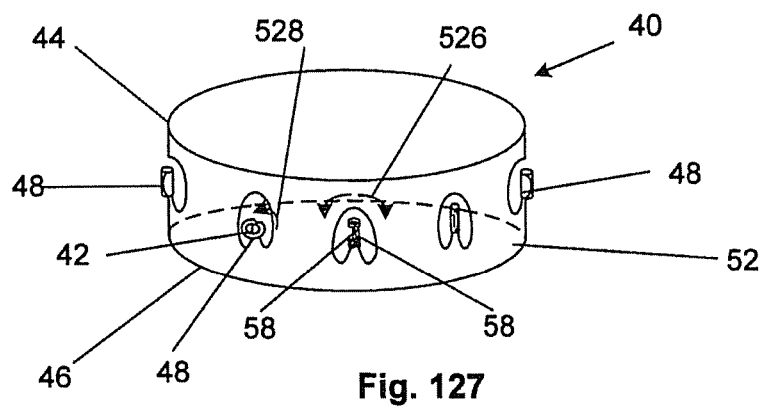
FIG. 127 illustrates a method of using the complementary fixturing devices of FIG. 22.

FIG. 127 illustrates a method of using the gasket body 40 shown in FIG. 22. Once the gasket body 40 has been positioned at the implantation site, the side wings 58 can be curled inward, shown by arrows 526, to form a cylinder through which the suture 6 can be passed. After the suture 6 is passed through the newly formed cylinder, the side wings 58 can be crushed to fix the suture 6 to the gasket body 40.

The tabs 48 can be turned outward, shown by arrow 528, and engage the implantation site, similar to the tabs 48 of the gasket body 40 of FIG. 126. The tabs 48 can be turned inward, not turned, or any tab-by-tab combination of turned outward, turned inward and not turned. The suture 6 can be passed through the receptacles 42 in the tabs 48, whether the tabs 48 have been turned inward, outward or not turned.

Figure 128:
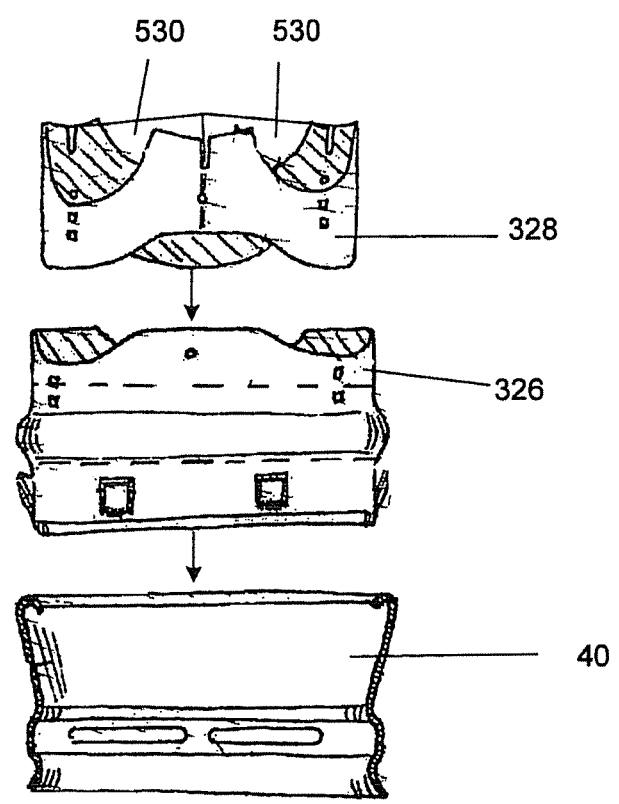
FIGS. 128-130 illustrate methods of using the gasket body with multiple-piece heart valve assemblies.

FIG. 128 illustrates a method for attaching, shown by arrows, the gasket body 40 to a connection adapter 326 and a heart valve crown 328 that can have leaflets 530, for example, U.S. Pat. No. 6,371,983 to Lane which is herein incorporated by reference in its entirety. The gasket body 40 can be used, for example, with 1-piece valves, 2-piece valves, mechanical valves and/or biological valves. A flexible gasket body 40 and/or cans 60 that are suspended from the gasket body 40 (e.g., by housing the cans 60 entirely within the sewing ring 14) can minimize the stress on the connection adapter 326 and/or the heart valve crown 328 and maximize the quality of the engagement between the gasket body 40 and the connection adapter 326 and/or the heart valve crown 328.

Figure 129:
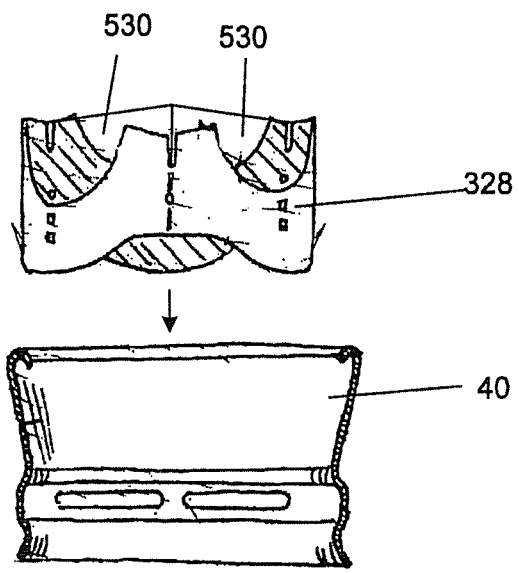
Figure 130:
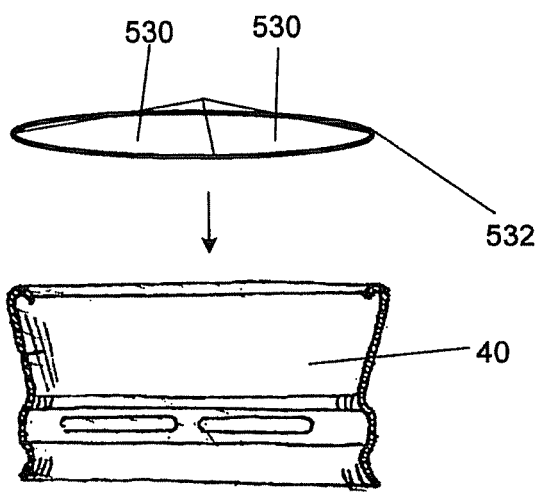

Examples of methods for attaching the gasket body 40 to the connection adapter 326 and/or the heart valve crown 328 are disclosed in U.S. patent application Ser. No. 10/327,821. The crown 328 and/or connection adapter 326 can be circumferentially resilient or otherwise circumferentially and/or radially adjustable. The crown 328 and/or connection adapter 326 can have an embodiment enabling circumferentially and/or radially adjustability by using elements similar to those employed by the first prosthesis disclosed in U.S. patent application Ser. No. 10/327,821. The gasket body 40 can be attached directly to the crown 328, as shown in FIG. 129. The gasket body 40 can be attached directly to the leaflets 530, as shown in FIG. 130. The leaflets 530 can be inserted alone into the gasket body 40 by a method known by one having an ordinary skill in the art. The leaflets 530 can have be inserted while the leaflets are held by a leaflet gasket 532, as shown in FIG. 130. The gasket body 40 may not directly attach to the leaflets 530.

It is apparent to one skilled in the art that various changes and modifications can be made to this disclosure, and equivalents employed, without departing from the spirit and scope of the invention. Elements shown with any embodiment are exemplary for the specific embodiment and can be used on other embodiments within this disclosure.

What is claimed is:

1. A method of attaching a gasket body to tissue, the method comprising:
    deploying a first attachment device through tissue at a first location and through a first complementary attachment device;
    attaching the first attachment device to the first complementary attachment device; and
    deploying a second attachment device through the tissue at a second location and through a second complementary attachment device;
    wherein the first and second complementary attachment devices are discretely formed and are attached to an annular wall of a gasket body at circumferentially spaced apart locations, such that the steps of deploying the first and second attachment devices results in the first and second attachment devices being associated with differing locations of the annular wall;
    and further wherein each of the first and second complementary attachment devices is adapted to fixedly couple to the corresponding attachment device.

2. The method of claim 1, wherein the step of attaching the first attachment device to the first complementary attachment device comprises crushing the first complementary attachment device.

3. The method of claim 1, wherein the step of attaching the first attachment device to the first complementary attachment device comprises inserting a space-occupying element into the first complementary attachment device.

4. The method of claim 1, wherein the gasket body comprises a longitudinal axis central to the gasket body, the gasket body further comprises an inner gasket radius, and an outer gasket radius, and wherein the first complementary attachment device comprises an inner attachment radius and an outer attachment radius, and wherein the inner gasket radius, the outer gasket radius, the inner attachment radius and the outer attachment radius are measured from the longitudinal axis, and wherein the outer attachment radius is greater than the outer gasket radius such that the step of deploying the first attachment device includes locating the first attachment device outside of the gasket body.

5. The method of claim 1, wherein the gasket body comprises a longitudinal axis central to the gasket body, the gasket body further comprises an inner gasket radius, and an outer gasket radius, and wherein the first complementary attachment device comprises an inner attachment radius and an outer attachment radius, and wherein the inner gasket radius, the outer gasket radius, the inner attachment radius and the outer attachment radius are measured from the longitudinal axis, and wherein the inner attachment radius is less than the inner gasket radius such that the step of deploying the first attachment device includes locating the first attachment device within the inner gasket radius.

6. A method of attaching a gasket body to tissue, the method comprising:

deploying a first attachment device through tissue at a first location and through a first complementary attachment device;

deploying a second attachment device through the tissue at a second location and through a second complementary attachment device;

wherein the first and second complementary attachment devices are discretely formed and are attached to an annular wall of the gasket body at circumferentially spaced apart locations, such that the steps of deploying the first and second attachment devices results in the first and second attachment devices being associated with differing locations of the annular wall;

and further wherein each of the first and second attachment devices is fixedly coupled to the corresponding complementary attachment device.

7. The method of claim 6, wherein the first attachment device is fixedly coupled to the first complementary attachment device by crushing the first complementary attachment device.

8. The method of claim 6, wherein the first attachment device is fixedly coupled to the first complementary attachment device by inserting a space-occupying element into the first complementary attachment device.

9. The method of claim 6, wherein the gasket body comprises a longitudinal axis central to the gasket body, the gasket body further comprises an inner gasket radius, and an outer gasket radius, and wherein the first complementary attachment device comprises an inner attachment radius and an outer attachment radius, and wherein the inner gasket radius, the outer gasket radius, the inner attachment radius and the outer attachment radius are measured from the longitudinal axis, and wherein the outer attachment radius is greater than the outer gasket radius such that the step of deploying the first attachment device includes locating the first attachment device outside of the gasket body.

10. The method of claim 6, wherein the gasket body comprises a longitudinal axis central to the gasket body, the gasket body further comprises an inner gasket radius, and an outer gasket radius, and wherein the first complementary attachment device comprises an inner attachment radius and an outer attachment radius, and wherein the inner gasket radius, the outer gasket radius, the inner attachment radius and the outer attachment radius are measured from the longitudinal axis, and wherein the inner attachment radius is less than the inner gasket radius such that the step of deploying the first attachment device includes locating the first attachment device within the inner gasket radius.

11. A method of attaching a gasket body to tissue, wherein the gasket body comprises a gasket wall, the method comprising:

deploying a first attachment device through a first receptacle attached to the gasket body, attaching the first attachment device to the tissue, attaching the first attachment device to the first receptacle, deploying a second attachment device through a second receptacle attached to the gasket body, the second receptacle being discrete from the first receptacle and attached to the gasket body at a location circumferentially spaced from the first receptacle;

attaching the second attachment device to the tissue, and attaching the second attachment device to the second receptacle.

12. A method of attaching a gasket body to tissue, the method comprising:

deploying a first attachment device through a first complementary attachment device attached to the gasket body, attaching the first attachment device to the tissue, attaching the first attachment device to the first complementary attachment device, deploying a second attachment device through a second complementary attachment device that is discrete from the first complementary attachment device and is attached to the gasket body at a location circumferentially spaced from the first complementary attachment device, attaching the second attachment device to the tissue, and attaching the second attachment device to the second complementary attachment device, wherein the first and second complementary attachment devices are located on an outer radial side of the gasket body.

* * * * *